(12) United States Patent
Clifford et al.

(10) Patent No.: US 8,109,991 B2
(45) Date of Patent: **\*Feb. 7, 2012**

(54) ENDOPROSTHESIS HAVING FOOT EXTENSIONS

(75) Inventors: Anton Clifford, Mountain View, CA (US); Jeff Pappas, Santa Clara, CA (US); Erik Eli, San Mateo, CA (US)

(73) Assignee: Abbot Laboratories, Abbott Park, IL (US)

( \* ) Notice: Subject to any disclaimer, the term of this patent is extended or adjusted under 35 U.S.C. 154(b) by 0 days.

This patent is subject to a terminal disclaimer.

(21) Appl. No.: 12/580,459

(22) Filed: Oct. 16, 2009

(65) Prior Publication Data

US 2010/0049304 A1     Feb. 25, 2010

Related U.S. Application Data

(63) Continuation of application No. 11/228,621, filed on Sep. 16, 2005, now Pat. No. 7,625,401, which is a continuation-in-part of application No. 10/992,976, filed on Nov. 19, 2004, now Pat. No. 7,625,398, which is a continuation-in-part of application No. 10/430,644, filed on May 6, 2003, now Pat. No. 7,128,756.

(51) Int. Cl.
*A61F 2/82* (2006.01)
(52) U.S. Cl. ................................. 623/1.16; 623/1.42
(58) Field of Classification Search .......... 623/1.11–1.48
See application file for complete search history.

(56) References Cited

U.S. PATENT DOCUMENTS

| 3,561,102 | A | 2/1971 | Diemer |
| 4,503,569 | A | 3/1985 | Dotter |
| 4,580,568 | A | 4/1986 | Gianturco |
| 4,830,003 | A | 5/1989 | Wolff et al. |
| 4,856,516 | A | 8/1989 | Hillstead |
| 5,102,417 | A | 4/1992 | Palmaz |

(Continued)

FOREIGN PATENT DOCUMENTS

DE     10223399     12/2003

(Continued)

OTHER PUBLICATIONS

Notice of Allowance mailed on Apr. 27, 2010 for U.S. Appl. No. 11/358,279.

(Continued)

*Primary Examiner* — Suzette J. Gherbi
(74) *Attorney, Agent, or Firm* — Baker Botts LLP

(57) ABSTRACT

Endoprosthesis, such as a stent, includes at least one annular element defined by a first set of strut members interconnected to define apices proximate opposite sides of the annular element. The annular element further includes a foot extension extending between at least one pair of circumferentially-adjacent strut members. The foot extension has first and second foot portions extending circumferentially from corresponding ends of the circumferentially-adjacent strut members, and are contoured to provide at least two areas of flexure. The first and second foot portions are joined at a toe portion of the foot extension, and define a circumferentially-directed apex between the pair of circumferentially-adjacent strut members. Preferably, at least one or more additional annular elements, each defined by interconnected strut members, are provided. The annular elements are generally expandable between a delivery configuration and a deployed configuration. The annular elements are longitudinally aligned and connected at connection locations with connectors, wherein at least one of the connectors is constructed of a bio-absorbable material.

35 Claims, 48 Drawing Sheets

U.S. PATENT DOCUMENTS

| | | | |
|---|---|---|---|
| 5,104,404 A | 4/1992 | Wolff | |
| 5,356,423 A | 10/1994 | Tihon et al. | |
| 5,403,341 A | 4/1995 | Solar | |
| 5,449,373 A | 9/1995 | Pinchasik et al. | |
| 5,540,713 A | 7/1996 | Schnepp-Pesch et al. | |
| 5,554,181 A | 9/1996 | Das | |
| 5,591,223 A | 1/1997 | Lock et al. | |
| 5,601,593 A | 2/1997 | Freitag | |
| 5,607,442 A | 3/1997 | Fischell et al. | |
| 5,697,971 A | 12/1997 | Fischell et al. | |
| 5,725,572 A | 3/1998 | Lam et al. | |
| 5,755,771 A | 5/1998 | Penn et al. | |
| 5,776,162 A | 7/1998 | Kleshinski | |
| 5,810,868 A | 9/1998 | Lashinski et al. | |
| 5,817,152 A | 10/1998 | Birdsall et al. | |
| 5,827,321 A | 10/1998 | Roubin et al. | |
| 5,853,419 A | 12/1998 | Imran | |
| 5,858,556 A | 1/1999 | Eckert et al. | |
| 5,860,999 A | 1/1999 | Schnepp-Pesch et al. | |
| 5,902,317 A | 5/1999 | Kleshinski et al. | |
| 5,911,754 A | 6/1999 | Kanesaka et al. | |
| 5,913,895 A | 6/1999 | Burpee et al. | |
| 5,922,020 A | 7/1999 | Klein et al. | |
| 5,928,280 A | 7/1999 | Hansen et al. | |
| 5,938,682 A | 8/1999 | Hojeibane et al. | |
| 5,938,697 A | 8/1999 | Killion et al. | |
| 6,013,091 A | 1/2000 | Ley et al. | |
| 6,017,365 A | 1/2000 | Von Oepen | |
| 6,022,237 A | 2/2000 | Esh | |
| 6,022,374 A | 2/2000 | Imran | |
| 6,027,526 A | 2/2000 | Limon et al. | |
| 6,027,528 A | 2/2000 | Tomonto et al. | |
| 6,042,606 A | 3/2000 | Frantzen | |
| 6,053,940 A | 4/2000 | Wijay | |
| 6,053,941 A | 4/2000 | Lindenberg et al. | |
| 6,068,656 A | 5/2000 | Von Oepen | |
| 6,090,127 A | 7/2000 | Globerman | |
| 6,099,561 A | 8/2000 | Alt | |
| 6,113,627 A | 9/2000 | Jang | |
| 6,129,754 A | 10/2000 | Kanesaka et al. | |
| 6,136,023 A | 10/2000 | Boyle | |
| 6,143,022 A | 11/2000 | Shull et al. | |
| 6,183,507 B1 | 2/2001 | Lashinski et al. | |
| 6,190,406 B1 | 2/2001 | Duerig et al. | |
| 6,193,744 B1 | 2/2001 | Ehr et al. | |
| 6,193,747 B1 | 2/2001 | Von Oepen | |
| 6,200,334 B1 | 3/2001 | Jang | |
| 6,206,911 B1 | 3/2001 | Milo | |
| 6,231,598 B1 | 5/2001 | Berry et al. | |
| 6,241,757 B1 | 6/2001 | An et al. | |
| 6,245,100 B1 | 6/2001 | Davila et al. | |
| 6,253,443 B1 | 7/2001 | Johnson | |
| 6,258,117 B1 | 7/2001 | Camud et al. | |
| 6,270,524 B1 | 8/2001 | Kim | |
| 6,287,336 B1 | 9/2001 | Globerman et al. | |
| 6,290,720 B1 | 9/2001 | Khosravi et al. | |
| 6,299,635 B1 | 10/2001 | Frantzen | |
| 6,309,414 B1 | 10/2001 | Rolando et al. | |
| 6,315,794 B1 | 11/2001 | Richter | |
| 6,331,189 B1 | 12/2001 | Wolinsky et al. | |
| 6,334,870 B1 | 1/2002 | Ehr et al. | |
| 6,334,871 B1 | 1/2002 | Dor et al. | |
| 6,340,366 B2 | 1/2002 | Wijay | |
| 6,342,067 B1 | 1/2002 | Mathis et al. | |
| 6,344,053 B1 | 2/2002 | Boneau | |
| 6,348,065 B1 | 2/2002 | Brown et al. | |
| 6,350,277 B1 | 2/2002 | Kocur | |
| 6,352,552 B1 | 3/2002 | Levinson et al. | |
| 6,355,827 B1 | 3/2002 | Komoschinski et al. | |
| 6,387,124 B1 | 5/2002 | Buscemi et al. | |
| 6,402,777 B1 | 6/2002 | Globerman et al. | |
| 6,409,752 B1 | 6/2002 | Boatman et al. | |
| 6,409,754 B1 * | 6/2002 | Smith et al. ................... 623/1.16 | |
| 6,416,543 B1 | 7/2002 | Hilaire et al. | |
| 6,423,084 B1 | 7/2002 | St. Germain | |
| 6,423,090 B1 | 7/2002 | Hancock | |
| 6,428,570 B1 | 8/2002 | Globerman | |
| 6,432,133 B1 | 8/2002 | Lau et al. | |
| 6,443,982 B1 | 9/2002 | Israel et al. | |
| 6,464,720 B2 | 10/2002 | Boatman et al. | |
| 6,464,722 B2 | 10/2002 | Israel et al. | |
| 6,475,236 B1 | 11/2002 | Roubin et al. | |
| 6,475,239 B1 | 11/2002 | Campbell et al. | |
| 6,485,510 B1 | 11/2002 | Camrud et al. | |
| 6,506,211 B1 | 1/2003 | Skubitz et al. | |
| 6,511,505 B2 | 1/2003 | Cox et al. | |
| 6,558,415 B2 | 5/2003 | Thompson | |
| 6,592,614 B2 | 7/2003 | Lenker et al. | |
| 6,699,280 B2 * | 3/2004 | Camrud et al. ............... 623/1.16 | |
| 7,060,089 B2 | 6/2006 | Ley et al. | |
| 7,128,756 B2 | 10/2006 | Lowe et al. | |
| 7,195,640 B2 | 3/2007 | Falotico et al. | |
| 7,559,947 B2 | 7/2009 | Lowe et al. | |
| 7,625,398 B2 | 12/2009 | Clifford et al. | |
| 7,625,401 B2 * | 12/2009 | Clifford et al. ............... 623/1.38 | |
| 7,763,066 B2 | 7/2010 | Parker | |
| 2001/0014822 A1 | 8/2001 | Milo | |
| 2001/0027337 A1 | 10/2001 | Di Caprio | |
| 2001/0027339 A1 | 10/2001 | Boatman et al. | |
| 2001/0032014 A1 | 10/2001 | Yang et al. | |
| 2001/0044648 A1 | 11/2001 | Wolinsky et al. | |
| 2001/0044653 A1 | 11/2001 | Kveen et al. | |
| 2001/0047200 A1 | 11/2001 | White et al. | |
| 2002/0007212 A1 | 1/2002 | Brown et al. | |
| 2002/0013616 A1 | 1/2002 | Carter et al. | |
| 2002/0016623 A1 | 2/2002 | Kula et al. | |
| 2002/0019660 A1 | 2/2002 | Gianotti et al. | |
| 2002/0022876 A1 | 2/2002 | Richter et al. | |
| 2002/0042648 A1 | 4/2002 | Schaldach et al. | |
| 2002/0045933 A1 | 4/2002 | Jang | |
| 2002/0049490 A1 | 4/2002 | Pollock | |
| 2002/0058990 A1 | 5/2002 | Jang | |
| 2002/0062149 A1 | 5/2002 | Jang | |
| 2002/0065549 A1 | 5/2002 | White et al. | |
| 2002/0095208 A1 | 7/2002 | Gregorich et al. | |
| 2002/0103529 A1 | 8/2002 | Pinchasik et al. | |
| 2002/0111669 A1 | 8/2002 | Pazienza et al. | |
| 2002/0123795 A1 | 9/2002 | Jalisi | |
| 2002/0143386 A1 | 10/2002 | Davila et al. | |
| 2002/0161428 A1 | 10/2002 | Oepen et al. | |
| 2002/0193867 A1 | 12/2002 | Gladdish et al. | |
| 2003/0060872 A1 | 3/2003 | Gomringer et al. | |
| 2003/0065242 A1 | 4/2003 | Dinkelborg et al. | |
| 2003/0153971 A1 | 8/2003 | Chandrasekaran | |
| 2004/0008039 A1 | 1/2004 | Morimoto | |
| 2004/0015229 A1 | 1/2004 | Fulkerson et al. | |
| 2004/0044399 A1 | 3/2004 | Ventura | |
| 2004/0073291 A1 | 4/2004 | Brown et al. | |
| 2004/0088039 A1 | 5/2004 | Lee et al. | |
| 2004/0167619 A1 | 8/2004 | Case et al. | |
| 2004/0172127 A1 | 9/2004 | Kantor | |
| 2005/0058684 A1 | 3/2005 | Shanley et al. | |
| 2005/0107865 A1 | 5/2005 | Clifford et al. | |
| 2006/0015173 A1 | 1/2006 | Clifford et al. | |
| 2006/0142844 A1 * | 6/2006 | Lowe et al. .................. 623/1.16 | |
| 2007/0021827 A1 | 1/2007 | Lowe et al. | |
| 2007/0021834 A1 | 1/2007 | Young et al. | |
| 2007/0213810 A1 * | 9/2007 | Newhauser et al. ......... 623/1.16 | |
| 2009/0005848 A1 | 1/2009 | Strauss et al. | |
| 2009/0076590 A1 | 3/2009 | Keating | |
| 2009/0093875 A1 | 4/2009 | Stalker et al. | |

FOREIGN PATENT DOCUMENTS

| | | |
|---|---|---|
| EP | 0177330 | 6/1991 |
| EP | 0421729 | 1/1996 |
| EP | 0931520 | 7/1999 |
| EP | 0801934 | 6/2000 |
| EP | 1095632 | 5/2001 |
| EP | 1095633 | 5/2001 |
| EP | 1356789 | 10/2003 |
| WO | WO 9732543 | 9/1997 |
| WO | WO 9733534 | 9/1997 |
| WO | WO 9939660 | 8/1999 |
| WO | WO 0006051 | 2/2000 |
| WO | WO 0013611 | 3/2000 |
| WO | WO 0035378 | 6/2000 |
| WO | WO 0054704 | 9/2000 |

| | | |
|---|---|---|
| WO | WO 0101885 | 1/2001 |
| WO | WO 0115632 | 3/2001 |
| WO | WO 0126583 | 4/2001 |
| WO | WO 0137761 | 5/2001 |
| WO | WO 0189414 | 11/2001 |
| WO | WO 0200138 | 1/2002 |
| WO | WO 0205863 | 1/2002 |
| WO | WO 0215820 | 2/2002 |
| WO | WO 0224111 | 3/2002 |
| WO | WO 0224112 | 3/2002 |
| WO | WO 0234162 | 5/2002 |
| WO | WO 0234163 | 5/2002 |
| WO | WO 0238080 | 5/2002 |
| WO | WO 02051335 | 7/2002 |
| WO | WO 02051462 | 7/2002 |
| WO | WO 02054986 | 7/2002 |
| WO | WO 02056795 | 7/2002 |
| WO | WO 02068037 | 9/2002 |
| WO | WO 02078570 | 10/2002 |
| WO | WO 02080814 | 10/2002 |
| WO | WO 02091951 | 11/2002 |
| WO | WO 03002037 | 1/2003 |
| WO | WO 03007842 | 1/2003 |
| WO | WO 03047651 | 6/2003 |
| WO | WO 03094798 | 11/2003 |
| WO | WO 2004064911 | 8/2004 |

OTHER PUBLICATIONS

Final Rejection mailed on Apr. 21, 2010 for U.S. Appl. No. 11/479,643.
U.S. Appl. No. 12/840,858, filed Jul. 21, 2010.
U.S. Appl. No. 11/358,279, Aug. 25, 2010 Request for Continued Examination, Petition to Withdraw from Issue, and Amendment.
U.S. Appl. No. 11/479,643, Jan. 19, 2010 Response to Non-Final Rejection.
Restriction Requirement mailed on Sep. 21, 2005 for U.S. Patent No. 7,128,756.
Response to the Restriction Requirement filed on Dec. 20, 2005 for U.S. Patent No. 7,128,756.
Non-Final Rejection mailed on Jan. 11, 2006 for U.S. Patent No. 7,128,756.
Response to the non-Final Rejection mailed on Jan. 11, 2006 filed on Apr. 11, 2006 for U.S. Patent No. 7,128,756.
Notice of Allowance mailed on Jun. 30, 2006 for U.S. Patent No. 7,128,756.
Non-Final Rejection mailed on Sep. 3, 2008.
Response to the non-Final Rejection mailed on Sep. 3, 2008 filed on Dec. 3, 2008 for U.S. Patent No. 7,559,947.
Notice of Allowance and Examiner Interview Summary Record mailed on Feb. 10, 2009 for U.S. Patent No. 7,559,947.
Request for Continued Examination (RCE) filed on May 11, 2009 for U.S. Patent No. 7,559,947.
Notice of Allowance mailed on Jun. 2, 2009 for U.S. Patent No. 7,559,947.
Restriction Requirement mailed on Feb. 4, 2008 for U.S. Appl. No. 10/992,976.
Response to the Restriction Requirement filed on Mar. 3, 2008 for U.S. Appl. No. 10/992,976.
Non-Final Rejection mailed on Apr. 8, 2008 for U.S. Appl. No. 10/992,976.
Response to the non-Final Rejection mailed on Apr. 8, 2008 filed on Jul. 8, 2008 for U.S. Appl. No. 10/992,976.
Notice of Non-Compliant Amendment mailed on Aug. 7, 2008 for U.S. Appl. No. 10/992,976.
Response to the non-Final Rejection mailed on Apr. 8, 2008 filed on Sep. 8, 2008 for U.S. Appl. No. 10/992,976.
Final Rejection mailed on Dec. 17, 2008 for U.S. Appl. No. 10/992,976.
Response to the Final Rejection mailed on Dec. 17, 2008 filed on Feb. 25, 2009 for U.S. Appl. No. 10/992,976.
Notice of Allowance mailed on Apr. 28, 2009 for U.S. Appl. No. 10/992,976.
Request for Continued Examination (RCE) filed on May 11, 2009 for U.S. Appl. No. 10/992,976.
Notice of Allowance mailed on Jul. 13, 2009 for U.S. Appl. No. 10/992,976.
Supplemental Notice of Allowance mailed on Nov. 3, 2009 for U.S. Appl. No. 10/992,976.
Non-Final Rejection mailed on Sep. 19, 2007 for U.S. Appl. No. 11/228,621.
Response to the non-Final Rejection mailed on Sep. 19, 2007 filed on Jan. 23, 2008 for U.S. Appl. No. 11/228,621.
Final Rejection mailed on May 23, 2008 for U.S. Appl. No. 11/228,621.
Response to the Final Rejection mailed on May 23, 2008 filed on Jul. 23, 2008 for U.S. Appl. No. 11/228,621.
Advisory Action mailed on Aug. 4, 2008 for U.S. Appl. No. 11/228,621.
Request for Continued Examination (RCE) filed on Aug. 22, 2008 for U.S. Appl. No. 11/228,621.
Non-Final Rejection mailed on Sep. 19, 2008 for U.S. Appl. No. 11/228,621.
Response to the non-Final Rejection mailed on Sep. 19, 2008 filed on Dec. 19, 2008 for U.S. Appl. No. 11/228,621.
Final Rejection mailed on Mar. 26, 2009 for U.S. Appl. No. 11/228,621.
Request for Continued Examination (RCE) filed on Jun. 26, 2009 for U.S. Appl. No. 11/228,621.
Notice of Allowance mailed on Jul. 16, 2009 for U.S. Appl. No. 11/228,621.
Non-Final Rejection mailed on Oct. 19, 2007 for U.S. Appl. No. 11/358,279.
Response to the non-Final Rejection mailed on Oct. 19, 2007 filed on Feb. 19, 2008 for U.S. Appl. No. 11/358,279.
Non-Final Rejection mailed on Jun. 13, 2008 for U.S. Appl. No. 11/358,279.
Response to the non-Final Rejection mailed on Jun. 13, 2008 filed on Oct. 14, 2008 for U.S. Appl. No. 11/358,279.
Final Rejection mailed on Feb. 6, 2009 for U.S. Appl. No. 11/358,279.
Request for Continued Examination (RCE) filed on May 6, 2009 for U.S. Appl. No. 11/358,279.
Non-Final Rejection mailed on Aug. 3, 2009 for U.S. Appl. No. 11/358,279.
Restriction Requirement mailed on Feb. 27, 2008 for U.S. Appl. No. 11/479,643.
Response to the Restriction Requirement filed on Mar. 25, 2008 for U.S. Appl. No. 11/479,643.
Non-Final Rejection mailed on Jun. 3, 2008 for U.S. Appl. No. 11/479,643.
Response to the non-Final Rejection mailed on Jun. 3, 2008 filed on Oct. 3, 2008 for U.S. Appl. No. 11/479,643.
Final Rejection mailed on Jan. 22, 2009 for U.S. Appl. No. 11/479,643.
Request for Continued Examination (RCE) filed on Apr. 22, 2009 for U.S. Appl. No. 11/479,643.
Non-Final Rejection mailed on Jul. 17, 2009 for U.S. Appl. No. 11/479,643.
U.S. Appl. No. 11/479,643, Final Rejection mailed on Apr. 27, 2010.
U.S. Appl. No. 11/479,643, Request for Continued Examination (RCE) and Response to Final Rejection filed on Sep. 27, 2010.
U.S. Appl. No. 11/479,643, Non-Final Rejection mailed on Nov. 29, 2010.
U.S. Appl. No. 11/358,279, Response to the Non-Final Rejection mailed Aug. 3, 2009 filed on Jan. 4, 2010.
U.S. Appl. No. 11/358,279, Notice of Allowance mailed Apr. 21, 2010.
U.S. Appl. No. 11/358,279, Notice of withdrawal from issue mailed Aug. 27, 2010.
U.S. Appl. No. 12/840,858, Non-Final Rejection mailed on Jan. 25, 2011.
European Search Report for EP Application No. 11168700.0, dated Jul. 4, 2011, 4 pages.

* cited by examiner

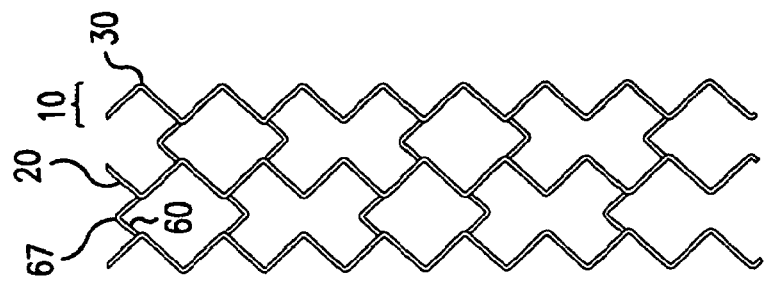
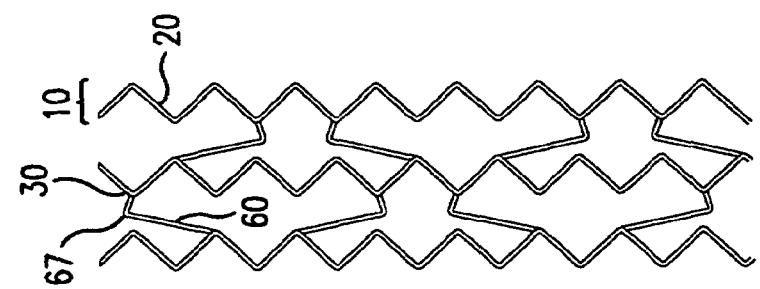
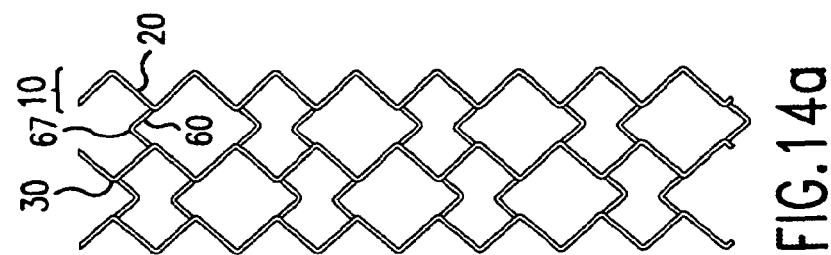

ENDOPROSTHESIS HAVING FOOT EXTENSIONS

CROSS REFERENCE TO RELATED APPLICATIONS

This application is a continuation of U.S. patent application Ser. No. 11/228,621, filed Sep. 16, 2005, which is a continuation in part of U.S. patent application Ser. No. 10/992,976 filed Nov. 19, 2004, which is a continuation in part of U.S. patent application Ser. No. 10/430,644 filed May 6, 2003, issued as U.S. Pat. No. 7,128,756 on Oct. 31, 2006, the entireties of which are herein incorporated by reference.

FIELD OF THE INVENTION

The present invention relates to an endoprosthesis for delivery and deployment within a body vessel of a human or animal. More particularly, the invention relates to a stent including at least one annular element having one or more foot extensions for improved performance characteristics and at least one connection element having a biodegradable component.

BACKGROUND OF THE INVENTION

Stents, grafts and a variety of other endoprostheses are well known and used in interventional procedures, such as for treating aneurysms, for lining or repairing vessel walls, for filtering or controlling fluid flow, and for expanding or scaffolding occluded or collapsed vessels. Such endoprostheses can be delivered and used in virtually any accessible body lumen of a human or animal, and can be deployed by any of a variety of recognized means. One recognized indication of endoprostheses, such as stents, is for the treatment of atherosclerotic stenosis in blood vessels. For example, after a patient undergoes a percutaneous transluminal coronary angioplasty or similar interventional procedure, an endoprosthesis, such as a stent, is often deployed at the treatment site to improve the results of the medical procedure and to reduce the likelihood of restenosis. The endoprosthesis is configured to scaffold or support the treated blood vessel; if desired, the endoprosthesis can also be loaded with beneficial agent so as to act as a delivery platform to reduce restenosis or the like.

The endoprosthesis is typically delivered by a catheter delivery system to a desired location or deployment site inside a body lumen of a vessel or other tubular organ. To facilitate such delivery, the endoprosthesis must be capable of having a particularly small cross profile to access deployment sites within small diameter vessels. Additionally, the intended deployment site may be difficult to access by a physician and often involves traversing the delivery system through the tortuous pathway of the anatomy. It therefore is desirable to provide the endoprosthesis with a sufficient degree of longitudinal flexibility during delivery to allow advancement through the anatomy to the deployed site.

Generally endoprosthesis' are constructed of multiple rings which are connected either through a connection section or a connection element, wherein the flexibility of the endoprosthesis is controlled by the number of connection sections or elements as well as the thickness of the struts which comprise the rings. Although it is not specifically known how much vessel restenosis can be attributed to stent rigidity, it is know that a reasonably stiff stent may injure the vessel during motion (i.e. pulsatile heart movement). Therefore, it is desirable to produce an endoprosthesis which has good stiffness properties for deployment within a vessel and wherein the stiffness properties of the endoprosthesis can be changed after deployment within a vessel. Therefore, there is a need for an endoprosthesis having multiple connections between the rings to aid in deployment of the endoprosthesis within a vessel, though it is also desirable that the connections can be severed or removed after deployment to provide a more flexible endoprosthesis.

Once deployed, the endoprosthesis should be capable of satisfying a variety of performance characteristics. The endoprosthesis should have sufficient rigidity or outer bias when deployed to perform its intended function, such as opening a lumen or supporting a vessel wall. Similarly, the endoprosthesis should have suitable flexibility along its length when deployed so as not to kink or straighten when deployed in a curved vessel. It also may be desirable to vary the rigidity or flexibility of the endoprosthesis along its length, depending upon the intended use. Additionally, it may be desirable for the endoprosthesis to provide substantially uniform or otherwise controlled coverage, e.g., as determined by the ratio of the outer surface of the endoprosthesis to the total surface of the vessel wall along a given length. For example, increased coverage may be desired for increased scaffolding, whereas decreased coverage may be desired for side access to branch vessels. Control of the cross profile and length of the endoprosthesis upon deployment also is desirable, at least for certain indications.

Numerous designs and constructions of various endoprosthesis embodiments have been developed to address one or more of the performance characteristics summarized above. For example, a variety of stent designs are disclosed in the following patents: U.S. Pat. No. 4,580,568 to Gianturco; U.S. Pat. No. 5,102,417 to Palmaz; U.S. Pat. No. 5,104,404 to Wolff; U.S. Pat. No. 5,133,732 to Wiktor; U.S. Pat. No. 5,292,331 to Boneau; U.S. Pat. No. 5,514,154 to Lau et al.; U.S. Pat. No. 5,569,295 to Lam; U.S. Pat. No. 5,707,386 to Schnepp-Pesch et al.; U.S. Pat. No. 5,733,303 to Israel et al.; U.S. Pat. No. 5,755,771 to Penn et al.; U.S. Pat. No. 5,776,161 to Globerman; U.S. Pat. No. 5,895,406 to Gray et al.; U.S. Pat. No. 6,033,434 to Borghi; U.S. Pat. No. 6,099,561 to Alt; U.S. Pat. No. 6,106,548 to Roubin et al.; U.S. Pat. No. 6,113,627 to Jang; U.S. Pat. No. 6,132,460 to Thompson; and U.S. Pat. No. 6,331,189 to Wolinsky; each of which is incorporated herein by reference.

An additional problem with existing endoprosthesis designs is the difficulty in properly placing the endoprosthesis within a vessel prior to deployment of the endoprosthesis. Current endoprosthesis designs have thinner struts which utilize less radiopaque material and therefore do not appear as well under fluoroscopy. An attempt to address the reduced radiopacity is to include at least one marker band disposed on the delivery device, wherein the marker band may be utilized to indicate an end of the endoprosthesis device or any length there along. Other methods of increasing the radiopacity of an endoprosthesis include the addition of radiopaque markers either disposed upon a surface of the endoprosthesis or within a retaining member associated with endoprosthesis. A shortcoming of present designs is that many are very difficult to manufacture and therefore lead to increased costs. Also, due to size limitations of the radiopaque material used, the markers do not provide sufficient visibility for precise placement.

Although the various designs for endoprostheses that have been developed to date may address one or more of the desired performance characteristics, there remains need for a more versatile design for an endoprosthesis that allows improvement of one or more performance characteristics without sacrificing the remaining characteristics.

SUMMARY OF THE INVENTION

The purpose and advantages of the present invention will be set forth in and are apparent from the description that follows, as well as will be learned by practice of the invention. Additional advantages of the invention will be realized and attained by the methods and devices particularly pointed out in the written description and claims hereof, as well as from the appended drawings.

To achieve these and other advantages in accordance with the purpose of the invention, as embodied herein and broadly described, the invention includes an endoprosthesis for delivery and deployment in a body lumen. The endoprosthesis includes at least one annular element defined by a first set of interconnected strut members, wherein each strut member has a first end and a second end. Preferably, the first end of selected circumferentially-adjacent strut members are interconnected to define apices proximate a first longitudinal side of the first annular element and the second end of selected circumferentially-adjacent strut members are interconnected to define apices proximate a second longitudinal side of the first annular element. The annular element further includes a foot extension extending between a pair of circumferentially-adjacent strut members. The foot extension has a first foot portion extending circumferentially from the first end of one of the circumferentially-adjacent strut members of the pair and a second foot portion extending circumferentially from the first end of the other of the circumferentially-adjacent strut members. The first and second foot portions are joined at a toe portion of the foot extension, and generally define an apex between the pair of circumferentially-adjacent strut members.

Preferably, the endoprosthesis of the invention further includes a second annular element defined by a second set of interconnected strut members, wherein each strut member of the second annular element also has a first end and a second end. Circumferentially-adjacent strut members are interconnected to define apices on opposite sides of the second annular element. The first annular element and the second annular element are aligned longitudinally adjacent to each other along a longitudinal axis and connected to each other at least one connection location. The second annular element also can include a foot extension. Additional annular elements also can be provided.

The annular elements are generally expandable between a delivery configuration and a deployed configuration. Each annular element can be defined as a continuous closed ring, or as a coiled sheet or the like. Preferably, each strut member is a straight member, aligned to be substantially parallel with the longitudinal axis of the endoprosthesis when in the delivery configuration. Selected strut members can have a uniform width or can have varied width, such as a continuous taper or increased midsection width between the opposite ends of the strut member. The apices on either side of each annular element that are not defined by a foot extension can have a V-shape, an arcuate shape, or another shape as desired.

The foot extension is contoured to provide at least two areas of flexure, and extends circumferentially at an angle relative to the longitudinal axis of the annular element. The foot extension can include straight portions, curved portions or combinations thereof to define an ankle portion, a toe portion, a base portion and a heel portion. The base portion can be a straight member, or contoured as a V-shape or the like. In a preferred embodiment, the foot extension has an average width greater than that of the remaining strut members of the annular element. With the foot extension located between longitudinally-adjacent annular elements, the base portion of the foot extension generally faces the longitudinally-adjacent annular element.

Preferably, the connection location between the longitudinally-adjacent annular elements includes the foot extension. By providing the connection location at the base portion of the foot extension, the apices proximate a side of the first annular element generally can be arranged circumferentially out of alignment, or less than 180 degrees out of phase, with the apices proximate a facing side of the second annular element. The connection location can be defined by an overlapping pattern between the longitudinally-adjacent annular elements, such as the base of a foot extension on one annular element and a corresponding apex on the other annular element. Alternatively, the connection location can include a connector extending between the annular elements. The connector can be a straight member or a shaped member, with opposites ends circumferentially either in or out of alignment, as desired. In a preferred embodiment, the connector has an L-shape, with one leg longer than the other leg. It is further contemplated that the connector may be partially or fully constructed of a bioabsorbable material, wherein after deployment within a vessel, the bioabsorbable component of the connector is absorbed thereby changing the stiffness of the endoprosthesis. In a preferred embodiment, a plurality of connection locations are provided between the adjacent annular elements, with a foot extension provided at some or all of the connection locations. The plurality of foot extensions can all extend in the same circumferential direction, or can be arranged to extend in opposing circumferential directions.

A radiopaque material preferably is incorporated in at least a portion of the endoprosthesis. For example, at least one of the annular elements can comprise radiopaque material. Alternatively, radiopaque markers can be attached to at least one of the annular elements, or the annular elements can be formed of radiopaque material. As another example, at least one of the annular elements can be formed with a first layer of base material and a second layer of radiopaque material.

In accordance with the present invention there is provided an endoprosthesis for delivery in a body lumen comprising a first set of interconnected strut members defining a first annular element, each strut member of the first annular element including a first end and a second end; a second set of interconnected strut members defining a second annular element, each strut member of the second annular element including a first end and a second end; the first annular element and the second annular element aligned longitudinally adjacent to each other along a longitudinal axis and connected to each other at at least one connection location, the first and second annular elements being expandable between a delivery configuration and a deployed configuration; at least one of the first and second annular elements including a foot extension extending between at least one pair of circumferentially-adjacent strut members, the foot extension including a first foot portion extending circumferentially from the first end of one of the circumferentially-adjacent strut members of the pair and a second foot portion extending circumferentially from the first end of the other of the circumferentially-adjacent strut members, the first and second foot portions joined at a toe portion of the foot extension, the first and second annular elements forming a generally tubular member having open ends; and a marker associated with one of open ends of the generally tubular member.

In accordance with the present invention there is provided an endoprosthesis device for delivery in a body lumen, comprising a thin-walled, generally tubular member having open ends with a first diameter and a second diameter; and at least one marker element connected to at least one end of the thin-walled generally tubular member, the at least one marker comprising a marker housing and a rivet, the rivet extending generally beyond an outer surface and an inner surface of the substantially tubular member.

In accordance with the present invention there is provided a method of manufacturing an endoprosthesis device, comprising the steps of (a) forming an endoprosthesis for delivery in a body lumen (b) smoothing surfaces of the endoprosthesis by media blasting (c) polishing the surfaces of the endoprosthesis with an electropolishing process (d) disposing a radiopaque marker within an opening formed within a structure of an endoprosthesis device (e) applying a force to said marker, thereby forming two heads on the marker, wherein each of the heads extends beyond and inner and an outer surface of the endoprosthesis device. The method may further include the step of passivation, either prior to placing the marker within the opening or after placement or any combination thereof.

It is to be understood that both the foregoing general description and the following detailed description are exemplary and are intended to provide further explanation of the invention claimed.

The accompanying drawings, which are incorporated in and constitute part of this specification, are included to illustrate and provide further understanding of the device of the invention. Together with the description, the drawings serve to explain the principles of the invention.

BRIEF DESCRIPTION OF THE DRAWINGS

FIGS. 14a through 14e show detail views, in planar format, of various alternative connector relationships between adjacent annular elements.

DETAILED DESCRIPTION OF THE PREFERRED EMBODIMENTS

Figure 1:
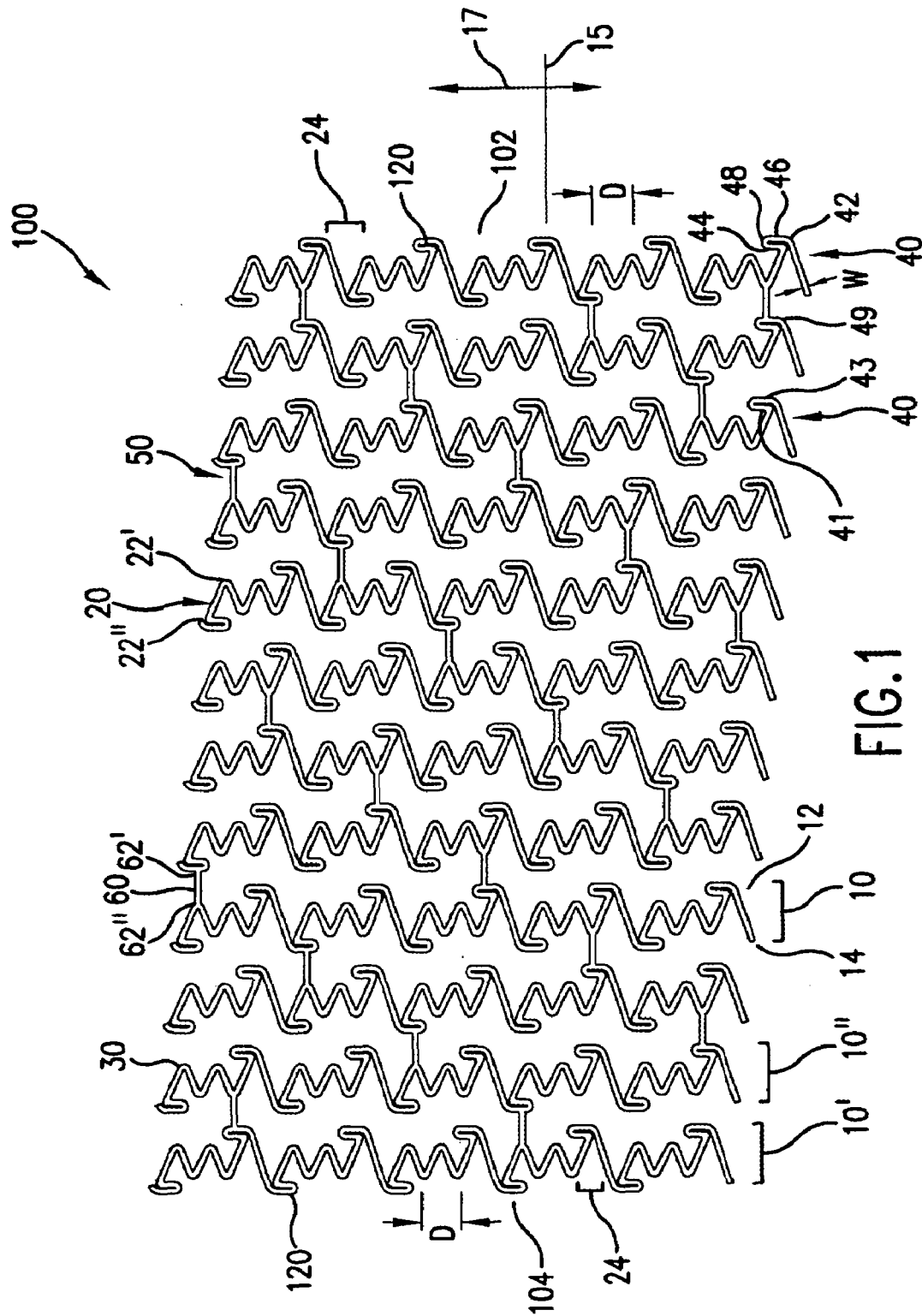
FIG. 1 shows a representative embodiment, in planar format, of an endoprosthesis in accordance with the invention.

In accordance with the present invention, an endoprosthesis is provided for delivery within a body lumen of a human or animal. The endoprosthesis can include, but is not limited to, stents, grafts, valves, occlusive devices, trocars, aneurysm treatment devices, or the like. The endoprosthesis of the present invention can be configured for a variety of intralumenal applications, including vascular, coronary, biliary, esophageal, urological, gastrointestinal or the like.

Generally, the endoprosthesis of the present invention includes a first set of interconnected strut members defining a first annular element, wherein each strut member of the first annular element include a first end and a second end. The endoprosthesis also includes a foot extension extending between a pair of circumferentially-adjacent strut members. As described further below, the foot extension has a first foot portion extending circumferentially from the first end of one of the circumferentially-adjacent strut members and a second foot portion extending circumferentially from the first end of the other of the circumferentially-adjacent strut members. The first and second foot portions are joined at a toe portion of the foot extension.

Preferably, and as embodied herein, the endoprosthesis further includes at least a second set of interconnected strut members defining a second annular element. The endoprosthesis can include additional annular elements defined by interconnected strut members as desired or needed. Each annular element generally defines a structure extending circumferentially about a longitudinal axis. The cross profile of each annular element preferably is at least arcuate, and more preferably either circular or spiral, although alternative cross profiles, such as rectilinear or the like, can be used if desired.

The first annular element is aligned longitudinally adjacent to the second annular element along the longitudinal axis, and connected to each other at at least one connection location. Preferably, the first and second annular elements generally define a tubular structure. For example, each annular element can define a continuous closed ring such that the longitudinally-aligned annular elements form a closed tubular structure having a central longitudinal axis. Alternatively, each annular element can define an open ring such that a rolled sheet or open tubular type structure is defined by the annular elements. Furthermore, each annular element can define a 360 degree turn of a helical pattern, such that the end of one annular element can be joined with the corresponding end of a longitudinally-adjacent annular element to define a continuous helical pattern along the length of the endoprosthesis.

Each strut member of the annular elements includes a first end and a second end. The strut members of each annular element are disposed circumferentially adjacent to each other, and interconnected so as to define an expandable structure. For example, and with reference to the closed tubular structure above, circumferentially-adjacent strut members of each annular element can be interconnected, either directly or indirectly, in an end-to-end format to define a continuous ring having a generally circular cross profile. By altering the angle or distance defined between circumferentially-adjacent strut members, the tubular structure can be radially expanded between a delivery configuration and a deployed configuration. As discussed in detail below, the expandable structure can be expanded by the application of an external force, such as by a balloon, or by a change in delivery conditions, such as an increase in temperature or the removal of a restraint, so as to allow the structure to self expand.

With reference to FIG. 1, for purpose of illustration and not limitation, a representative embodiment of an endoprosthesis 100 of the present invention in a deployed configuration is depicted in a planar format for clarity. As shown in FIG. 1, the endoprosthesis includes a plurality of annular elements 10 aligned longitudinally adjacent to each other along a longitudinal axis 15. Although only one annular element need be provided in accordance with the invention, it is preferable that the endoprosthesis includes a plurality of annular elements 10, depicted herein for purpose of illustration by at least a first annular element 10' and a second annular element 10".

Each annular element includes a set of interconnected strut members 20, which are disposed circumferentially about longitudinal axis 15. Each strut member has a first end 22' and a second end 22", referenced generally as end 22. The first end 22' of selected circumferentially-adjacent strut members 20 are interconnected to define apices 30 proximate a first longitudinal side 12 of each annular element 10, and the second end 22" of selected circumferentially-adjacent strut members 20 are interconnected to define apices 30 proximate a second longitudinal side 14 of the annular element. In this manner, each annular element 10 can be expanded to a deployed configuration as shown in FIG. 1 by altering or "opening" the angle defined between circumferentially-adjacent strut members 20. It also is recognized in the embodiment of FIG. 1 that circumferentially-adjacent apices 30 on each side 12, 14 of the annular element 10 are spaced apart by a circumferential distance D, such that each annular element is expanded by increasing the distance D between circumferentially-adjacent apices 30. At any given condition between the delivery configuration and the deployed configuration, the distance D can be balanced or constant from one set of circumferentially-adjacent apices to the next, or can be varied if desired.

As shown in FIG. 1, certain apices 30 on each side of the annular element 10 can be defined by interconnecting corresponding ends 22 of circumferentially-adjacent strut members directly together to form a zig-zag pattern of alternating V-shapes when deployed. Alternatively, an apex member can be provided between the corresponding ends of adjacent strut members to form a contoured apex, such as by using a straight apex member to form a flat apex as disclosed in U.S. Pat. No. 6,113,627 to Jang, or a curved apex member to form an arcuate apex as disclosed in U.S. Pat. No. 5,514,154 to Lau.

Figure 29A:
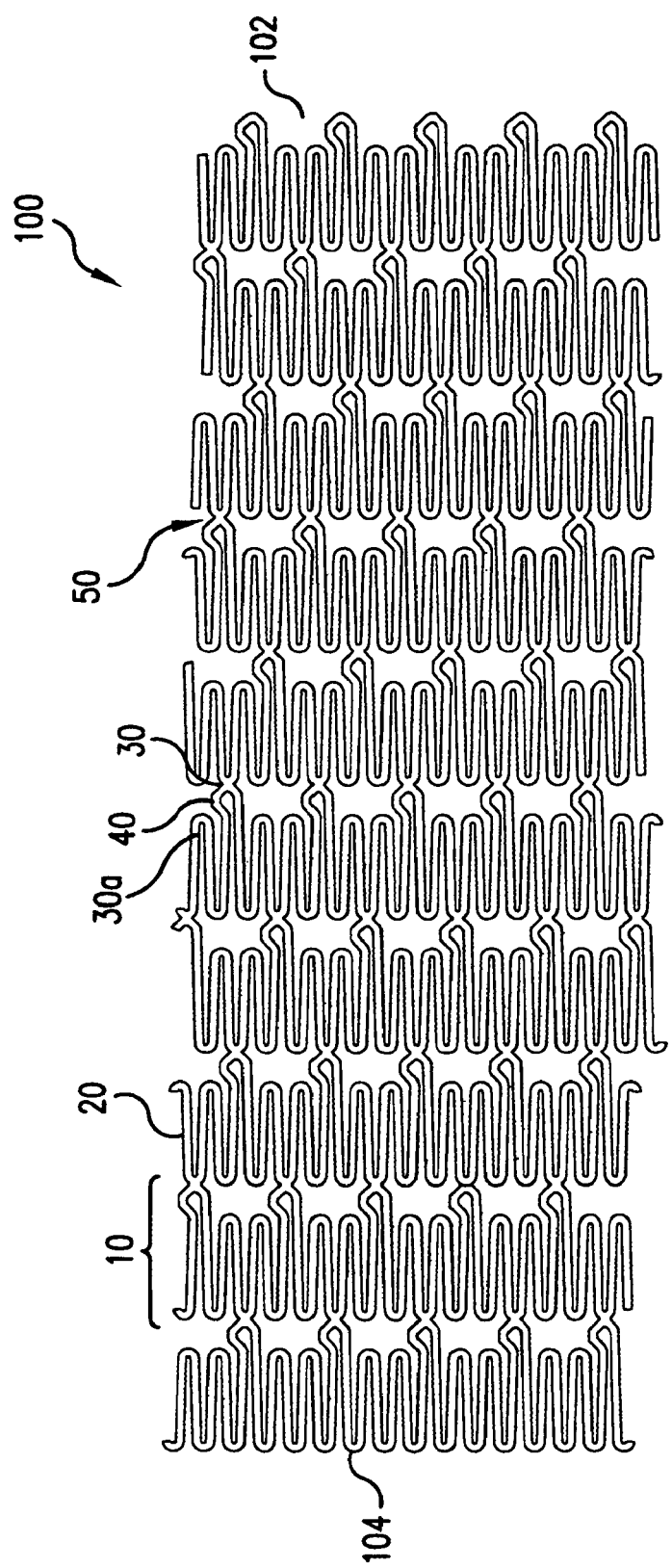
FIGS. 29a through 29f respectively show a preferred embodiment of a self-expanding stent in accordance with the present invention, (a) in planar format, (b) in a front-half side view as cut and polished from a tube, (c) in a front-half side view of a delivery configuration, (d) in a front-half side view of a deployed configuration, (e) in a perspective view of a deployed configuration, and (f) in a side view as deployed in a curved vessel.
Figure 29C:
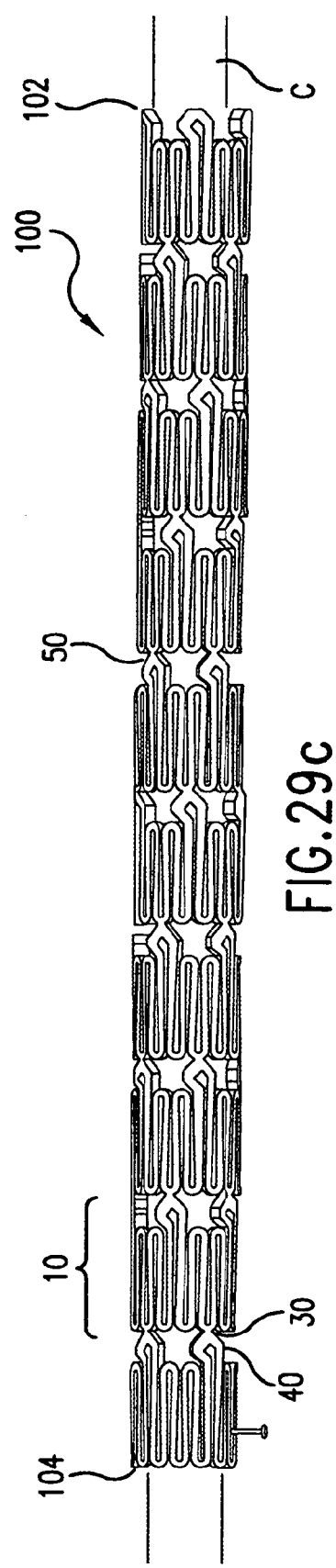
Figure 29B:
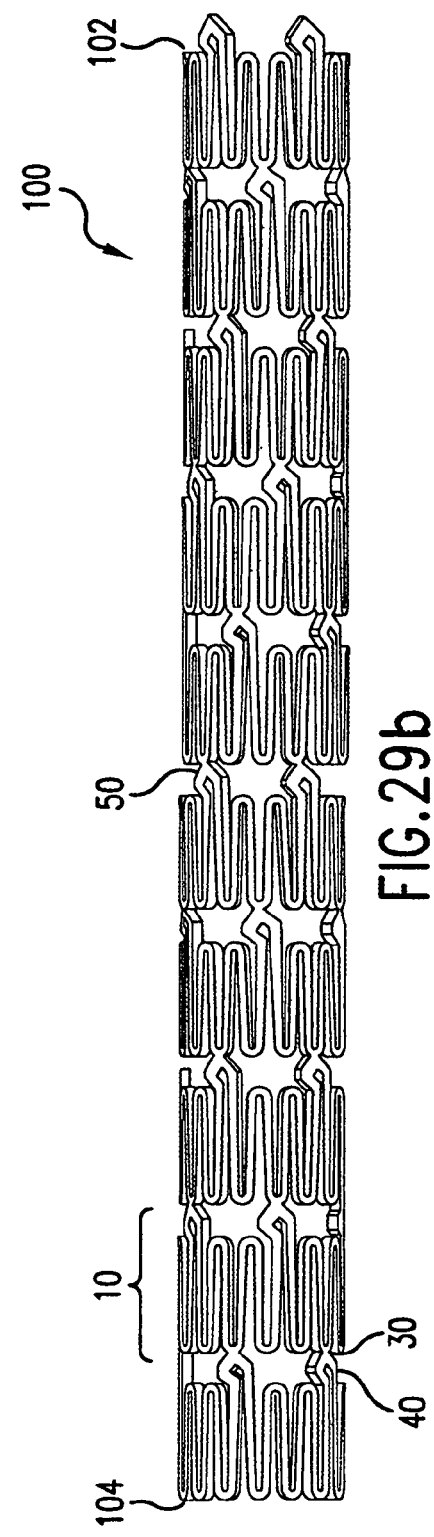
Figure 29D:
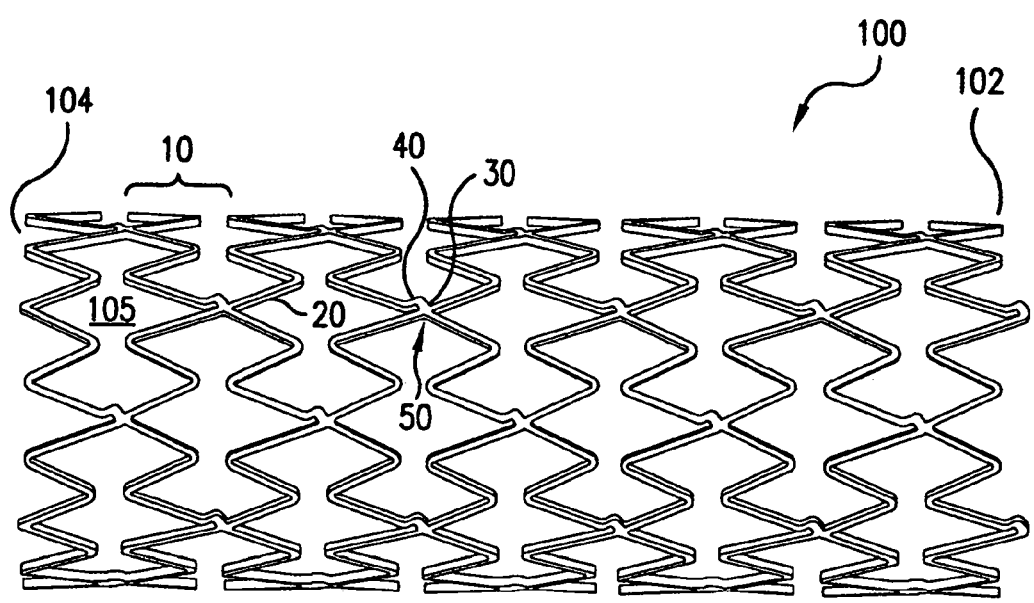
Figure 29E:
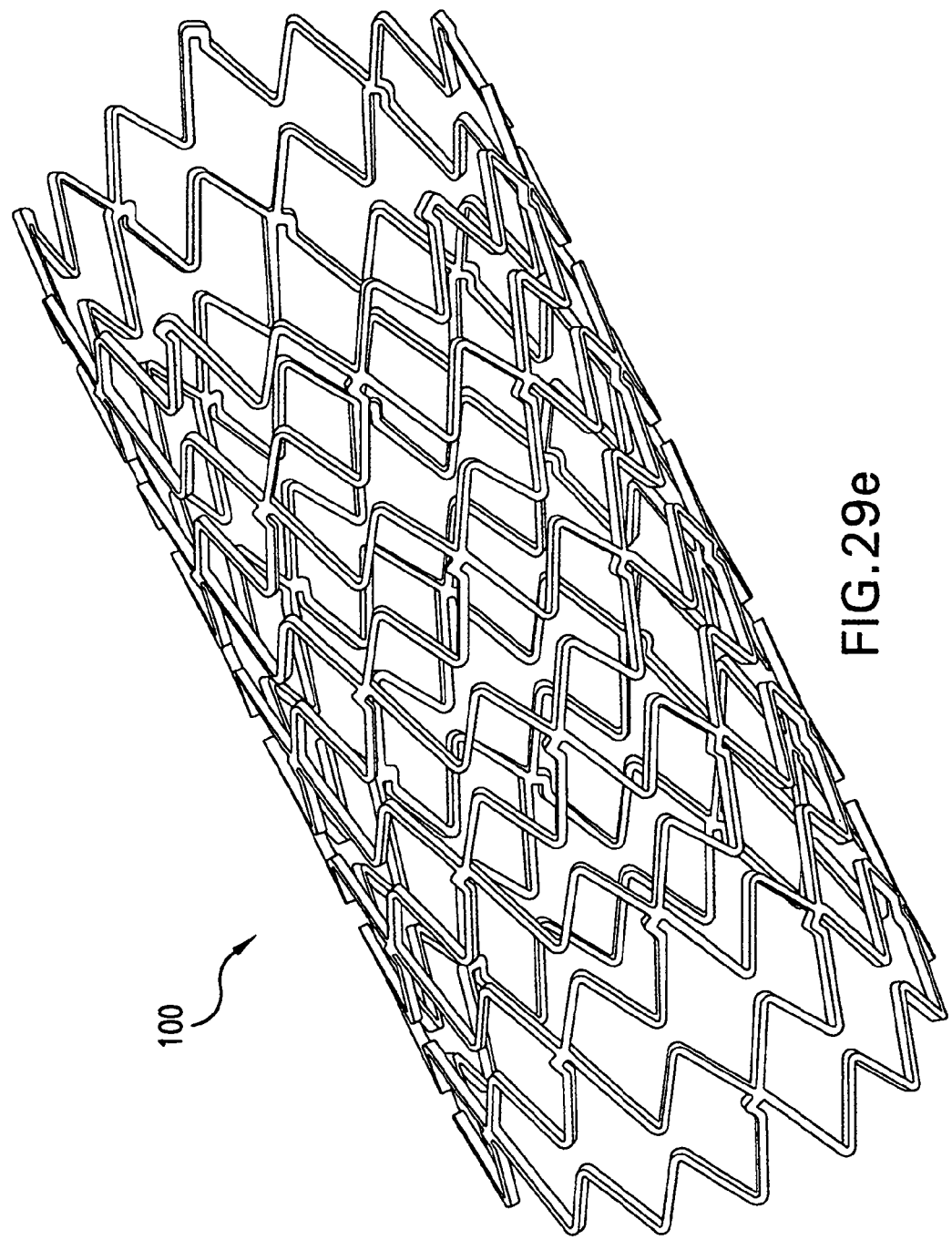
Figure 30A:
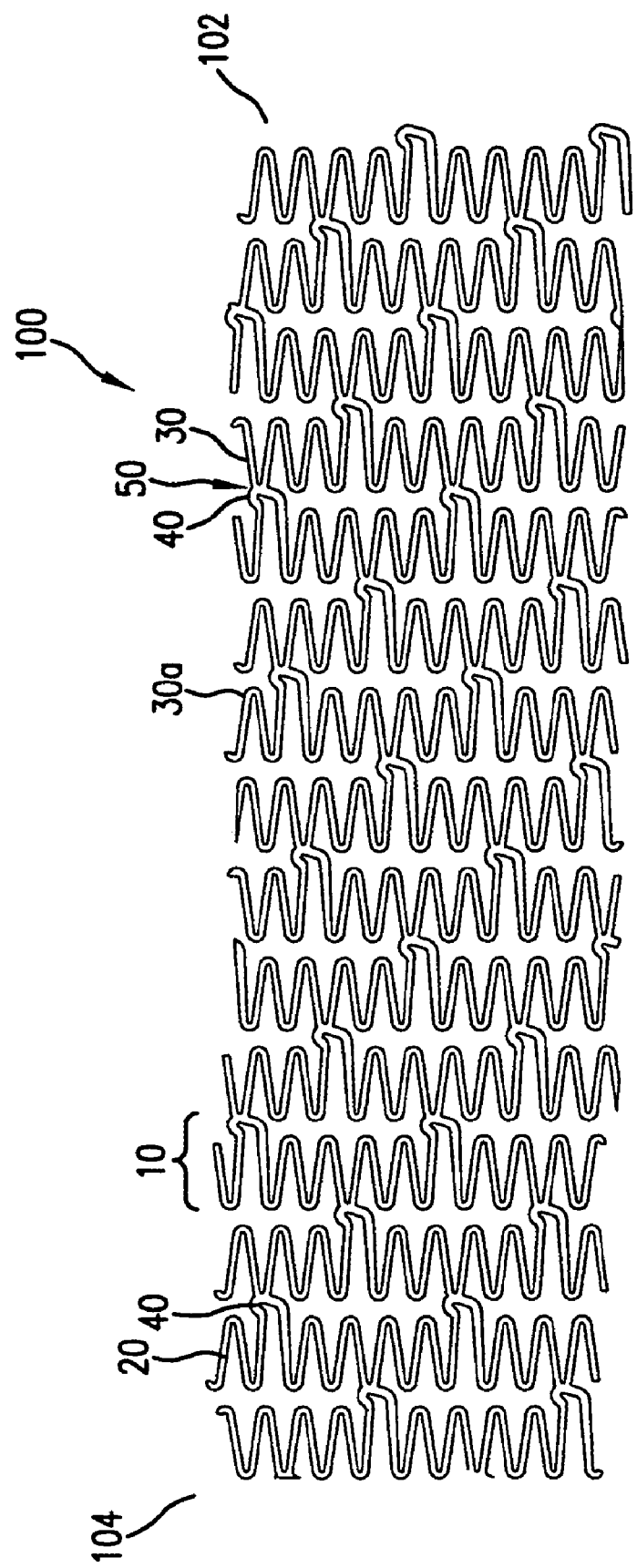
FIGS. 30a through 30f respectively show a preferred embodiment of a balloon expandable stent in accordance with the present invention, (a) in planar format, (b) in a front-half side view as cut and polished from a tube, (c) in a front-half side view of a delivery configuration, (d) in a front-half side view of a deployed configuration, (e) in a perspective view of a deployed configuration, and (f) in a side view as deployed in a curved vessel.
Figure 30B:
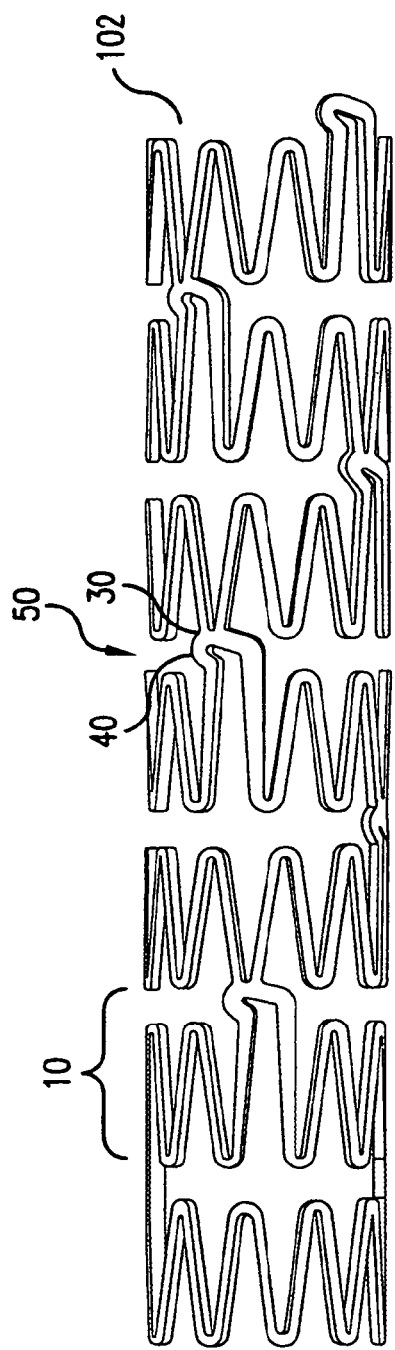
Figure 30C:
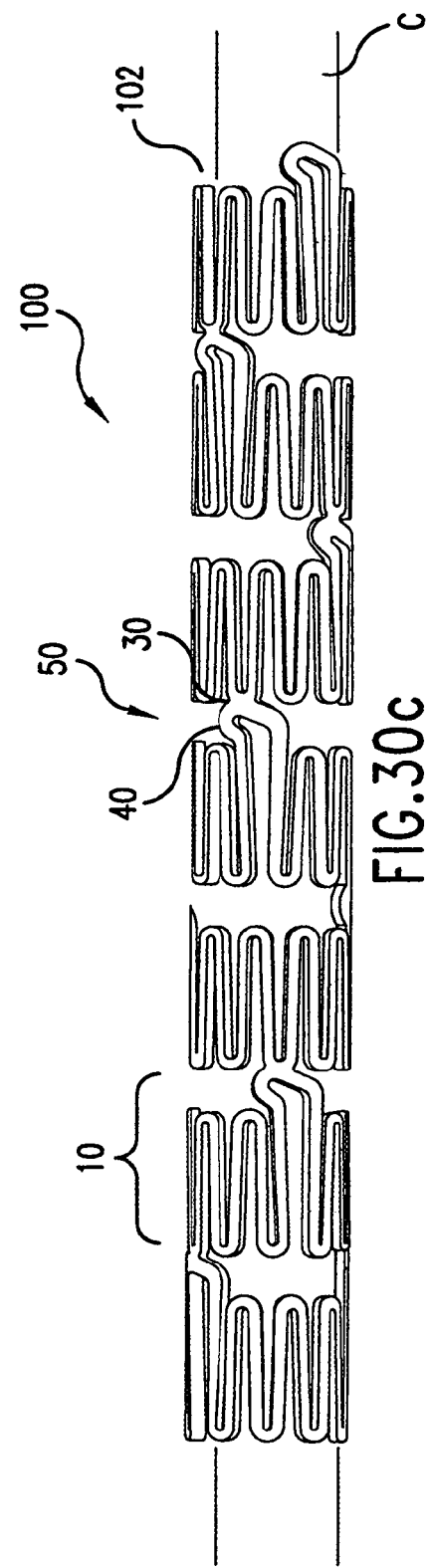
Figure 30D:
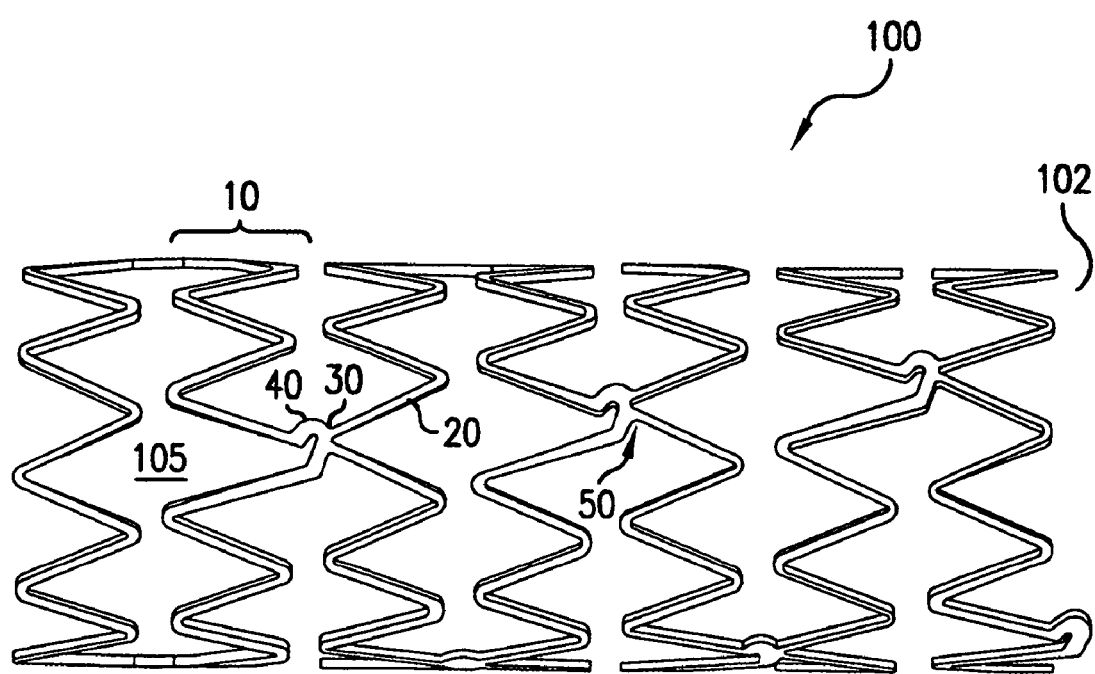
Figure 30E:
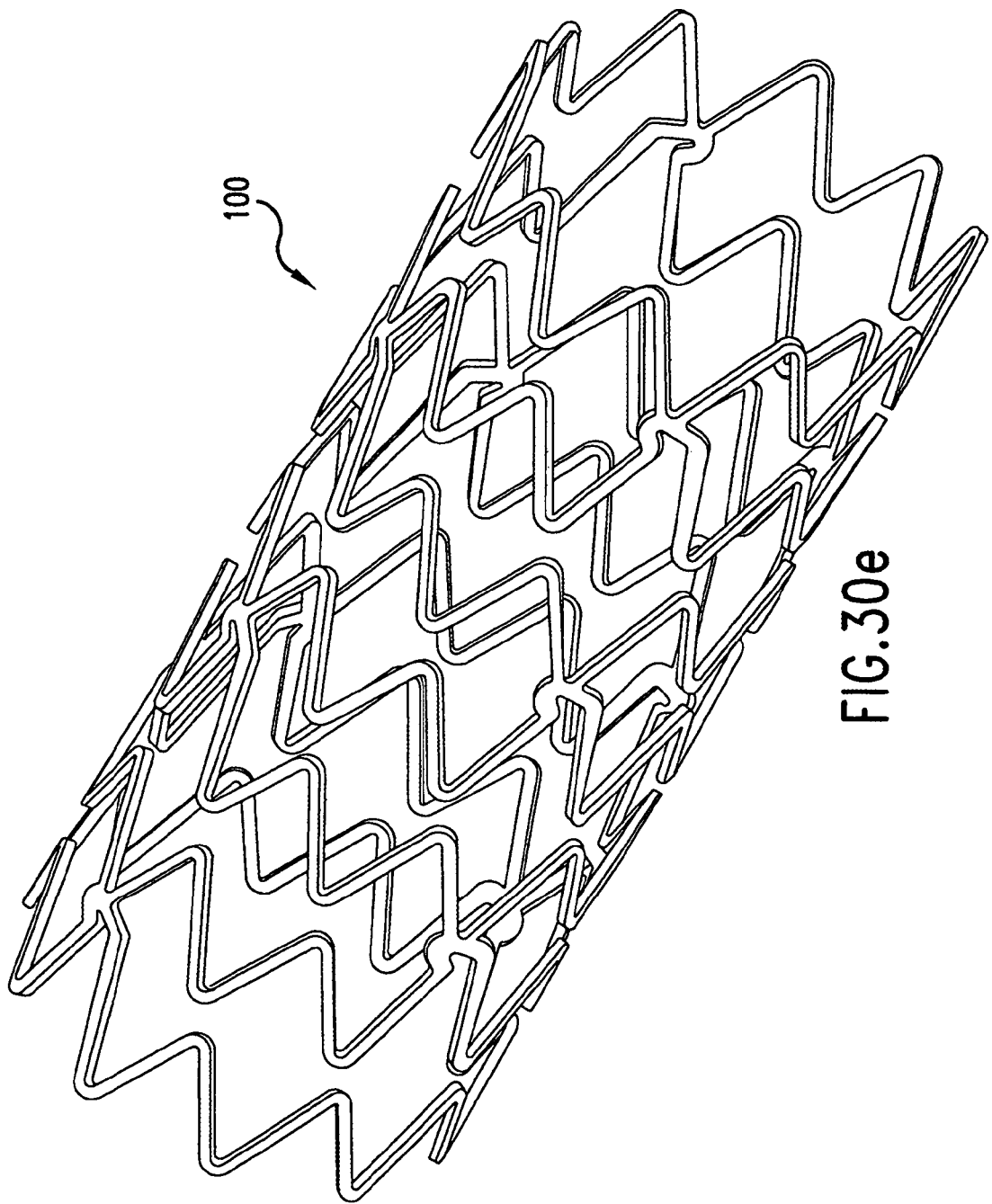

In the representative embodiment of FIG. 1, the strut members 20 of each annular element 10 are interconnected with adjacent strut members 20 to form a continuous closed ring, such as depicted more clearly in FIGS. 29e and 30e. As previously noted, however, each annular element can define an open ring to form a rolled sheet or open tubular type structure as described further with regard to FIG. 3, or can define adjacent turns of a continuous helical pattern as described with regard to FIG. 25, for purpose of illustration.

FIG. 1 also depicts each strut member 20 of the annular element 10 as a straight member. Preferably, when in the delivery configuration, the straight strut members 20 are generally aligned parallel with the longitudinal axis 15, as well as with each other, as shown for example in FIGS. 29c and 30c. Although not shown, alternative strut member shapes can be used in addition to or in lieu of the straight strut members, such as L or V-shaped strut members or the like as is known in the art. Also, the number of strut members included in each annular element will depend upon the size and desired characteristics of the endoprosthesis. For example, a greater number of strut members and interconnecting apices can be provided for increased coverage of the vessel wall by the endoprosthesis or increased cross profile of the endoprosthesis in the deployed configuration.

Figure 12A:
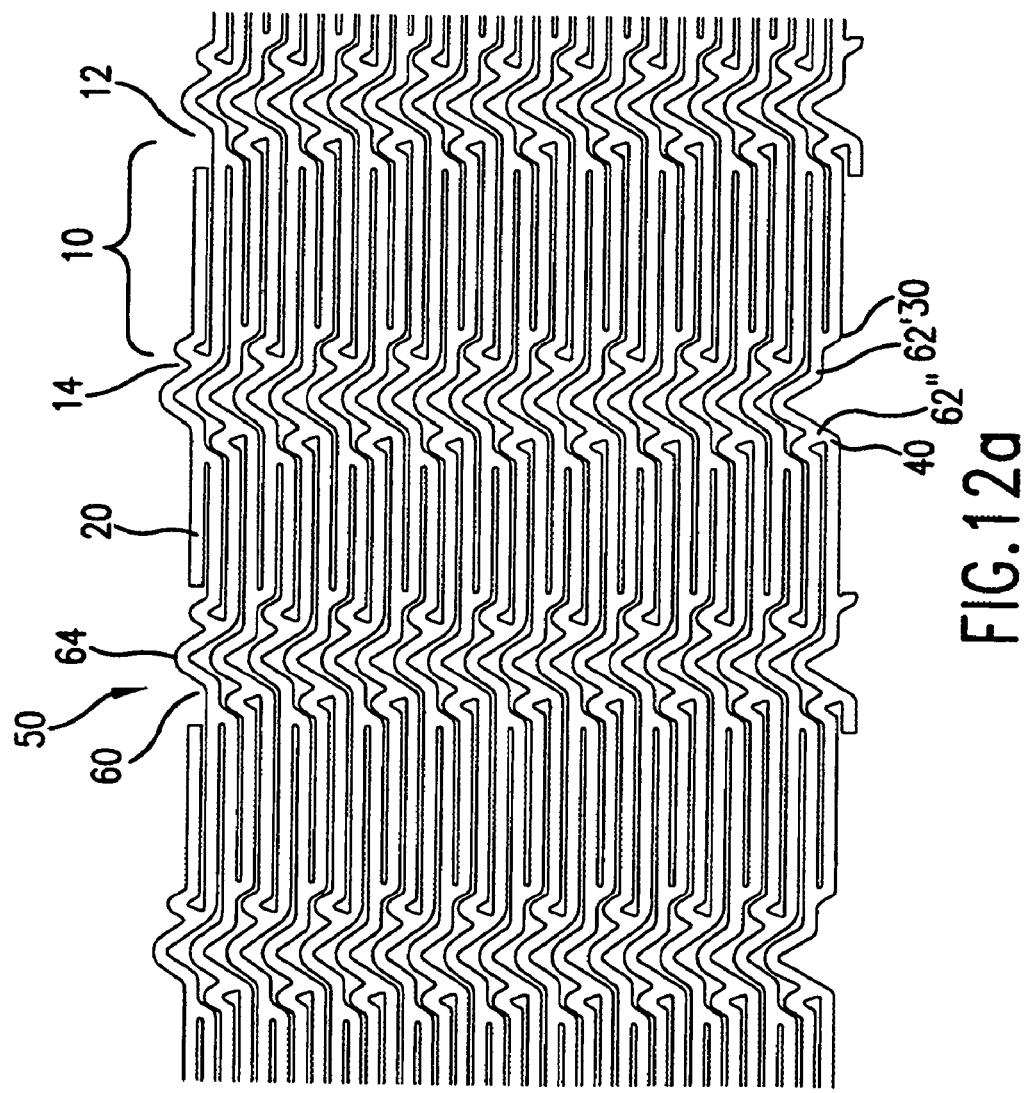
Figure 12B:
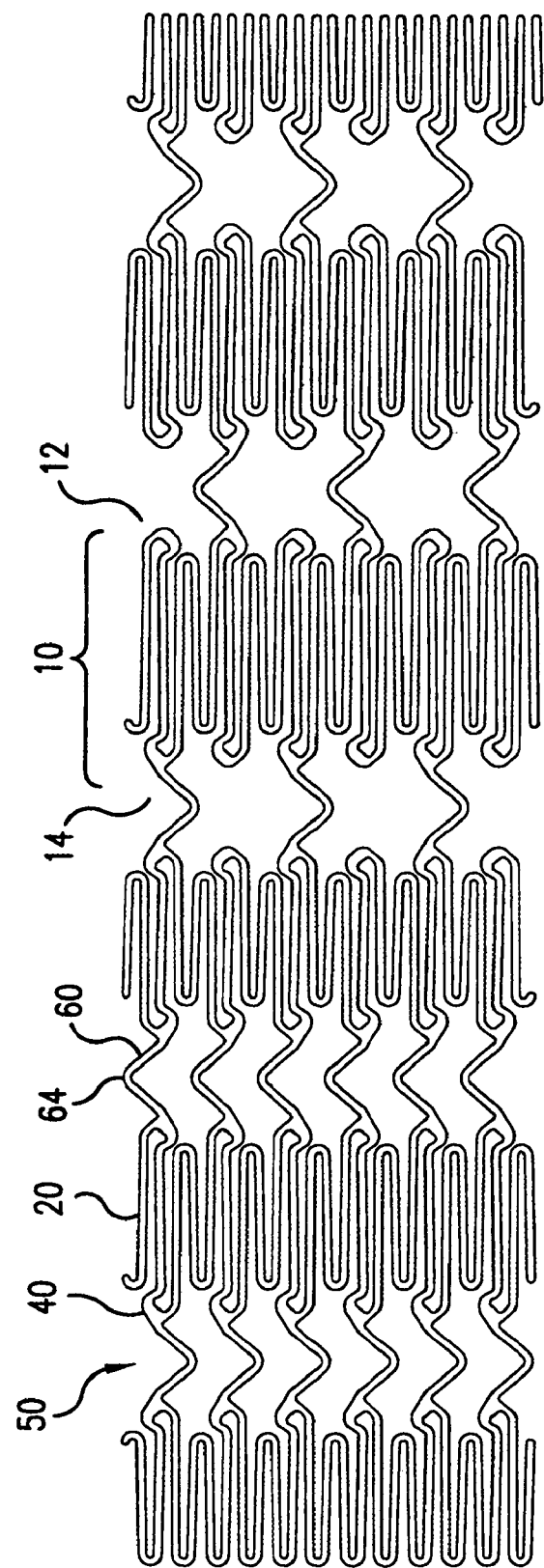
Figure 28:
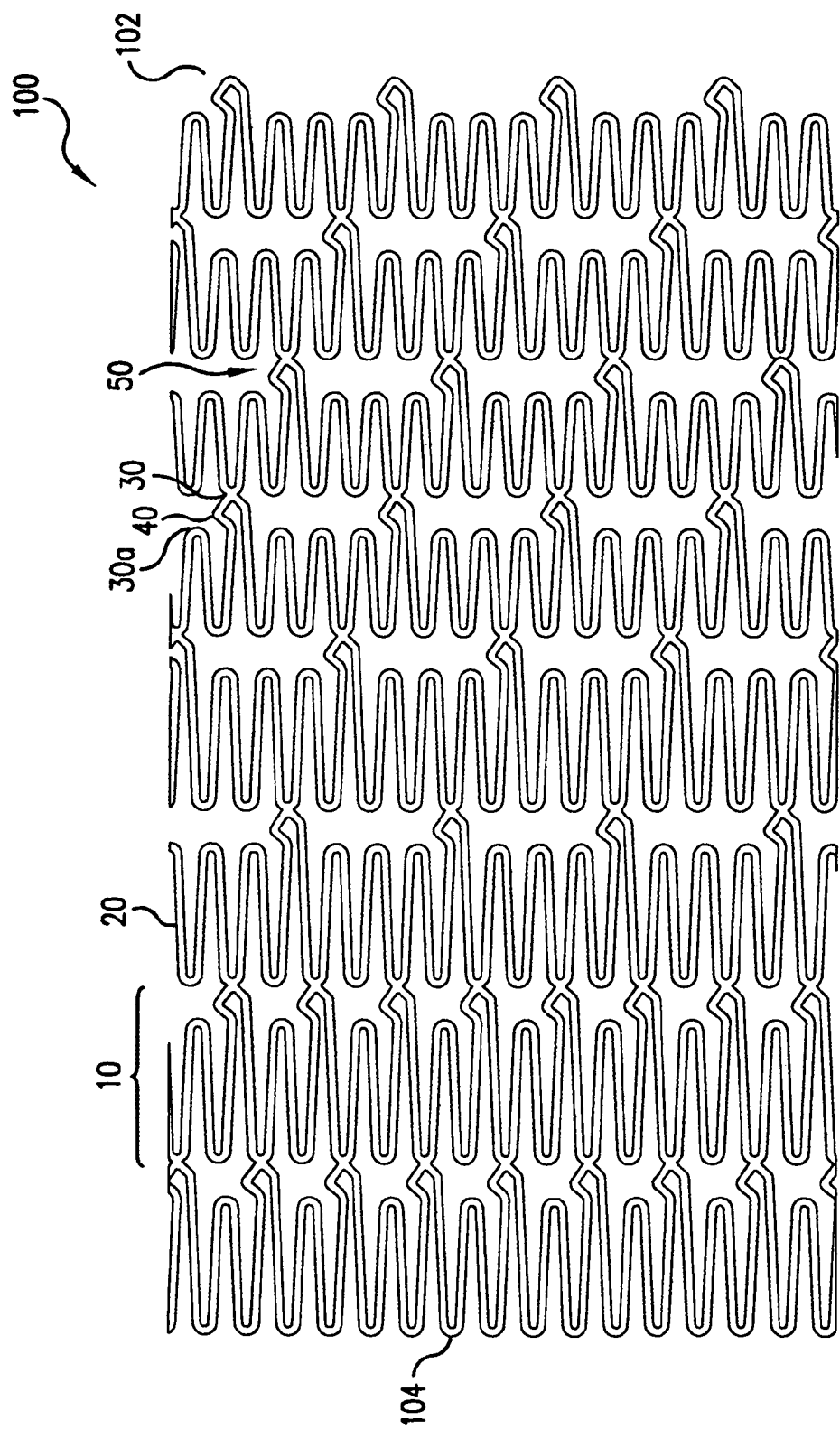
FIG. 28 shows a representative embodiment, in planar format, of an endoprosthesis configured to have varied characteristics along its length.

Similarly, the radial bias or rigidity of each annular element can be controlled or varied by altering the shape or size of the strut members. For example, radial bias or rigidity of an annular element, when deployed, generally can be increased by decreasing the length or by modifying the cross sectional profile of selected strut members of the annular element. It therefore is possible to provide an endoprosthesis in accordance with the present invention having varied radial bias or rigidity along its length by providing one annular element with a radial bias or rigidity that is different from the radial bias or rigidity of another annular element as shown in FIGS. 12b and 28 and described further below. In a similar manner, it is possible to provide an endoprosthesis having a tapered or flare shape formed of adjacent annular elements having different cross profiles when in the deployed configuration but similar or uniform radial bias or rigidity along its length.

Further in accordance with the present invention, and as previously noted, at least one annular element includes a foot extension extending between at least one pair of circumferentially-adjacent strut members. The foot extension can thus define an apex between the pair of circumferentially-adjacent strut members of the annular element. The foot extension includes a first foot portion extending circumferentially from an end of one of the adjacent strut members and a second foot portion extending circumferentially from a corresponding end of the other of the circumferentially-adjacent strut members. In combination, the first and second foot portions generally define an ankle portion, a toe portion, a base portion and a heel portion of the foot extension, which in combination define a generally circumferentially-directed apex.

With reference to the exemplary embodiment of FIG. 1, for illustration and not limitation, foot extension 40 extends between a pair 24 of adjacent strut members 20 of each annular element 10. As depicted for purpose of illustration, the foot extension 40 includes a first portion 41 extending circumferentially from an end 22 of one of the adjacent strut members 20, and a second portion 43 extending circumferentially from the corresponding end 22 of the other of the adjacent strut members 20. The juncture of the first and second foot portions 41, 43 defines a circumferentially-extending toe portion 48 of the foot extension 40. Similarly, and for purpose of discussion and not limitation, FIG. 1 shows that an ankle portion 44 is defined proximate the juncture of the first foot portion 41 with one of the circumferentially-adjacent strut members 20, and that a heel portion 42 is defined proximate the juncture of the second foot portion 43 with the other of the circumferentially-adjacent strut members 20. The toe portion 48 extends in a first circumferential direction a distance greater than the heel portion 42 of the foot extension 40 extends in an opposite circumferential direction. In the embodiment of FIG. 1, the entirety of the foot extension 40 extends in the circumferential direction of the toe portion 48. Furthermore, at least one of the first and second foot portions 41, 43 defines a base portion 46 at or proximate to the corresponding side 12 or 14 of the annular element 10. Defined generally within the boundary of the first and second portions 41, 43 is an open foot region 49 (see also, FIG. 2a).

A variety of configurations can be used for the foot extension in accordance with the present invention. For purpose of illustration and comparison with the foot extension of FIG. 1, exemplary embodiments of various alternative foot extension configurations are depicted in FIGS. 2a through 2e.

For example, the foot extension of the invention generally extends from the pair of circumferentially-adjacent strut members circumferentially at an angle relative to a line parallel to the longitudinal axis of the annular element. FIG. 1 shows a foot extension generally extending circumferentially at an angle of about 90 degrees relative to the longitudinal axis 15. However, the foot extension can be configured to extend circumferentially at an angle of less than 90 degrees relative to the longitudinal axis, as shown for example in FIG. 2a.

Additionally, FIG. 1 shows a foot extension 40, wherein the first foot portion 41 and the second foot portion 43 are generally parallel, straight elongate portions joined by curved portions. Particularly, the base portion 46 is defined by a generally straight portion and each of the toe portion 48, the ankle portion 44 and the heel portion 42 is defined by a curved portion. Each portion of the foot extension 40, as well as each of the circumferentially-adjacent strut members 20, has a substantially uniform width W and thickness in the embodiment of FIG. 1. In this manner, the circumferentially-adjacent strut members 20 will be substantially parallel to the longitudinal axis 15 and to each other, and region 49 will be substantially closed when in the delivery configuration. As depicted in FIG. 1, the foot extension 40 will thus generally define at least two areas of flexure between the pair of circumferentially-adjacent strut members 20; that is, one at the heel portion 42 and one at the ankle portion 44. An additional, or alternative, area of flexure can be defined at the toe portion 48 if desired to facilitate further expansion between the pair of circumferentially-adjacent strut members 20, such as to define a three point hinge configuration.

Figure 2A:
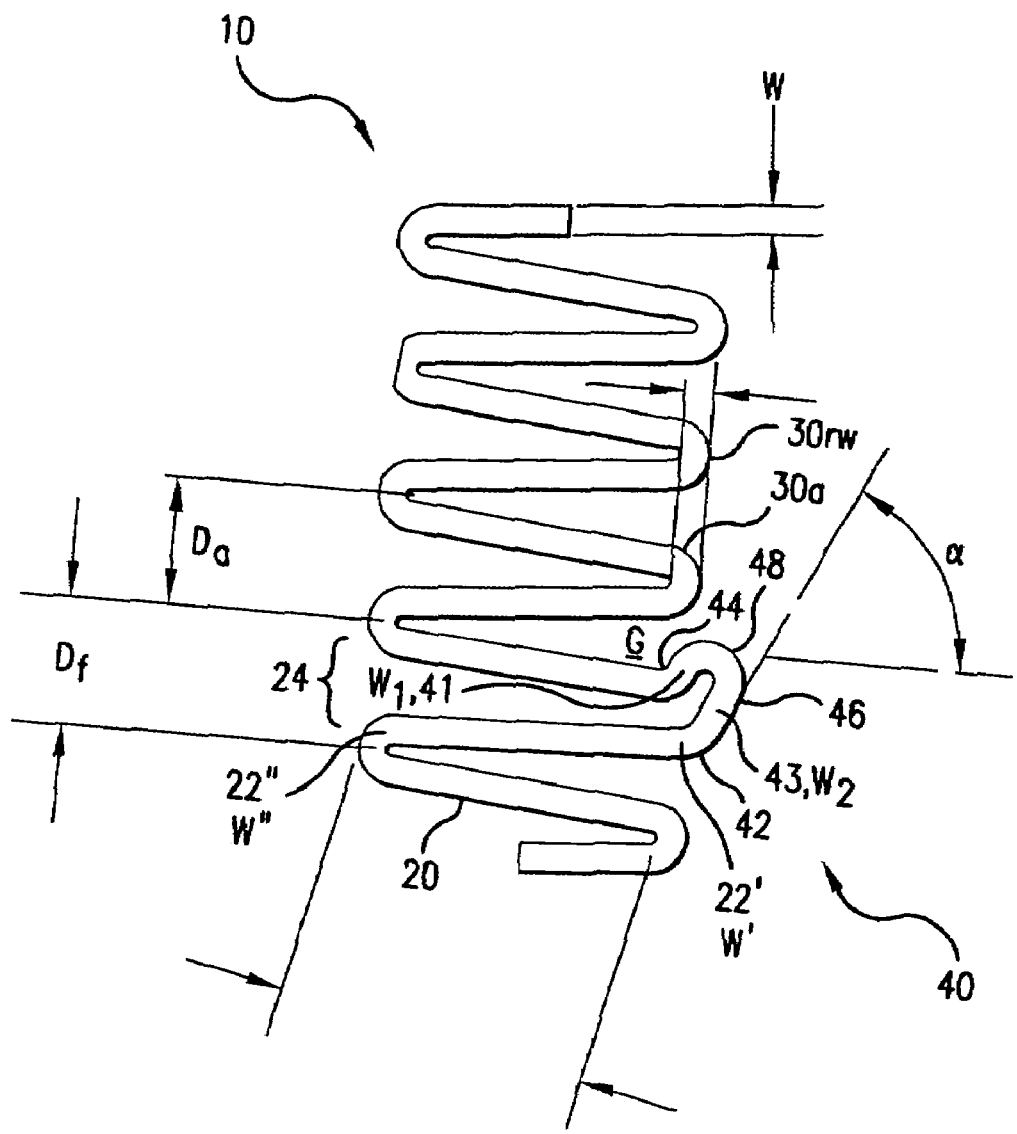
FIGS. 2a through 2e show detail views, in planar format, of various exemplary foot extensions in accordance with the present invention.

FIG. 2a depicts a preferred embodiment of a foot extension similar to that of FIG. 1. As previously noted, however, the foot extension 40 of this embodiment extends circumferentially at an angle alpha less than 90 degrees relative to the longitudinal axis 15. Additionally, the first and second foot portions 41, 43 are generally parallel but spaced apart to define a relatively more open region 30 than that of the foot extension of FIG. 1. To control expansion of the annular element, the width of the foot extension and circumferentially-adjacent strut members can be varied accordingly. For example, and as previously noted, circumferentially-adjacent apices along each side of the annular element 10 are spaced apart by a circumferential distance D, wherein the distance D generally increases as the annular element is expanded. It is often desirable to balance an annular element so as to expand uniformly, wherein the distance D increases a similar amount and at a similar rate between each pair of circumferentially-adjacent apices. Due to the increased flexure facilitated by the foot extension similar of FIG. 1, the distance Df between the circumferentially-adjacent apices located at the end of the pair 24 of circumferentially-adjacent strut members 20 opposite the foot extension 40 can increase to an extent or at a rate greater than the distance Da between other circumferentially-adjacent apices of the annular element. By providing the first and second foot portions 41, 43 of the foot extension with an average width greater than the average width of the circumferentially-adjacent strut members 20, as shown in FIG. 2a, the expansion between the circumferentially-adjacent apices 30 can be controlled or even balanced if desired. For example, and as shown in FIG. 2a, the first and second foot portions 41, 43 can be provided with a substantially constant width. Alternatively the first foot portion 41 can be provided with a width W1 different than that W2 of the second foot portion 43.

As previously noted with regard to the exemplary embodiment of FIG. 1, the circumferentially-adjacent strut members 20 and the different portions of the foot extension 40 can be provided with a substantially uniform width and thickness throughout. If the foot extension is provided with an increased width, it may be desirable or necessary to distribute stress or eliminate stress concentrations in the pair of circumferentially-adjacent strut members 20. As embodied in FIG. 2a, at least one or both strut member 20 of the pair 24 of circumferentially-adjacent strut members can be provided with a varied width. For example, and as shown in FIG. 2a, each strut member of the pair 24 of circumferentially-adjacent strut members can be tapered from a first width W' substantially similar to or even greater than that of the foot extension at the first end 22' of the strut member to a second width W" substantially similar to or even greater than that of the adjacent strut member 20 connected at the second end 22".

To further control expansion of the annular element, selected apices along the same longitudinal side 12, 14 of the annular element 10 as the foot extension also can be modified. For example, an apex 30 can be relaxed by reducing its width to facilitate greater expansion, or stiffened by increasing its width to facilitate less expansion. As shown in FIG. 2a, the width of selected apices 30rw are reduced to relax the apex 30 and thus control, such as balance, expansion of the annular element as needed or desired.

Furthermore, selected apices on the same side of the annular element as the foot extension can be configured to accommodate additional features. For example, and in accordance with another aspect of the present invention, it is desirable to enhance retention of a balloon expandable endoprosthesis on a balloon delivery system. As shown in FIG. 2a, the foot extension 40 extends in a first circumferential direction, and a circumferentially-adjacent apex 30a is located proximate the foot extension 40 in the first circumferential direction. When in the delivery configuration, this circumferentially-adjacent apex 30a is longitudinally aligned with, and preferably can substantially contact, the toe portion 48 of the foot extension so as to define a gap G between the circumferentially-adjacent strut members 20. Balloon material of the delivery system thus can be captured within this gap G, during crimping or through known heat treatment techniques, to enhance stent retention on a balloon. Additionally, or alternatively, a gap can be defined within an enlarged region 49 of the foot extension 40 for similar stent retention purposes if desired.

Figure 2B:
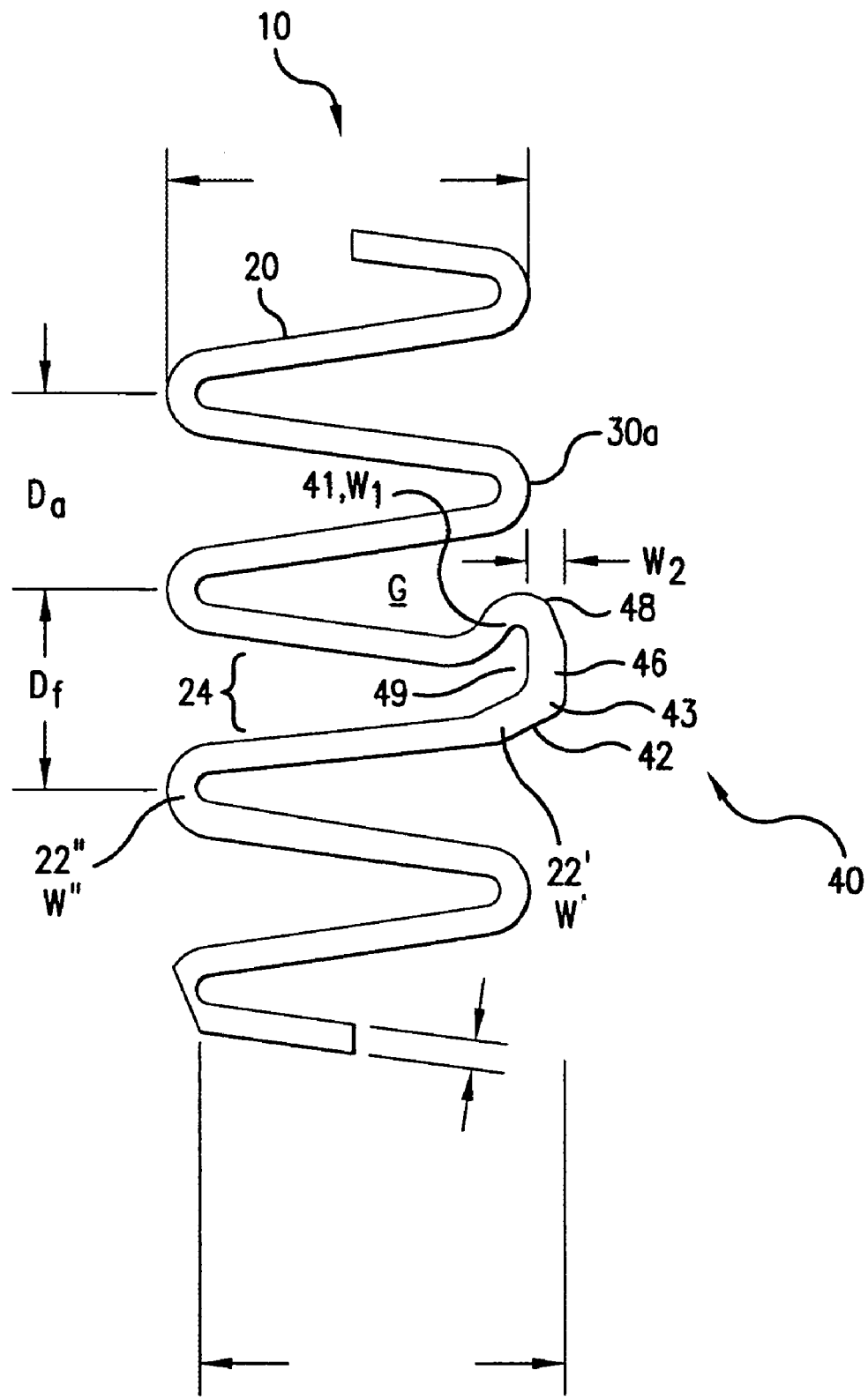

FIG. 2b depicts yet another foot extension configuration in accordance with the invention. The first foot portion 41 of the foot extension 40 is generally angled relative to the second foot portion 43, rather than aligned in parallel as shown in FIG. 1. Additionally, the second foot portion 43 is generally V-shaped to define a base portion 46 extending substantially perpendicular to the longitudinal axis, but with a more angular heel portion 42 than that of FIG. 1. In this manner, the first and second foot portions define an enlarged open region 49 relative to that of FIG. 1. As with FIG. 2a, the embodiment of FIG. 2b includes a foot extension 40 having an increased average width and tapered circumferentially-adjacent strut members, as well as a longitudinally-aligned apex 30a circumferentially adjacent to the toe portion 48 of the foot extension 40 for enhanced retention on a balloon delivery system.

Figure 2C:
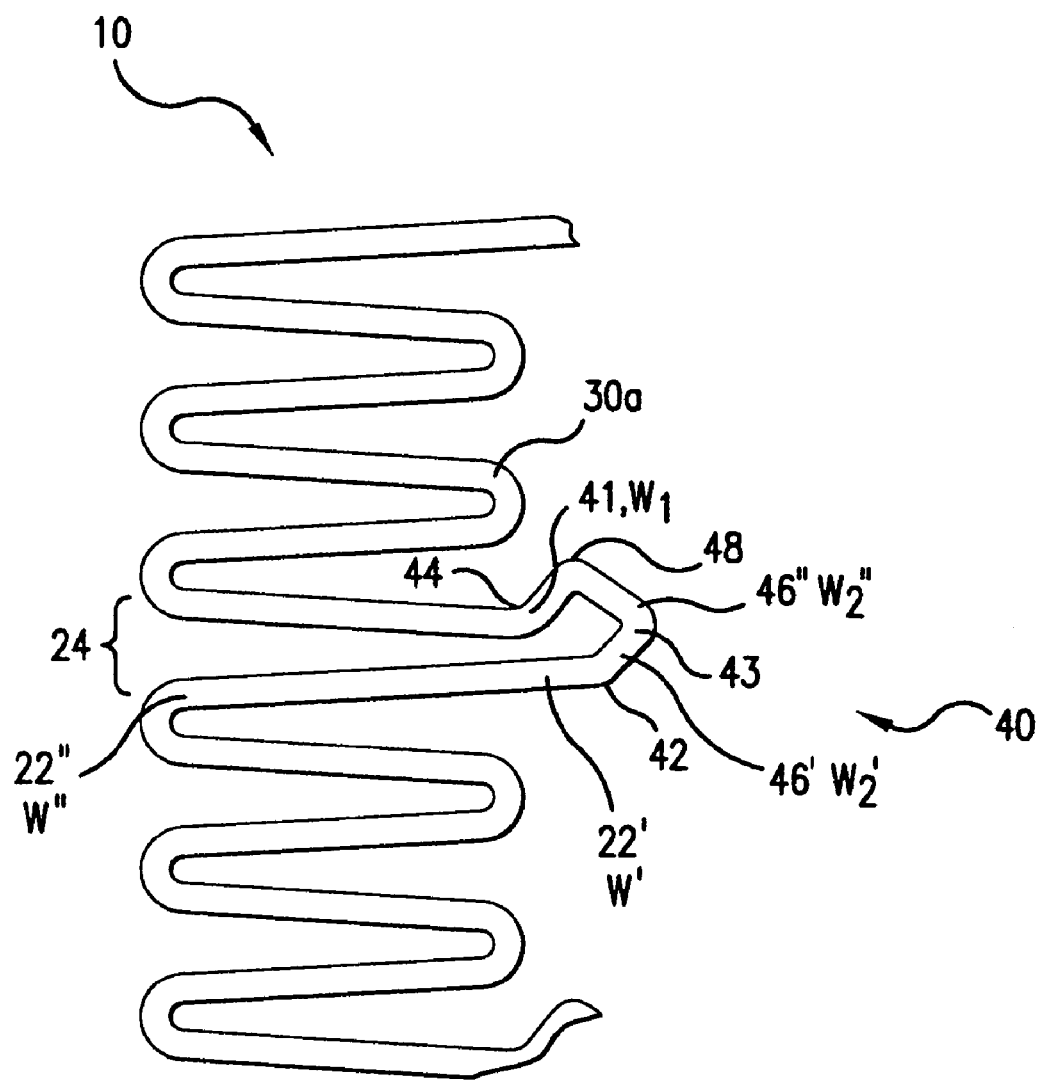

FIG. 2c depicts an alternative preferred embodiment of the foot extension of the present invention. The foot extension 40 of this embodiment is provided with a generally rectilinear configuration, including a first foot portion 41 extending from the ankle portion 44 to the toe portion 48 of the foot extension, and a second foot portion 43 extending from the heel portion 42 to the toe portion 48. Particularly, the second foot portion defines a contoured base portion 46, such as a generally V-shape including a first portion 46' and a second portion 46". In this manner, the foot extension can be configured to provide an additional area of flexure for expansion of the annular element if desired, as well as to define a connection location for longitudinally-adjacent annular elements as described further below.

As with the embodiments of FIGS. 2a and 2b, the first and second foot portions 41, 43 of FIG. 2c are provided with an increased width to stiffen the apex defined by the foot extension 40, and thus control, and more preferably, balance expansion of the annular element 10. For example, in one preferred embodiment, the width W1 of the first foot portion 41 and the width W2' of the first portion 46' of the V-shaped base portion are equal to each other, but different than the width W2" of the second portion 46" of the V-shaped base portion. Unlike the embodiment of FIGS. 2a and 2b, which are particularly advantageous in combination with a balloon delivery system, the embodiment of FIG. 2c does not include a longitudinally-aligned apex circumferentially adjacent the toe portion of the foot extension. Rather, and as recognized from FIG. 2c, at least the apex 30a located circumferentially proximate the toe portion 48 of the foot extension 40 is positioned longitudinally so as to mate with the foot extension when in the delivery configuration. For example, and as shown in FIG. 2c, this can be accomplished by providing at least one of the strut members 20 of the pair 24 of circumferentially-adjacent strut members with a length greater than the length of the remaining strut members of the annular element. The mating configuration between the foot extension 40 and the circumferentially adjacent apex 30a facilitates a reduced cross profile of the annular element 10 when in the delivery configuration. This embodiment is particularly advantageous for an endoprosthesis to be delivered within extremely small vessels, such as certain coronary or neurovascular vessels, or for an endoprosthesis that can be contained within a sheath during delivery, such as a self-expanding stent.

Figure 2D:
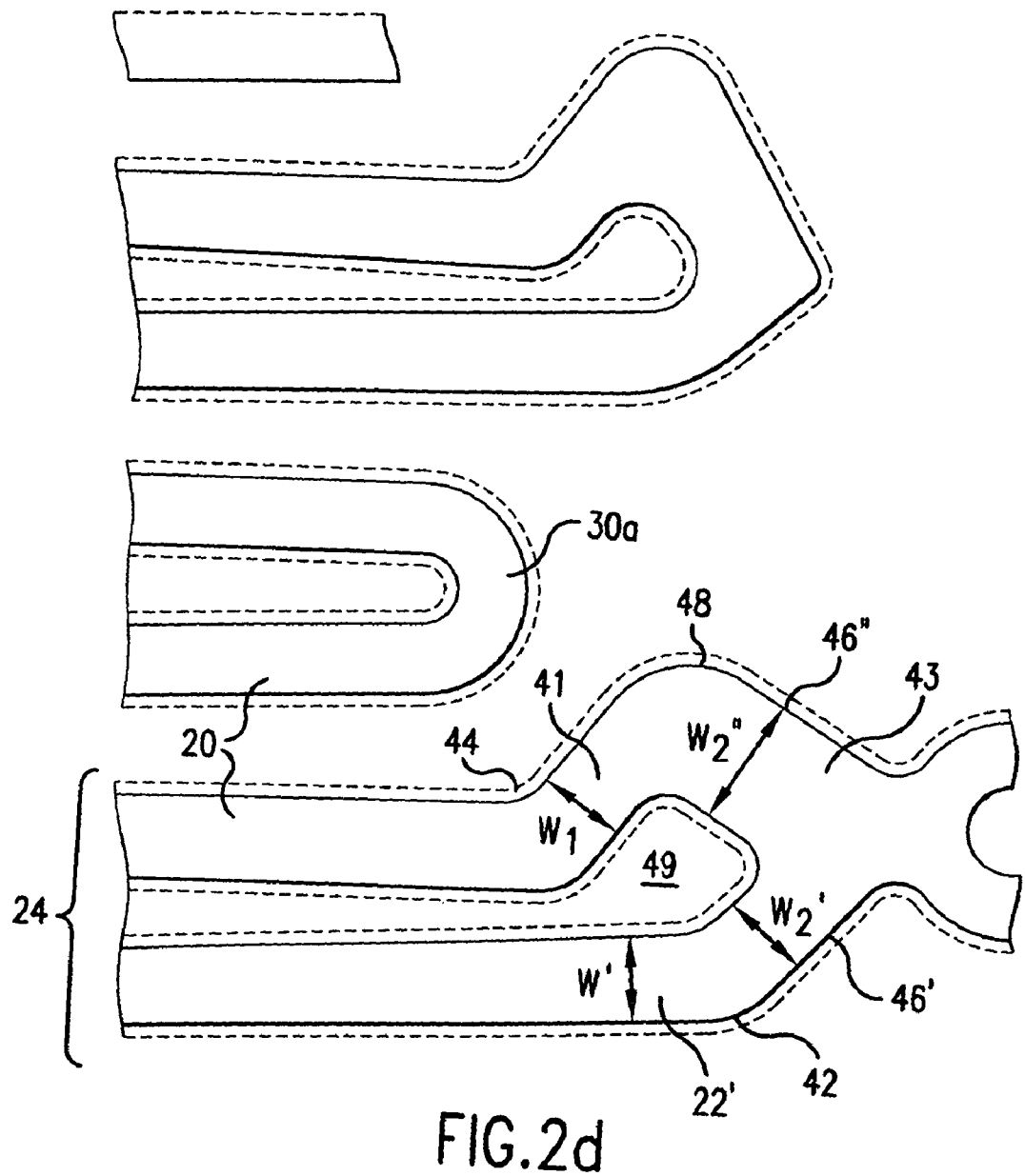

FIG. 2d is a enlarged detail view of a more rounded version of a foot extension similar to that of FIG. 2c, which is depicted with dashed lines for purpose of comparison. Particularly, FIG. 2d demonstrates the used of more rounded contours to shift or eliminate stress concentrations that may occur during expansion.

Figure 2E:
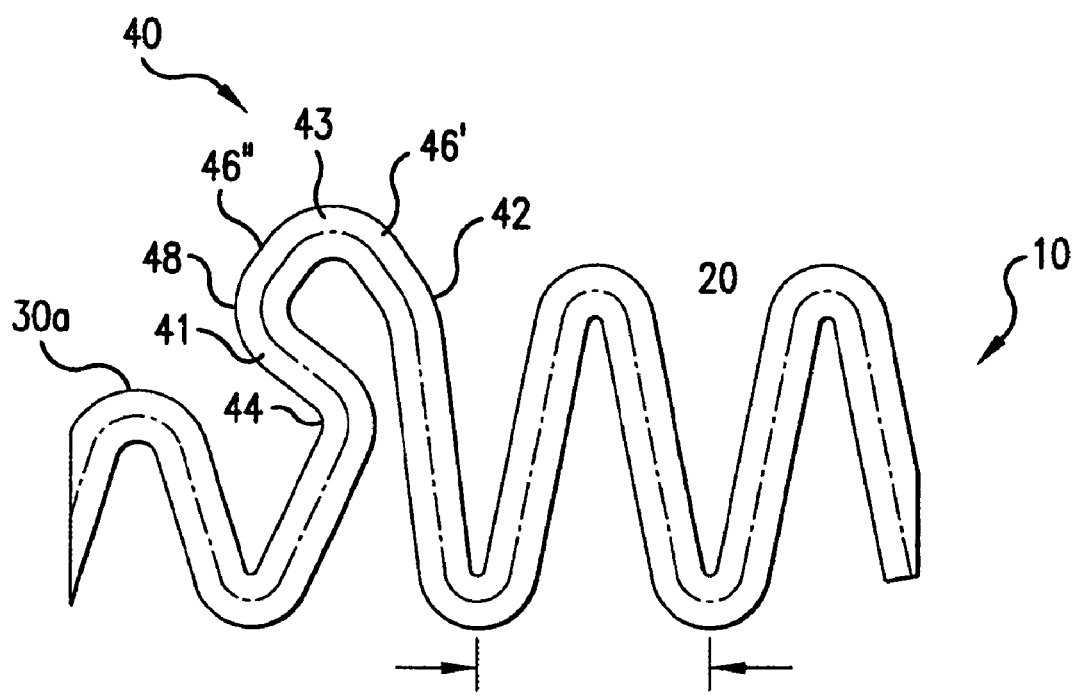

FIG. 2e depicts another alternative embodiment of a foot extension the present invention, which incorporates the mating configuration of the foot extension and the circumferentially adjacent apex as described with regard to FIG. 2c. Unlike the embodiment of FIG. 2c, however, the strut members 20 connected to the circumferentially adjacent apex 30a are provided with a length less than that of the remaining strut members so as to accommodate the desired mating relationship between the apex 30a and the foot extension 40. Furthermore, FIG. 2e shows that at least the circumferentially adjacent apex 30a is relaxed, such as by providing a reduced width, to open at a greater angle and thus compensate for the decrease of the distance D that would otherwise result during expansion due to the reduced length of the corresponding strut members 20. As previously described, expansion of the annular element 10 thus can be controlled, and more preferably, balanced. The strut members 20 having a reduced length and the circumferentially-adjacent apex 30a also can be provided with a reduced width if desired as shown in FIG. 2e.

Additional variations of the foot extension are also contemplated. For example, the heel portion of the foot extension can extend in a circumferential direction opposite from the toe, but preferably by a distance less than the distance over which the toe extends in the first direction.

Figure 8:
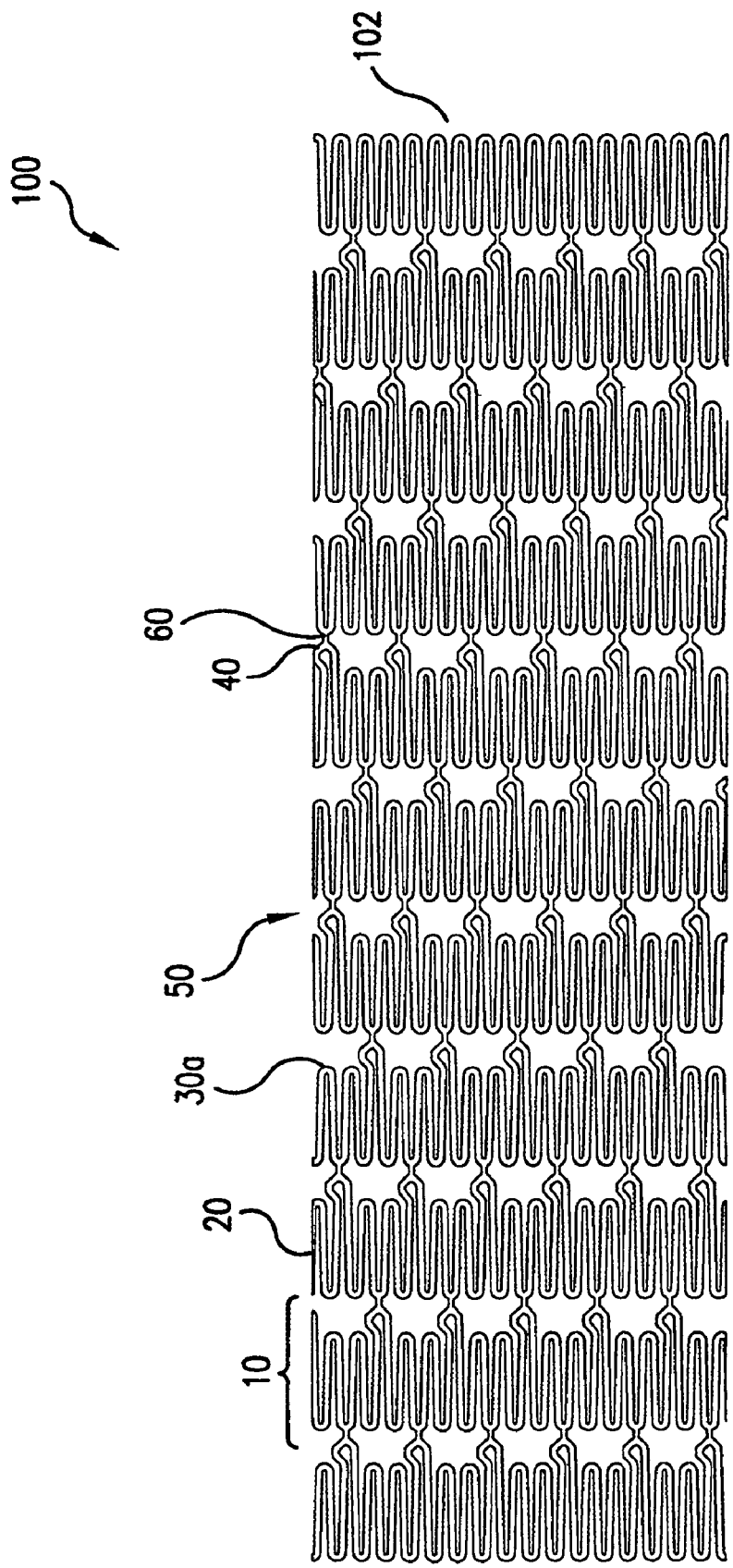

Any suitable number of foot extensions can be provided on an annular element in accordance with the present invention. A single foot extension can be provided on an annular element if desired. As shown in the embodiment of FIG. 1, however, it is preferable to define a plurality of apices of an annular element with foot extensions 40, wherein each foot extension extends between a pair 24 of circumferentially-adjacent strut members. The foot extensions can be provided on both longitudinal sides 12, 14 of the annular element 10 as shown in FIG. 1, or only on a single side of an annular element as shown in FIG. 8. Additionally, and as further shown in FIG. 8, it is possible to combine an annular element having one or more foot extensions with another annular element having no foot extension if desired. The plurality of foot extensions, if provided, can all extend in the same circumferential direction, or in opposite circumferential directions if desired. For example, and as shown in FIG. 1, the foot extensions on one longitudinal side of each annular element can extend in one direction circumferentially 17, whereas the foot extensions on the other side of the annular element extend in the opposite circumferential direction. In other embodiments, such as FIG. 6, all foot extensions 40 can extend in the same circumferential direction, either clockwise or counterclockwise when viewed from one end of the endoprosthesis, regardless of the longitudinal side 12, 14 of the annular elements 10 on which the foot extensions 40 are disposed.

Figure 4:
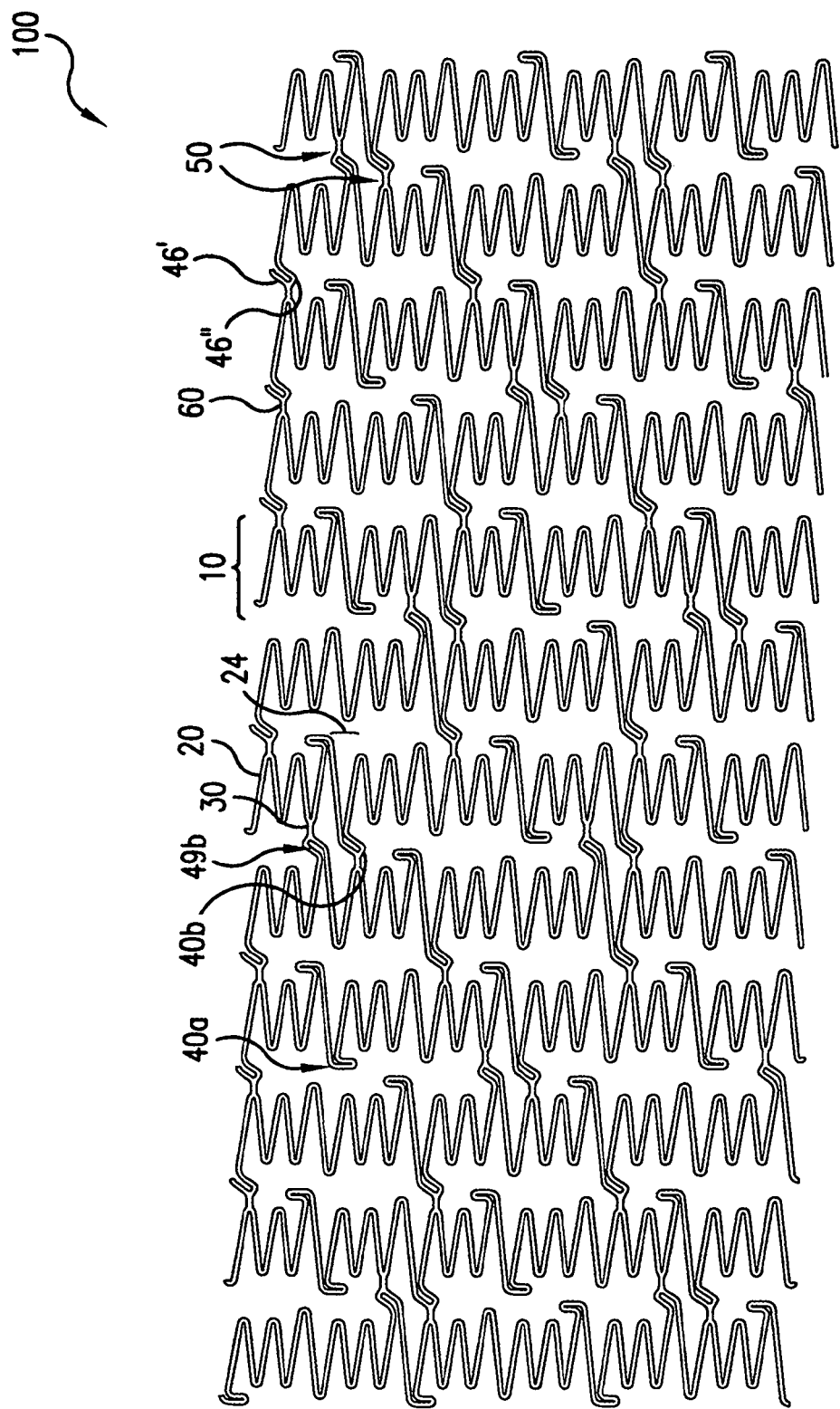

When a plurality of foot extensions are provided on an annular element, the foot extensions can be evenly spaced along the corresponding side of the annular element as shown in FIG. 1, or can be spaced in a staggered fashion as shown in FIG. 4. The number of apices that are not defined by a foot extension along the corresponding side of the annular element, and thus disposed between foot extensions, will depend upon the total number of apices desired for the annular element and the total number of such apices to be defined by a foot extension.

Further in accordance with the present invention, and as previously noted when a plurality of annular elements is provided, the first annular element and the second annular element are connected to each other at a connection location. A single connection location can be provided between two adjacent annular elements, or a plurality of connection locations can be provided as preferred. Furthermore, and as described below, the connection location can include one or more connectors extending between adjacent annular elements, or the connection location can be defined by an overlapping geometric pattern of two adjacent annular elements.

Preferably, the connection location includes a foot extension. As previously noted, each foot extension defines at least two areas of flexure. Such areas of flexure generally are located in the ankle, toe or heel portions of the foot extension. As such, the foot extension can facilitate greater longitudinal flexibility when included at the connection location between two adjacent annular elements. The multiple areas of flexure of the foot extension can also compensate for foreshortening when disposed at the connection location. As the annular element is expanded, the foot extension can be configured to open in a manner to adjust or compensate for some or all of the change that occurs in the longitudinal dimension of the annular element. That is, the foot extension can be configured to have a first longitudinal dimension when in the delivery configuration, and to straighten or retract, as deemed necessary, so as to have a second longitudinal dimension when in the deployed configuration. The difference between the first longitudinal dimension and the second longitudinal dimension of the foot extension preferably is substantially equivalent to the corresponding change in the longitudinal dimension of the annular element. Similarly, the foot extension can be stiffened by increasing the width of one or both of the first and second foot portions, or by otherwise altering the geometry of the foot extension in a suitable manner, to reduce the amount in which the foot extension opens, and thus reduce the extent of related foreshortening that occurs at the connection location.

Additionally, when located on a corresponding side between longitudinally-adjacent annular elements, the foot extension of one annular element includes a base portion generally facing the other annular element. The base portion provides an elongated region in which a connection location can be disposed, thus increasing versatility for design alternatives. For example, one alternative for increasing coverage provided by a stent is to configure corresponding zig-zag or sinusoidal patterns of longitudinally-adjacent annular elements less than 180 degrees out of phase with each other. That is, with the first side of a first annular element longitudinally adjacent the second side of a second annular element, it can be desirable for the apices proximate the first side of the first annular element to be circumferentially out of alignment with the apices proximate the second side of the second annular element. The foot extensions of the present invention allow such circumferential offset between longitudinally adjacent apices, even without the use of a connector. The foot extension of the present invention therefore enables greater axial flexibility, foreshortening compensation, radial expansion and coverage of the endoprosthesis.

With reference again to FIG. 1, a plurality of connectors 60 are provided to connect adjacent annular elements 10 at a plurality of connection locations 50. Each connection location 50 of FIG. 1 includes a foot extension 40 of one annular element and an apex 30 of another annular element, with a connector 60 having opposite ends 62 connected therebetween. If desired, however, the connection location 50 can extend from a foot extension to a foot extension, or from an apex to an apex, or to a strut member of one or both annular elements if desired. As embodied in FIG. 1, each foot extension 40 generally has a circumferentially elongated base portion 46 facing an adjacent annular element 20. With a connector 60 extending longitudinally from the base portion 46 of a foot extension 40 to an apex 30, the longitudinally-adjacent apices 30 of adjacent annular elements are circumferentially out of alignment. The foot base portions 46 at the longitudinal ends 102, 104 of the endoprosthesis 100 face outward from the remainder of the structure. Preferably, one or more foot extensions at either end 102, 104 of the endoprosthesis includes an area that undergoes minimal deformation or strain, such as the base portion 46, when expanded to the deployed configuration. A wire or strip of radiopaque material can be wrapped around or otherwise secured to this area of minimal strain so as to act as a radiopaque marker 120 for imaging purposes. Alternatively, a marker tab or eyelet can be attached at one or both ends of the endoprosthesis as described in detail with reference to FIG. 25, below.

Figure 11:
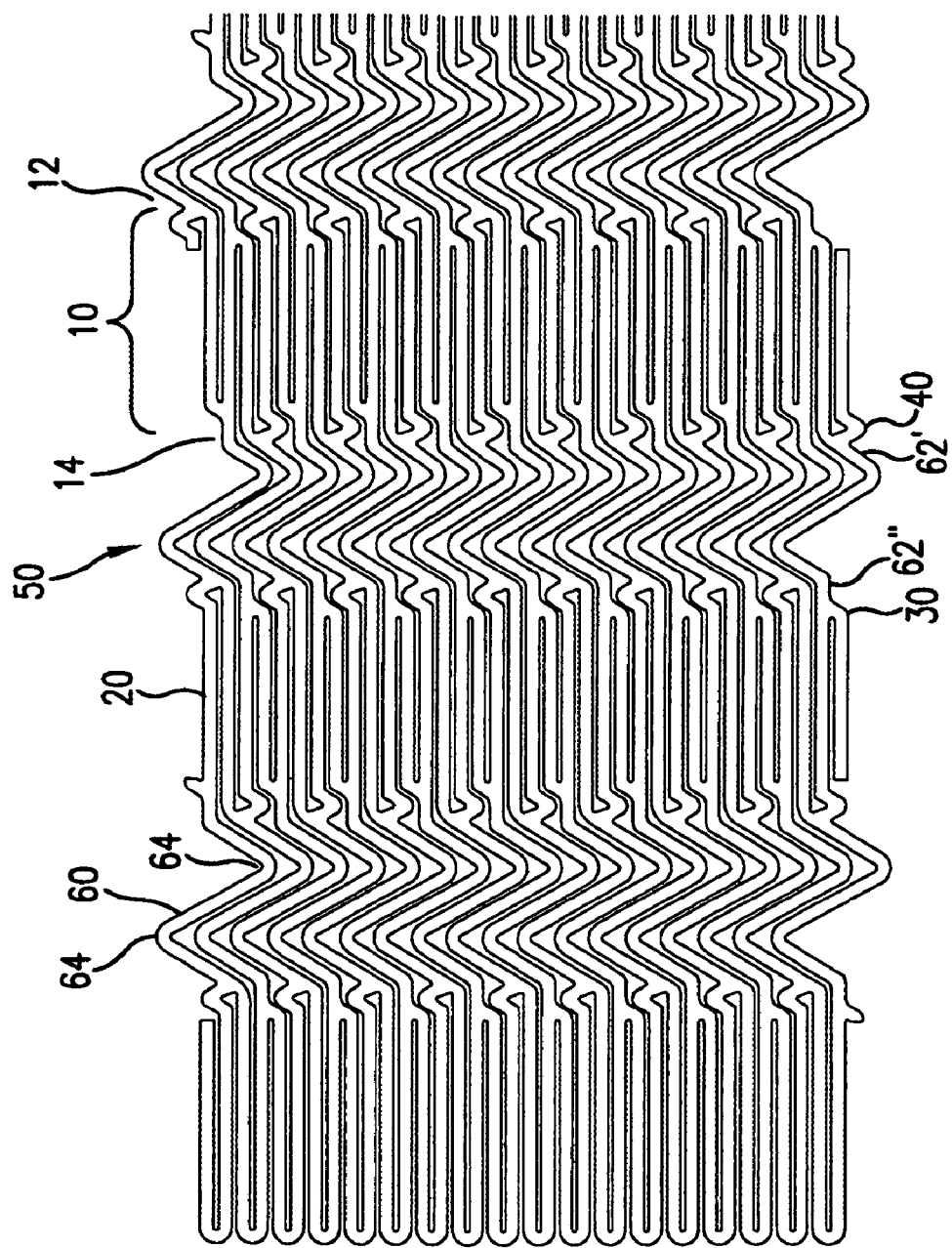
FIGS. 11 through 13 show detail views of various connector alternatives.
Figure 13:
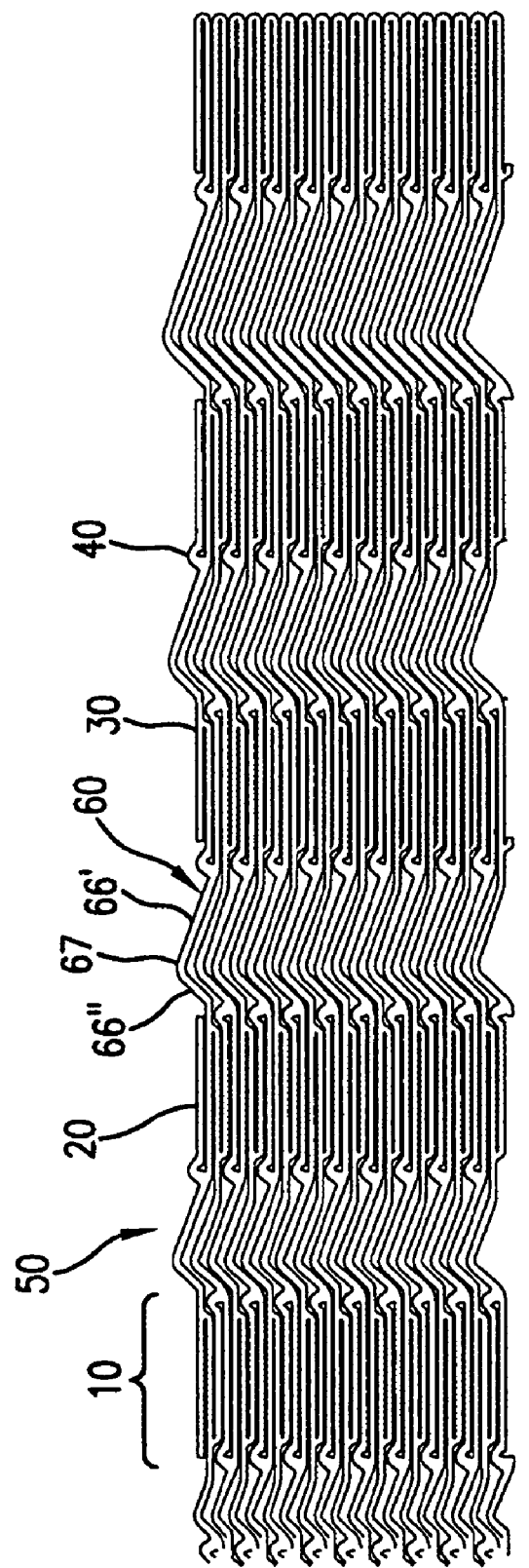

For simplicity and clarity, each connector depicted in FIG. 1 is a straight member. It is recognized, however, that the connector can be contoured or shaped to increase longitudinal flexibility if desired, as shown in FIGS. 11-13 and described further below. Similarly, the connectors need not extend parallel to the longitudinal axis, but can be aligned diagonally or helically such that the ends of the connector are circumferentially offset as shown for purpose of example in FIGS. 14b and 14d-14e.

A variety of design alternatives for different endoprosthesis embodiments can be achieved by selectively combining the various aspects of the present invention. For purpose of illustration and not limitation, a number of exemplary embodiments including the combination of connectors with foot extensions of the present invention are depicted in planar format in FIGS. 3-10. As with the embodiment of FIG. 1, the connectors are depicted as straight members for clarity and simplicity, but any connector configuration can be used as desired.

The connectors 60 may be constructed of the same or similar material of which the annular elements 10 are constructed of, or alternatively, the annular elements 10 may be constructed individually as described herein, wherein the connectors 60 are disposed at connection locations 50 thereby forming an endoprosthesis having more than one annular member. In this alternative embodiment, the connectors 60 may be constructed fully of a bio-absorbable material, partially of a bio-absorbable material or of a different material than that of the annular elements 10.

By forming the connectors 60 of a bio-absorbable material mechanical properties of the endoprosthesis can be tuned or adjusted accordingly. For example, a greater number of connectors 60 may be utilized to connect the annular rings 10 together, thereby providing greater column strength for delivery of the endoprosthesis. Once the endoprosthesis has been placed within a vessel or artery, the connectors 60 would then be absorbed thereby allowing each of the annular rings to move independent of one another. By having each of the annular rings 10 able to move independently of one another the flexibility of the endoprosthesis is greatly improved which may lead to a reduction of restenosis. It is further contemplated that individual connectors 60 may be constructed of different bio-absorbable materials, wherein pairs of connectors 60 or individual connectors 60 may be absorbed at different rates. Additionally, pairs of connectors 60 or single connectors 60 may be constructed of non-absorbable materials, wherein the absorbable connectors provide column strength during delivery of the endoprosthesis and the non-absorbable connectors provide connection points between the individual annular rings 10 thereby preventing the annular rings 10 from moving independently, though still providing increased flexibility of the expanded endoprosthesis from the reduction of connectors 60.

The bio-absorbable material of which the connectors 60 may be constructed of may be an inert material, a beneficial agent, or a combination of the two. An example of a suitable beneficial agent is described in U.S. Pat. No. 6,015,815 and U.S. Pat. No. 6,329,386 entitled "Tetrazole-containing rapamycin analogs with shortened half-lives", the entireties of which are herein incorporated by reference. It shall be understood that more than one beneficial agent may be combined with one or more inert materials to form the connectors 60. Examples of suitable bio-absorbable materials include Polygycolic acid (PGA), Polyhydroxybutyric acid, PolyL-Lactic acid (PLLA), Polydilactidel glycolide, Polydilactid acid, PolyDL lactide-co-gycolide.

Figure 2F:
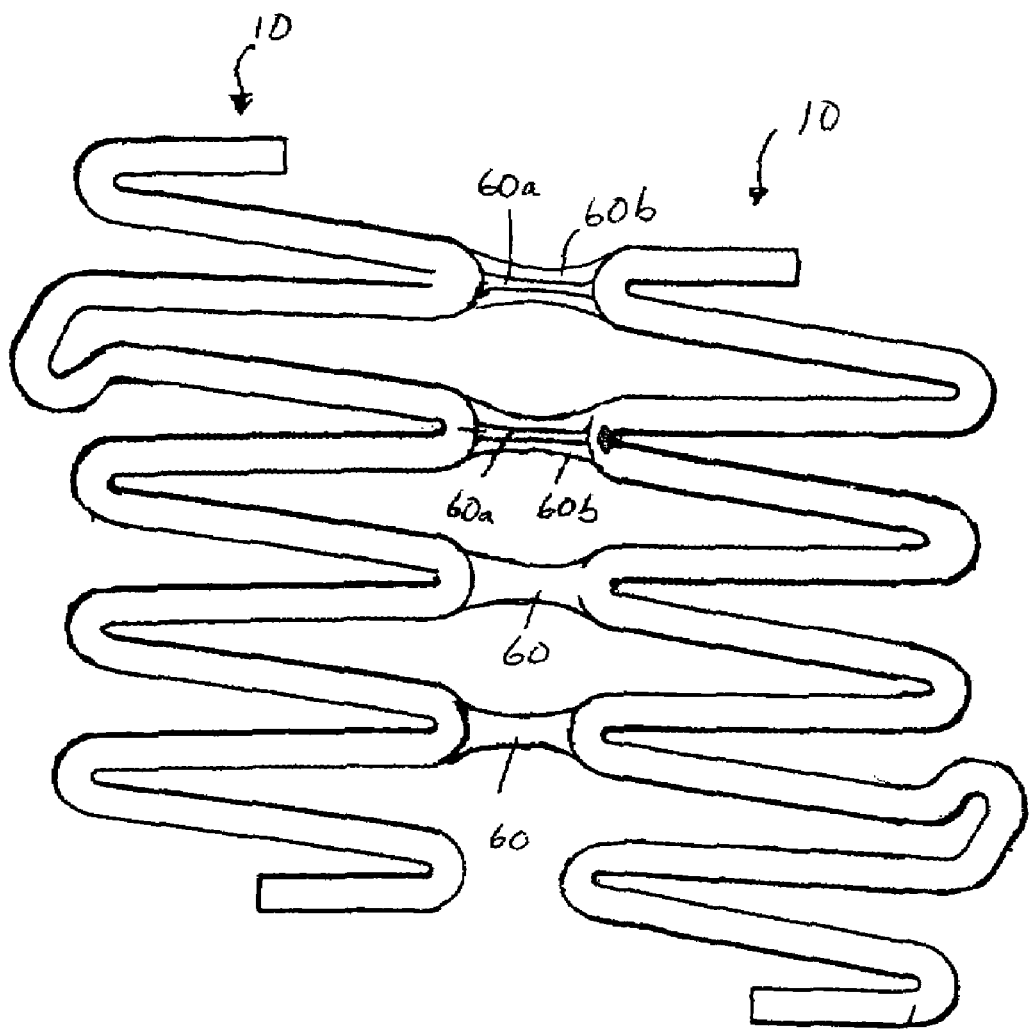
FIG. 2f is an exemplary embodiment of bio-absorbable connectors in accordance with the present invention.

Referring now to FIG. 2f there is shown an alternative embodiment of the connectors 60 in accordance with the present invention. As shown in FIG. 2f, the connectors 60 are provided to connect adjacent annular elements 10 at a plurality of connection locations 50. Each connection location 50 of FIG. 1 includes a foot extension 40 of one annular element and an apex 30 of another annular element, with a connector 60 having opposite ends 62 connected therebetween. If desired, however, the connection location 50 can extend from a foot extension to a foot extension, or from an apex to an apex, or to a strut member of one or both annular elements if desired. As shown in FIG. 2f, the connector 60 is partially constructed having a metallic member 60a and a bio-absorbable member 60b, wherein the bio-absorbable member 60b is disposed about the metallic member 60a. By producing the connector 60 in this manner, the column strength of the endoprosthesis is increased, thereby aiding in tracking and deployment, wherein the bio-absorbable material is then absorbed after deployment and expansion, thereby reducing the column strength of the endoprosthesis.

It may be desirable to choose a bio-absorbable material or materials that can be selectively activated to be made absorbable. For example, after expansion of the endoprosthesis within a vessel or artery, an activating agent may be delivered to the site of expansion, whereby the bio-absorbable connectors 60 are activated thereby becoming absorbable. By making the connectors 60 selectively absorbable, the stiffness and column strength of the endoprosthesis can be varied or altered as desired after implantation. For example, if greater flexibility is desired more connectors may be activated to be absorbed.

It is further contemplated that the bio-absorbable connectors in accordance with the present invention may be configured to be responsive to radio-frequency (RF) energy or ultrasonic energy, wherein the bio-absorbability of the connectors would be altered in response to applied energy. For example, the absorption rate may be increased or decreased in response to the applied energy; additionally it is contemplated that the connectors may be disconnected from the rings in response to applied energy. Suitable RF devices that may be utilized with the present invention include "The Crosser" from FlowCardia or the "Resolution" from OmniSonics Medical Technologies, Inc.

Figure 3:
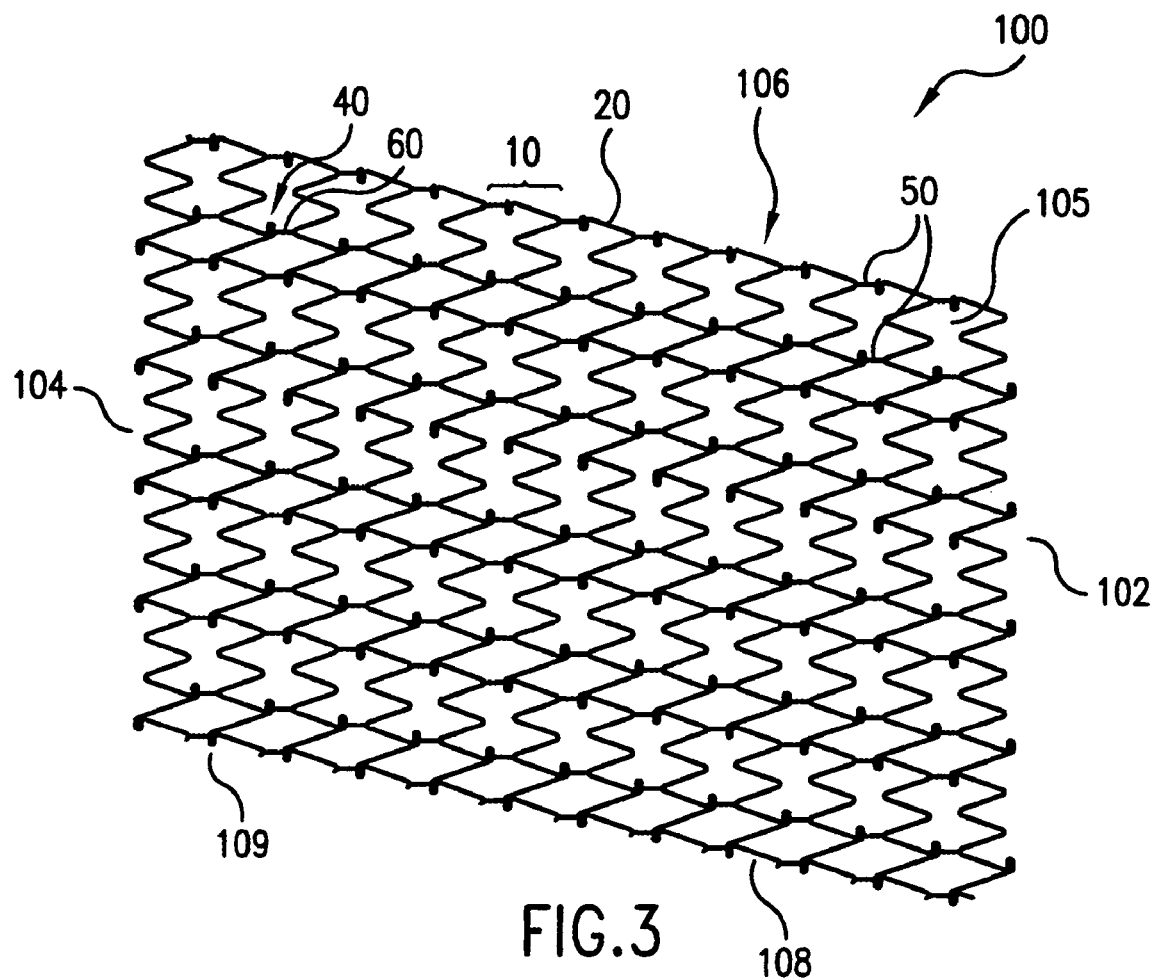
FIGS. 3 through 10 show alternative representative embodiments of the present invention in planar format, each of an endoprosthesis having annular elements connected at a plurality of connection locations by connectors.

The embodiment of FIG. 3, shown in a deployed configuration, is similar to that of FIG. 1, but includes a connector extending from each foot extension 40 of one annular element 10 to a longitudinally adjacent apex 30 of another annular element. As previously noted, the endoprosthesis of the invention can be formed as a rolled sheet or similar coiled structure if desired. As depicted in FIG. 3, complimentary lateral edges 106, 108 can be defined by providing connection locations 50 continuously in longitudinal alignment along the length of the endoprosthesis 100. Particularly, the connectors 60 and corresponding foot extensions 40 of the connection locations along the lateral edges 106, 108 define interlocking projections 109. The endoprosthesis 100 of this embodiment can be delivered in a contracted, coiled state to a deployment site with the lateral edges 106, 108 overlapping each other. Upon deployment, the endoprosthesis 100 will unravel from its coiled state, as well as expand circumferentially from its contracted state due to expansion of the annular elements. Once deployed, the interlocking projections 109 along the lateral edges will engage the "cells" 105 defined in the overlapping layer upon the application of a compressive force to prevent collapse of the endoprosthesis. A "cell" 105 is the opening formed between two circumferentially adjacent connection locations as defined by the closed boundary created by the interconnected struts, and the foot extensions and connectors as provided. Alternative arrangements can be used to define interlocking projections or, if the annular elements are provided with sufficient radial bias or rigidity, no interlocking projections need be provided.

The embodiment of FIG. 4, shown in a slightly deployed configuration, has free foot extensions 40a, which are longitudinally free from or unconnected to adjacent annular members, and connected foot extensions 40b, which are connected to adjacent annular members 10 with connectors 60. The free foot extensions 40a are aligned in the circumferential direction at an angle of about 90 degrees to the longitudinal axis and have substantially slit-shaped foot regions 49a. The connected foot extensions 40b have enlarged foot regions 49b, for greater radial expansion of the pair 24 of connected strut members, and extend circumferentially at an angle of less than 90 degrees from the longitudinal axis 15. The connection locations 50 are disposed at selected apices 30 and partway along the foot base portion 46. The foot base portions 46 of the connected foot extensions 40b have two portions 46', 46" oriented at an angle to each other to affect an area of flexure upon expansion.

One longitudinal side 12 or 14 of each annular element 10 has pairs of immediately adjacent connection locations 50. The other longitudinal side of each annular element 10 has connection locations 50 that are spaced from each other by a plurality of apices 30. Additionally, the foot extensions 40a, 40b are unevenly spaced along each annular element 10. Some strut numbers 20 have foot extensions at either end 22 thereof, other strut members 20 include a foot extension 40a, 40b only at one end, and yet others do not have a foot extension at either end.

Figure 5:
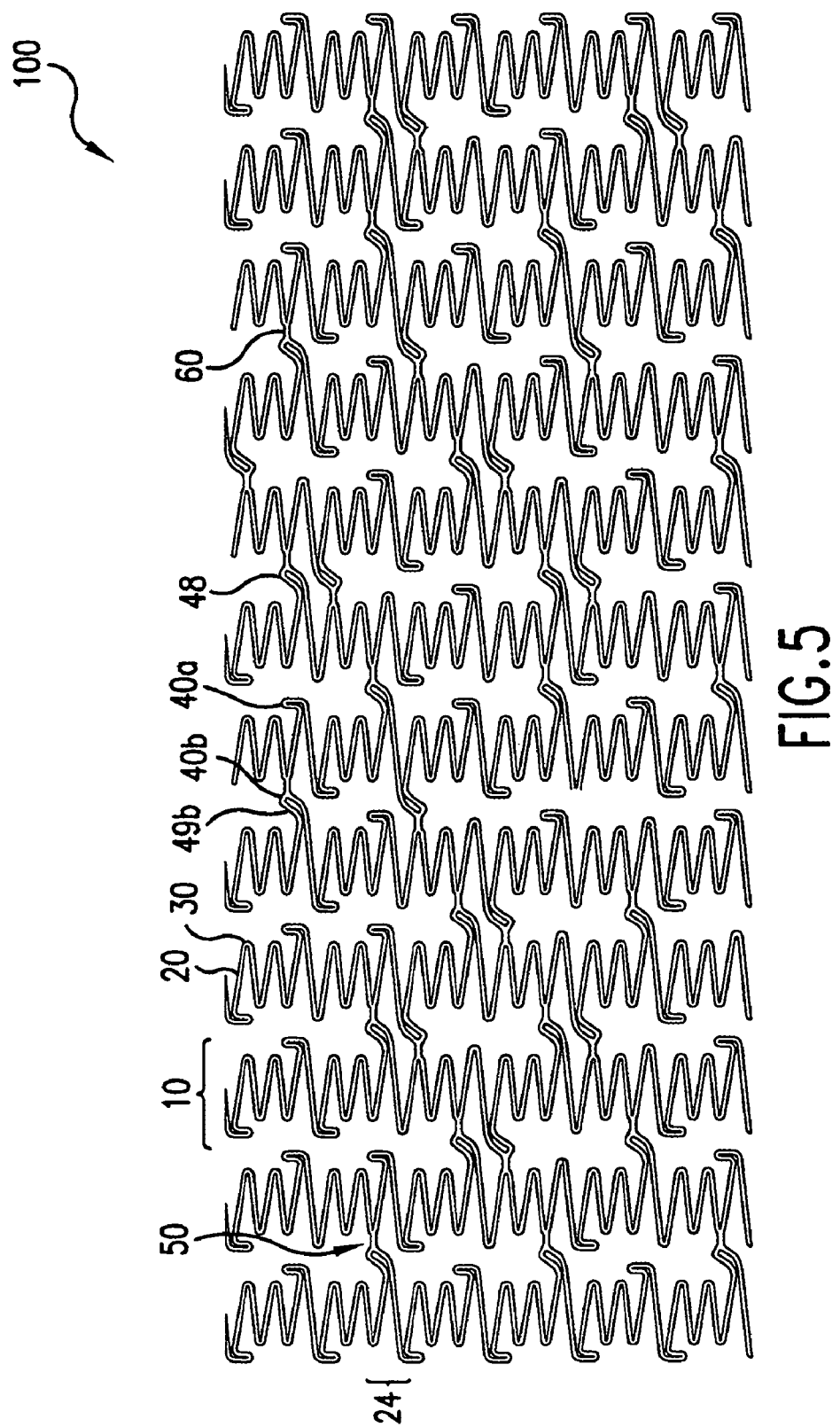

As with the embodiment of FIG. 4, the embodiment of FIG. 5 has connected foot extensions 40b with foot regions 49 that are significantly larger than the foot regions 49 of the free foot extensions 40a. In this embodiment as shown in a slightly deployed configuration selected apices 30 that are not defined by a foot extension protrude longitudinally more than other such apices for increased coverage. Additionally, the adjacent annular elements are substantially "in phase", such that longitudinally-adjacent apices of adjacent annular elements are circumferentially offset from each other. The circumferential extent of the connected foot extensions 40b allows the annular members to be connected in phase. Thus, the portion 48 of the connected foot members 40b preferably extends circumferentially at least or greater than the circumferential station of the connection location of the adjacent annular element 10.

Figure 6:
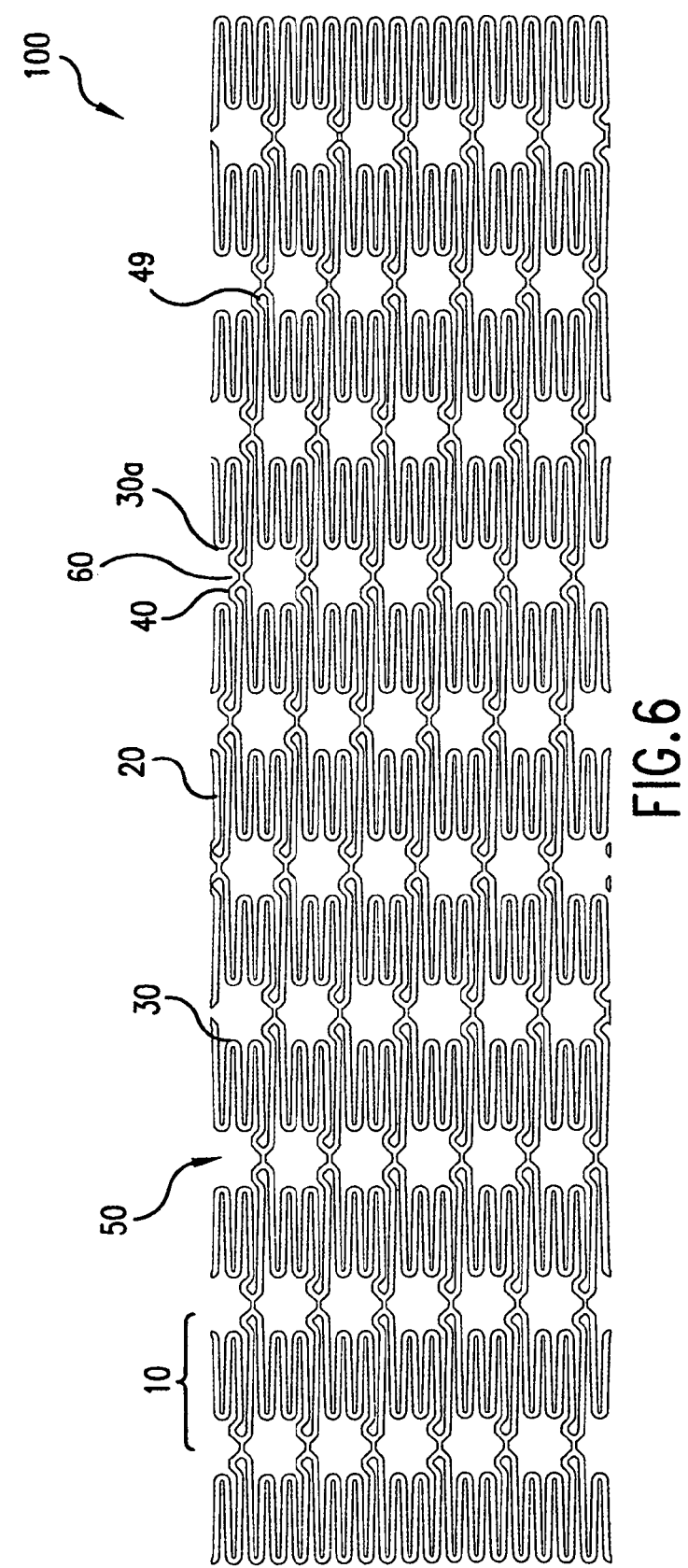
Figure 7:
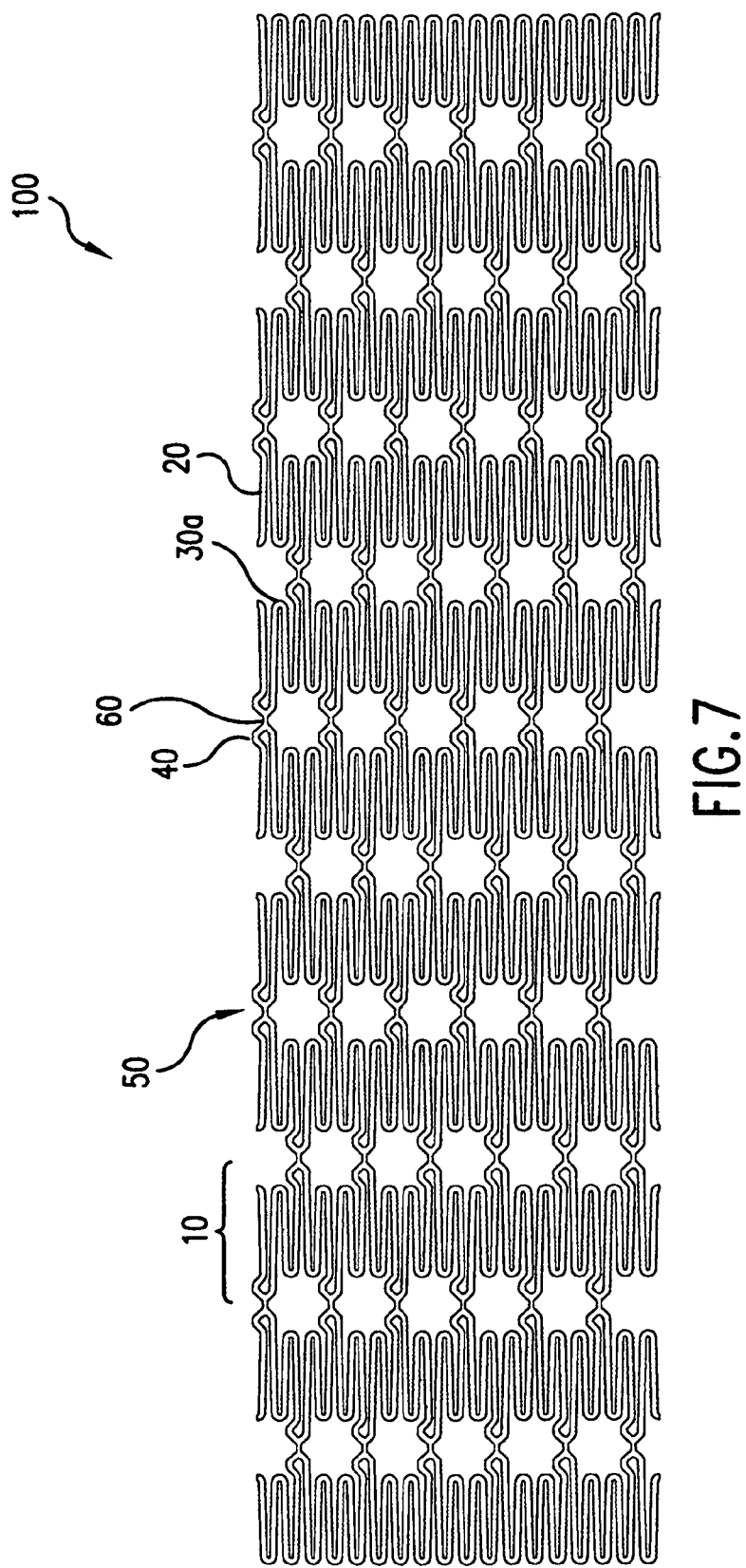

The embodiment of FIG. 6 includes opposing and connected foot extensions 40 with substantially open foot regions 49. In the delivery configuration shown in FIG. 6, each apex 30a that is circumferentially-adjacent a foot extension 40 is positioned to mate with the foot extension in a manner similar to that of FIG. 2c. Also, when in the delivery configuration, the strut members 20 are substantially aligned with the longitudinal axis 15 as shown. The embodiment of FIG. 7 is similar to that of FIG. 6, except foot extensions 40 on each annular element 10 circumferentially spaced so as not to include two foot extensions on a single strut member 20.

In the embodiment of FIG. 8, which is shown substantially in the delivery configuration, the foot extensions 40 are disposed only on one longitudinal side of each annular element 10. Preferably, all the foot extensions extend in the same longitudinal and circumferential directions. It is noted that connection locations 50 are evenly spaced circumferentially, with two unconnected apices 30 between circumferentially adjacent connection locations. Each connection location 50 includes a foot extension 40 on one annular element 10 and an apex 30 on the adjacent annular element 10. Furthermore, the connection locations 50 between adjacent annular elements 10 are circumferentially offset from one set of connected annular elements to the next.

Figure 9:
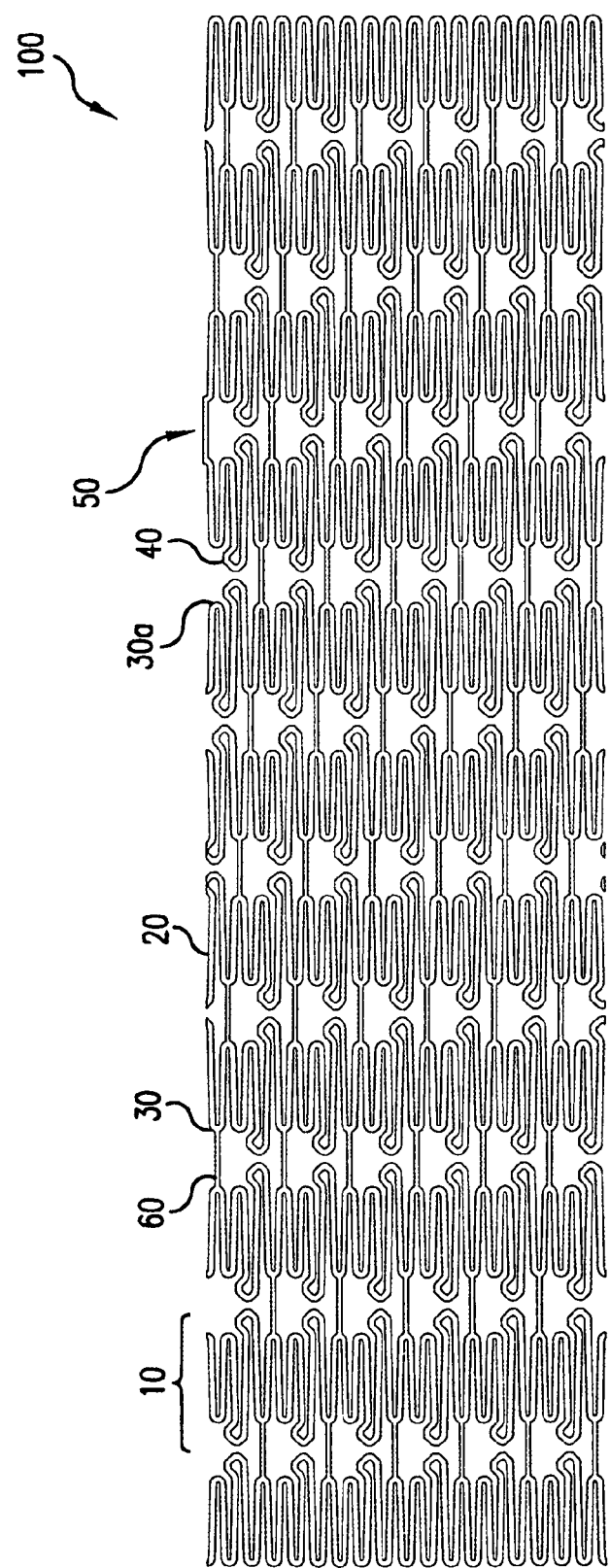
Figure 10:
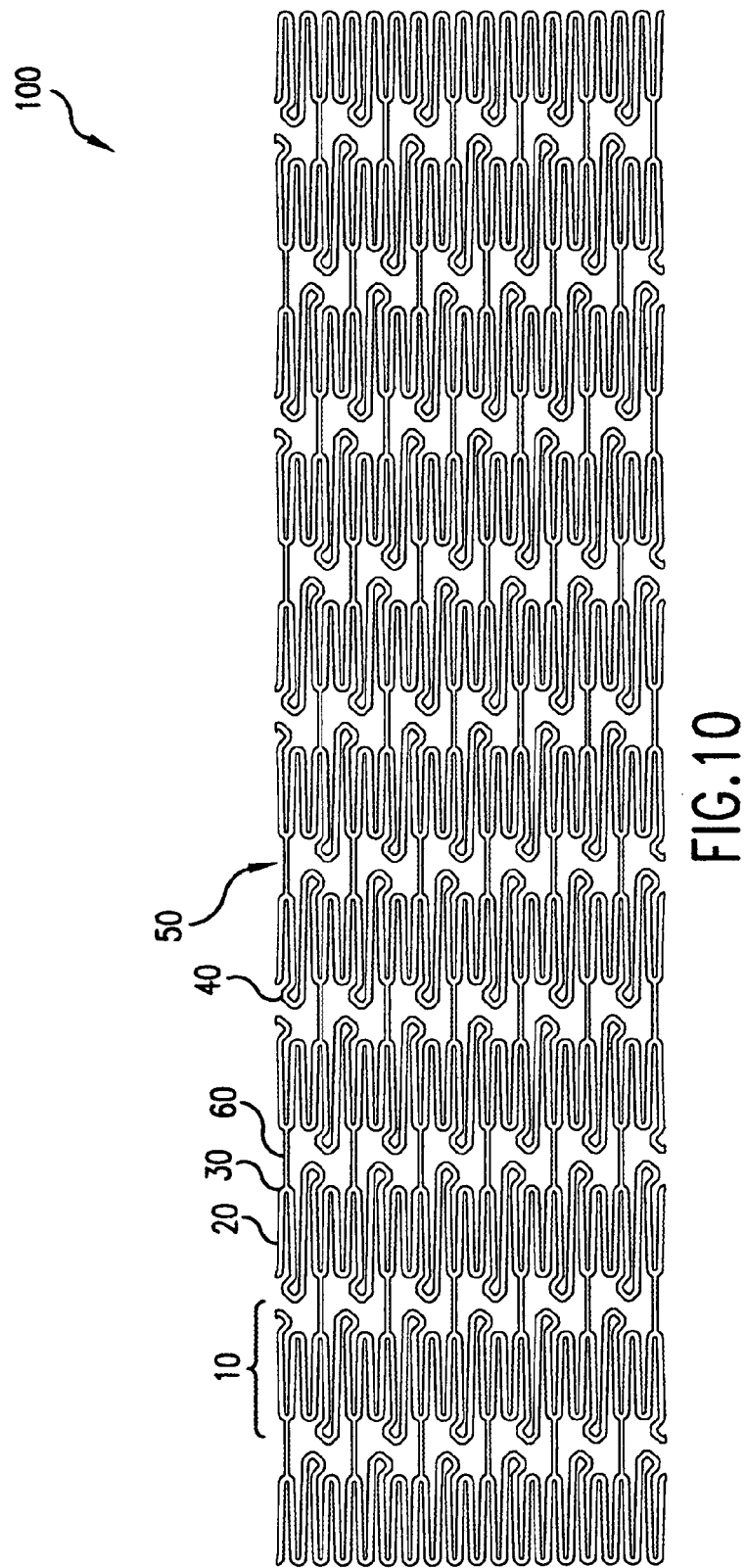

FIGS. 9 and 10 depict alternative embodiment in the delivery configuration, wherein connection locations 50 include connectors 60 extending between apices 30 not defined by foot extensions. All of the foot extensions 40 are free or unconnected. In FIG. 9, all foot extensions 40 extend in the same circumferential direction; in FIG. 10, the foot extensions 40 alternate between clockwise and counterclockwise directions.

As previously noted, FIGS. 1 and 3-10 depict various endoprosthesis embodiments that include a straight connector between adjacent annular elements for purpose of simplicity and clarity. It is understood, however, that alternative connector shapes can be used within the scope of the invention. For example, FIG. 11 shows an endoprosthesis in the delivery configuration, which includes a plurality of annular elements connected by substantially sinusoidal connectors 60. Each annular element 10 includes a plurality of interconnected strut members 20, wherein every other apex disposed along a longitudinal side 12 and 14 is defined by a foot extension 40. Each sinusoidal connector 60 extends between a foot extension 40 on one annular element and an apex 30 on an adjacent annular element. The sinusoidal connector includes curved portions 64 between the first and second ends 62', 62" of the connector 60. In this manner, the longitudinally-adjacent apices of adjacent annular elements can be arranged in circumferential alignment with each other (that is, 180 degrees out of phase) or out of alignment with each other, as preferred. FIG. 12a is directed to an endoprosthesis embodiment similar to that of FIG. 11, however, U-shaped connectors, each including a curved portion 64, are provided in lieu of the sinusoidal connectors. In a further embodiment of the invention, as shown in a slightly deployed configuration in FIG. 12b, an endoprosthesis is provided with a connector 60 between foot extensions 40 on longitudinally adjacent apices 30 of adjacent annular elements 10, in a manner similar to the embodiment of FIG. 6. At least one unconnected apex 30 is disposed between circumferentially adjacent foot extensions 40 on each side of the annular element 10. In this embodiment, however, each connector 60 has a U- or V-shape with at least one curved portion 64. If desired, the curved portions 64 can all extend in the same circumferential direction, as shown in FIG. 12a, or can alternate in circumferential direction from one set of adjacent annular elements to the next as shown in FIG. 12b. Furthermore, and as depicted in FIG. 12b, the number of connectors, and thus connection locations, between adjacent annular elements can be varied for varied longitudinal flexibility along the length of the endoprosthesis. In another preferred embodiment of the invention an endoprosthesis is provided with the sinusoidal shaped connectors between adjacent annular elements located proximate at least one region of the endoprosthesis as shown in FIG. 11, and with the U-shaped connectors between adjacent annular elements located proximate another region of the endoprosthesis, as shown in FIG. 12a.

In accordance with an additional aspect of the invention, and as shown in FIG. 13, an alternative connector 60 is provided having an L-shaped portion 66 between its first and second ends 62. The L-shaped portion has a first leg 66' and a second leg 66". A bend or circumferential peak 67 is provided between the first and second legs. Preferably, and as shown in FIG. 13, the length of the first leg 66' is different than that of the second leg 66". The width of the first leg 66' likewise can be different than that of the second leg 66", as shown if FIG. 13. It is preferred that the L-shaped connector be connected between adjacent annular elements 10, such that the first end 62' of the connector 60 is circumferentially offset from the second end 62" of the connector 60. FIG. 13 depicts the L-shaped connectors incorporated in an endoprosthesis embodiment similar to that of FIGS. 11 and 12, as shown in the delivery configuration, wherein all of the L-shaped connectors are arranged so as to extend circumferentially in the same direction, as defined by the direction in which the bend 67 of the L-shaped portion 66 extends.

The L-shaped connector of this aspect of the invention can be configured to compensate for foreshortening of the endoprosthesis upon deployment, without altering the angle between the first and second legs. That is, the L-shaped connector can be arranged so as to have a first longitudinal dimension when in the delivery configuration, and to rotate relative to the annular elements, as deemed necessary, so as to have a second longitudinal dimension when in the deployed configuration. The difference between the first longitudinal dimension and the second longitudinal dimension of the L-shaped connector preferably is substantially equivalent to the corresponding change in the longitudinal dimension of the annular element to be compensated upon deployment. Rotation of the L-shaped connector can be accomplished or enhanced by weakening the points of connection at either end of the connector with the corresponding annular elements. Furthermore, the degree of compensation, as well as longitudinal flexibility, can be varied by varying the length of the connectors as shown in FIG. 13.

FIGS. 14a through 14e show alternative arrangements of the L-shaped connector of the present invention as disclosed in U.S. patent application 60/379,593, which is incorporated in its entirety herein by reference. Particularly, and as shown in FIGS. 14a through 14e, a plurality of L-shaped connectors can be provided between adjacent annular elements 10 such that selected connectors 60 are arranged to extend circumferentially in opposite directions, as defined by the direction in which the bend 67 of the L-shaped portion is directed. In this manner, the strut members 20 of the annular elements 10 and the connectors form a generally repeating pattern defined by two different, alternating cell shapes. In each embodiment, however, it is recognized that the number of connectors and apices, as well as the dimensions of the components and the angle of alignment between the legs of the L-shaped portion and between the ends of the connector, can be varied to achieve desired characteristics of the stent such as scaffolding, coverage, and flexibility. Although not shown, one or more of the apices of each of these embodiments can be defined by a foot extension in accordance with the invention.

Figure 14E:
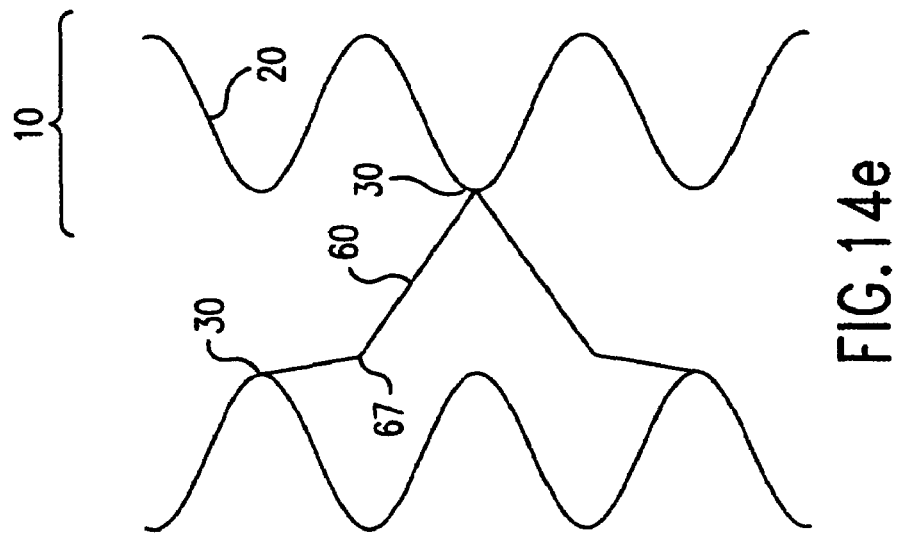
Figure 14D:
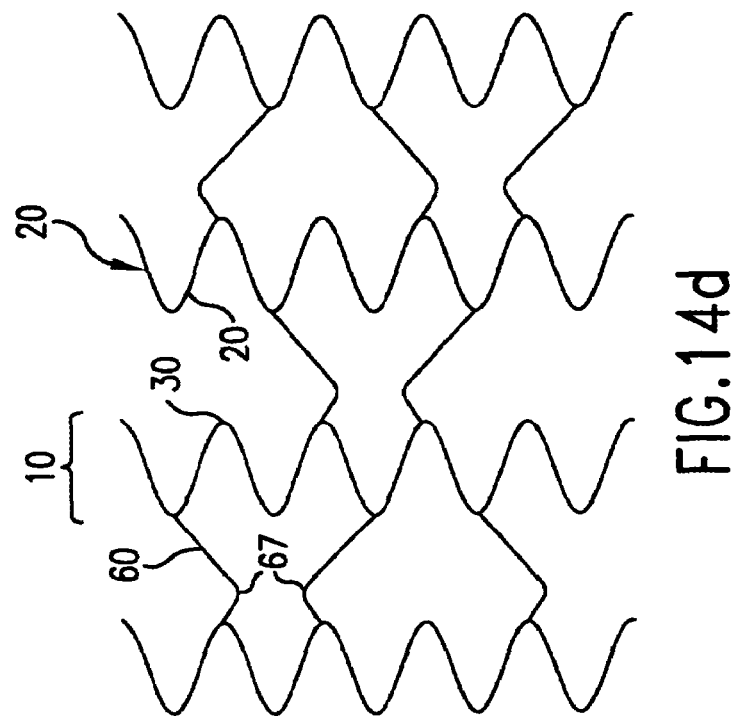

For example, FIG. 14a shows circumferentially adjacent L-shaped connectors extending in opposite circumferential directions, wherein each connector 60 is connected between longitudinally adjacent apices 30 of adjacent annular elements 10. FIGS. 14b and 14d show alternative embodiments of an endoprosthesis having L-shaped connectors, wherein the circumferentially-adjacent connectors 60 extend from circumferentially adjacent apices 30 on one annular element 10 to non-adjacent apices 30 on the other annular element 10. In FIG. 14c, the L-shaped connectors extend from respective apices 30 of annular elements 10 to an intermediate location on respective strut members 20 of the annular elements 10. In FIG. 14e, two connectors extend from the same apex 30 of one annular element 10 to different apices 30 on the other annular element 10. Alternatively, connectors can extend from strut member to strut member without being connected to peaks of the annular members, or two or more connectors can extend from the same apex of both annular elements, respectively Although each of these embodiments depict the selected connectors extending in opposite circumferential directions, it is recognized that the connectors can all be arranged in the same direction as previously shown in FIG. 13.

Furthermore, the connector peaks 67 can be aligned longitudinally with each other in the circumferential direction, i.e., located on the same transverse plane of the endoprosthesis, but need not be so aligned. In the embodiments having connector peaks that are not aligned, it is contemplated that the endoprosthesis may be more completely or uniformly crimped if the connector peaks 67 extend circumferentially in opposite directions as shown in FIG. 14a, because the peaks of adjacent connectors will not interfere with each other. Furthermore, the connection locations 50 and the connectors 60, if present, on longitudinally-adjacent annular elements 10 are preferably circumferentially displaced with respect to each other to improve flexibility of the stent. However, all of the connection locations can be aligned, if desired.

In addition to changing connector shapes, other aspects of the connectors can be altered to facilitate desired performance characteristics for the endoprosthesis. For example, the length and cross-sectional dimensions (e.g., width, thickness) of the connectors can be varied as shown in FIG. 13, or the number of connectors between adjacent annular elements can be increased or decreased to alter longitudinal flexibility and coverage accordingly. Hence, longitudinal flexibility can be uniform or varied across the length of the endoprosthesis, as desired.

Further in accordance with an additional aspect of the invention, and as previously noted, the connection location between longitudinally-adjacent annular elements need not include a separate connector. Indeed, the connection location can be defined by an overlapping geometric pattern of two adjacent annular elements. As defined herein, "overlapping geometric pattern" and "overlapping pattern" reference the resulting pattern or configuration from two or patterns arranged to share a common surface or area; it does not suggest or require that this overlapping pattern result in an increase in thickness or material of construction. Preferably, the connection location includes a foot extension.

Figure 15:
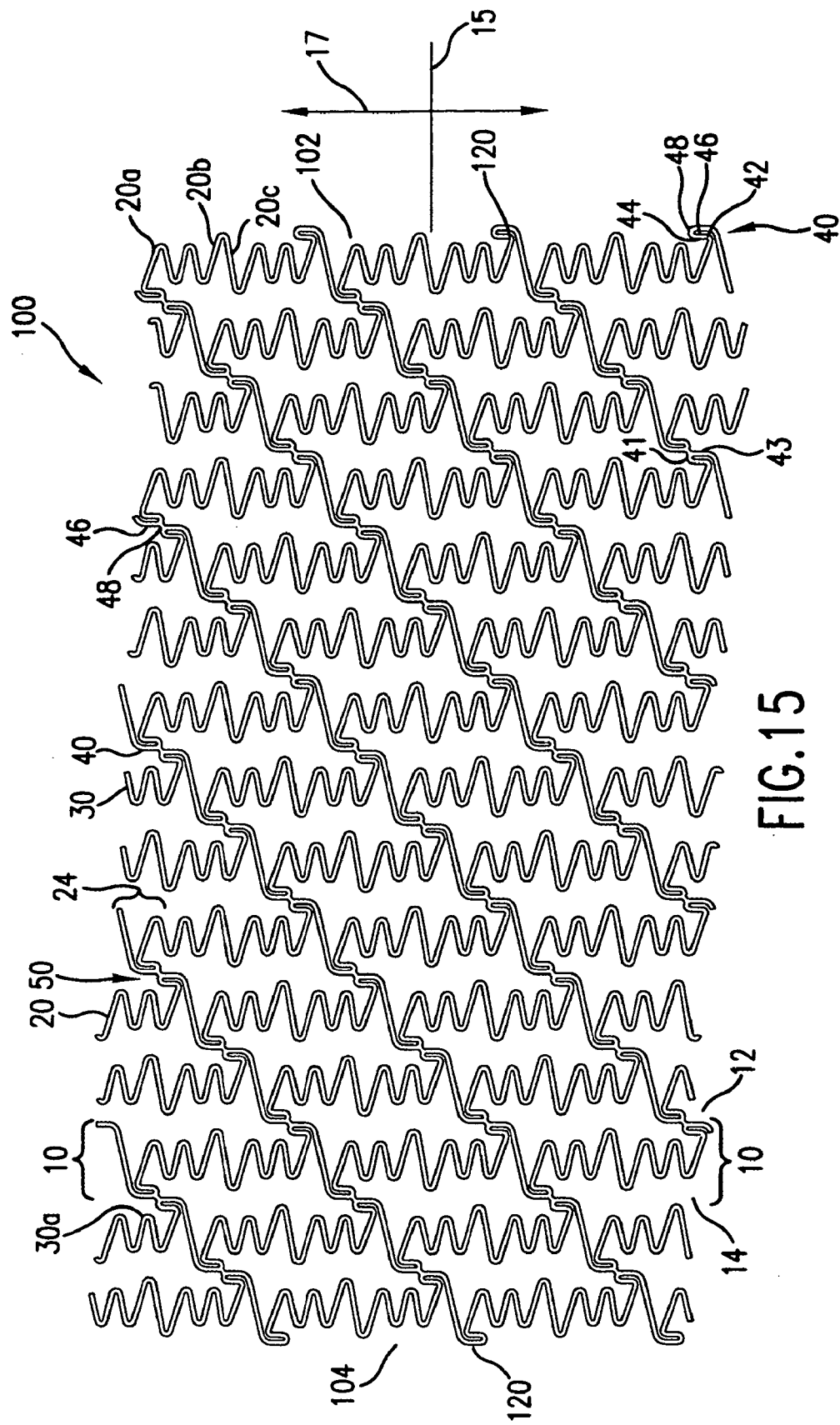
FIGS. 15 through 24 show alternative representative embodiments of the present invention in planar format, each of an endoprosthesis having annular elements connected at a plurality of connection locations without connectors.

For purpose of illustration and not limitation, reference is made to FIG. 15, which shows an endoprosthesis substantially similar to that of FIG. 1, but without separate connectors. FIG. 15 shows an endoprosthesis in a deployed configuration including a plurality of annular elements 10, each having first and second longitudinal sides 14, 16 with selected apices defined by foot extensions 40 extending in opposite circumferential directions. Connection locations 50 between the longitudinally-adjacent annular elements 10 are provided by direct connections between opposing foot extensions 40. As shown in this embodiment, each connection location 50 is generally disposed along the base portion 46 of each foot extension 40 proximate the toe portion 48, and aligned diagonally or helically along the length of the endoprosthesis. Each foot extension 40 of this embodiment can be construed to define a three point hinge configuration defined generally at the at the toe, heel, and ankle portions 48, 42, 44. Furthermore, and as noted with regard to FIG. 1, one or more foot extensions at either end 102, 104 of the endoprosthesis includes an area that undergoes minimal deformation or strain, such as the base portion 46, when expanded to the deployed configuration. A wire or strip of radiopaque material can be wrapped around or otherwise secured to this area of minimal strain so as to act as a radiopaque marker 120 for imaging purposes during delivery and deployment.

In this embodiment, the strut members 20 that are circumferentially adjacent the foot extensions 40 and within the circumferential extension of the foot extensions 40 when in the delivery configuration are dimensioned so the corresponding apices 30a mate with the foot extension 40 as described with regard to the foot extensions of FIG. 2c. For example, FIG. 15 shows two pairs of short strut members 20a interconnected sequentially to a medium-length strut member 20b, a longer strut member 20c, a medium-length strut member 20b, two pairs of short strut members 20a, which connects to the next foot extensions 40. In the delivery configuration, the medium and longer strut members have apices 30a therebetween that are circumferentially displaced from the toe extensions 40.

As with the endoprosthesis embodiments that include a connector for each connection location, a wide variety of alternative endoprosthesis embodiments without connectors at the connection locations are likewise within the scope of the invention. Particularly, and as previously noted, at least one of the first and second foot portions of the foot extension defines a base portion generally facing a longitudinally-adjacent annular element. By defining the connection location as an overlapping pattern of the base portion and a corresponding portion of the longitudinally-adjacent annular element, as shown schematically in FIG. 26 for clarity, no connector is required. Additionally, and as previously noted, the generally elongate area of the base portion further enables versatility in the circumferential alignment adjacent annular elements, and the multiple areas of flexure of the foot extension enable enhanced longitudinal flexibility between adjacent annular elements without the need for connectors. Furthermore, by eliminating the connectors, an endoprosthesis having more uniform coverage for scaffolding as well as for the delivery of a drug or similar beneficial agent, as described further below, can be provided.

A variety of design alternatives for different endoprosthesis embodiments without connectors can be achieved by selectively combining the various aspects of the present invention. For purpose of illustration and not limitation, as well as for comparison with the embodiment of FIG. 15, a number of exemplary embodiments including the combination of foot extensions and overlapping patterns at connection locations of the present invention are depicted in planar format in FIGS. 16-26.

Figure 16:
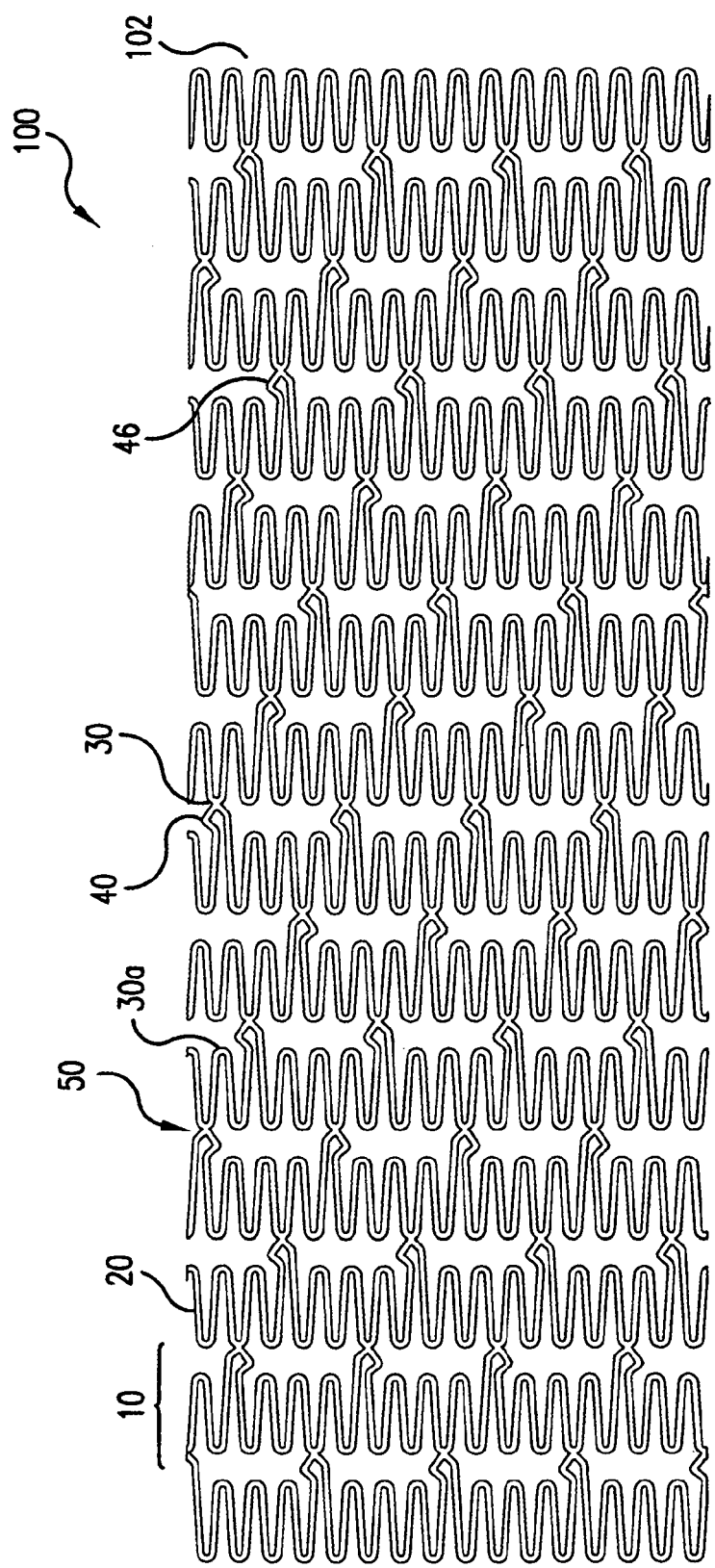
Figure 17:
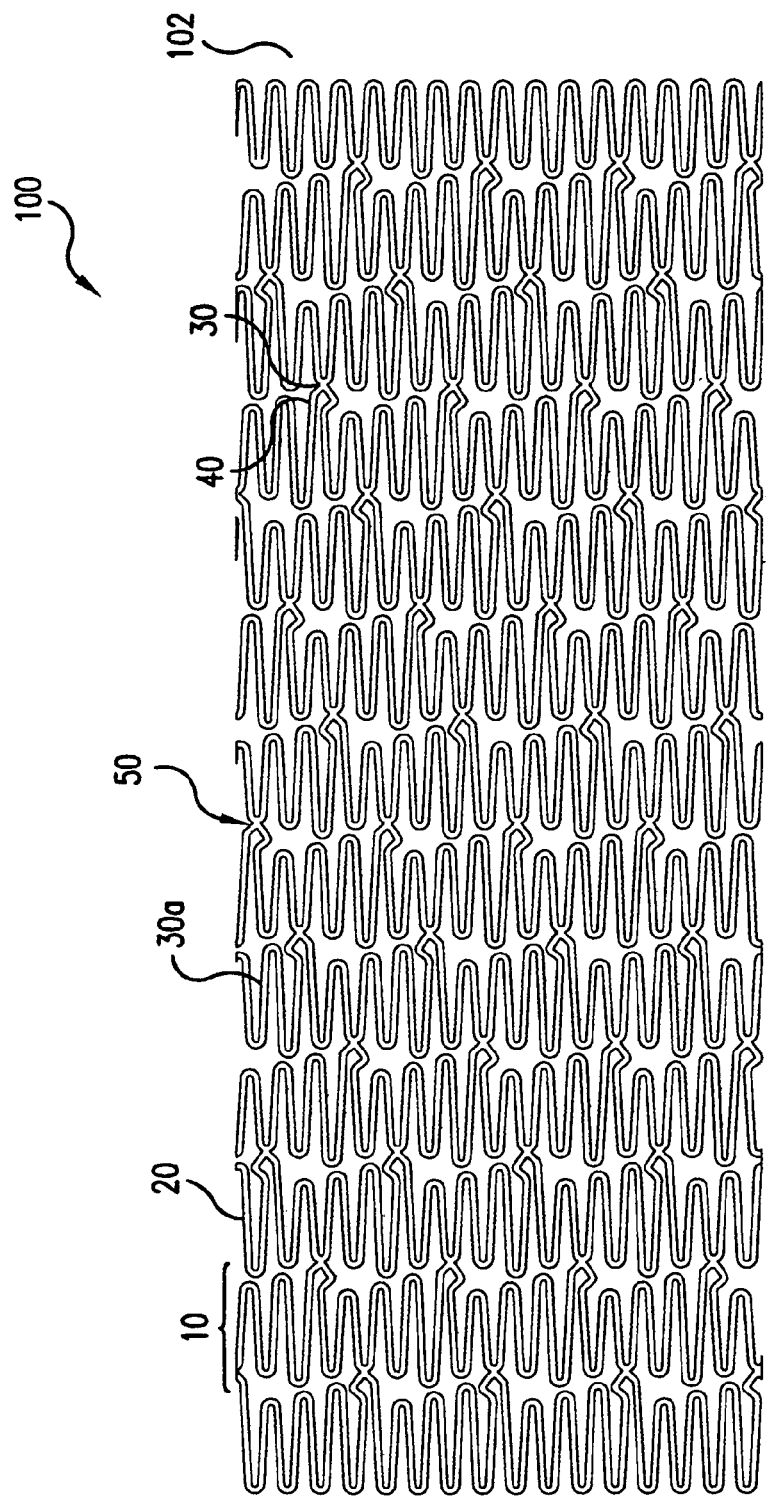

The embodiment of FIG. 16, shown substantially in a delivery configuration, includes a plurality of annular elements 10, wherein each longitudinal side of an annular element has 16 apices. In this embodiment, four apices on a selected side, e.g. 12, of adjacent annular elements 10 are defined by a foot extension 40, wherein the foot extensions 40 extend in the same longitudinal direction but in alternate circumferential directions from one annular element 10 to the next. Each foot extension 40 is configured substantially similar to that of FIG. 2c, wherein the base portion 46 is contoured to include first and second portions. The contoured pattern of the base portion 46 of each foot extension 40 overlaps with the pattern of an apex 30 of the circumferentially-adjacent annular element. Hence, four connection locations 50 are provided between longitudinally-adjacent annular elements 10, with three apices 30 disposed between the connection locations 50 along the corresponding longitudinal side 12, 14 of each annular element 10. The annular element 10 at the longitudinal end 102 of the endoprosthesis 100 in which the foot extensions 40 are directed is free of foot extensions 40. FIG. 17 shows an alternative embodiment similar to that of FIG. 16, wherein the lengths of the strut members 20 disposed circumferentially between the foot extensions 40 are varied to reduce the gap area defined between longitudinally-adjacent annular elements 10, and thus increase coverage.

Figure 18:
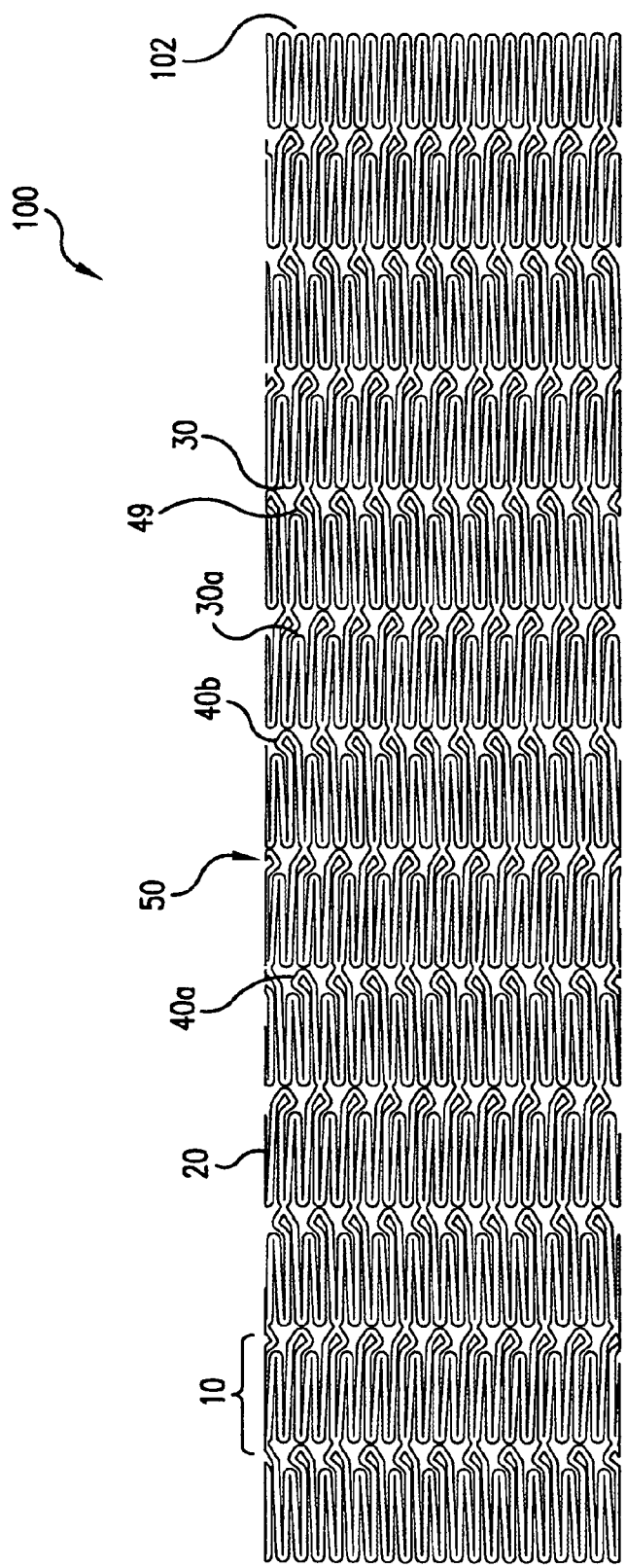
Figure 19:
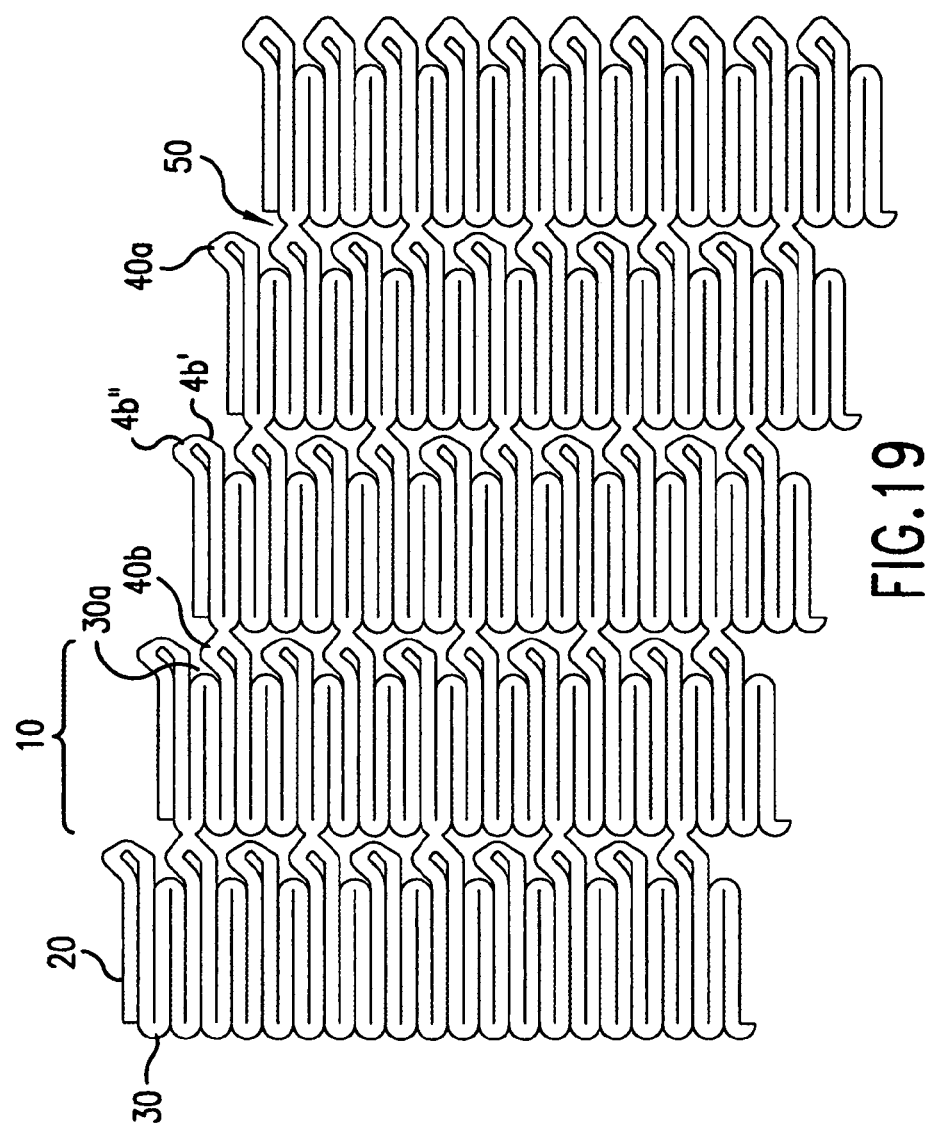

FIG. 18 shows an alternative embodiment similar to that of FIG. 16, wherein the center apex disposed along the longitudinal side 12, between the foot extensions 40b that define connection locations is defined as a foot extension 40a In this manner, circumferentially-adjacent foot extensions 40 along a longitudinal side of an annular element 10 are separated by single apex 30, wherein every other foot extension 40*b* forms a connection location with an apex 30 of a longitudinally-adjacent annular element 10. FIG. 19 shows an enlarged detail of an embodiment similar to FIG. 18, in the delivery configuration, wherein the base portion 46 of each foot extension 40 has an increased average width as previously discussed with regard to FIG. 2*c*. Particularly, the base portion 46 of each foot extension 40 is contoured with a generally V-shape to include a first portion 46' and second portion 46". The second portion 46" proximate the toe portion has a width greater than the first portion 46' as previously discussed. Furthermore, the foot extensions 40 of FIG. 19 are all directed in the same circumferential direction.

Figure 20:
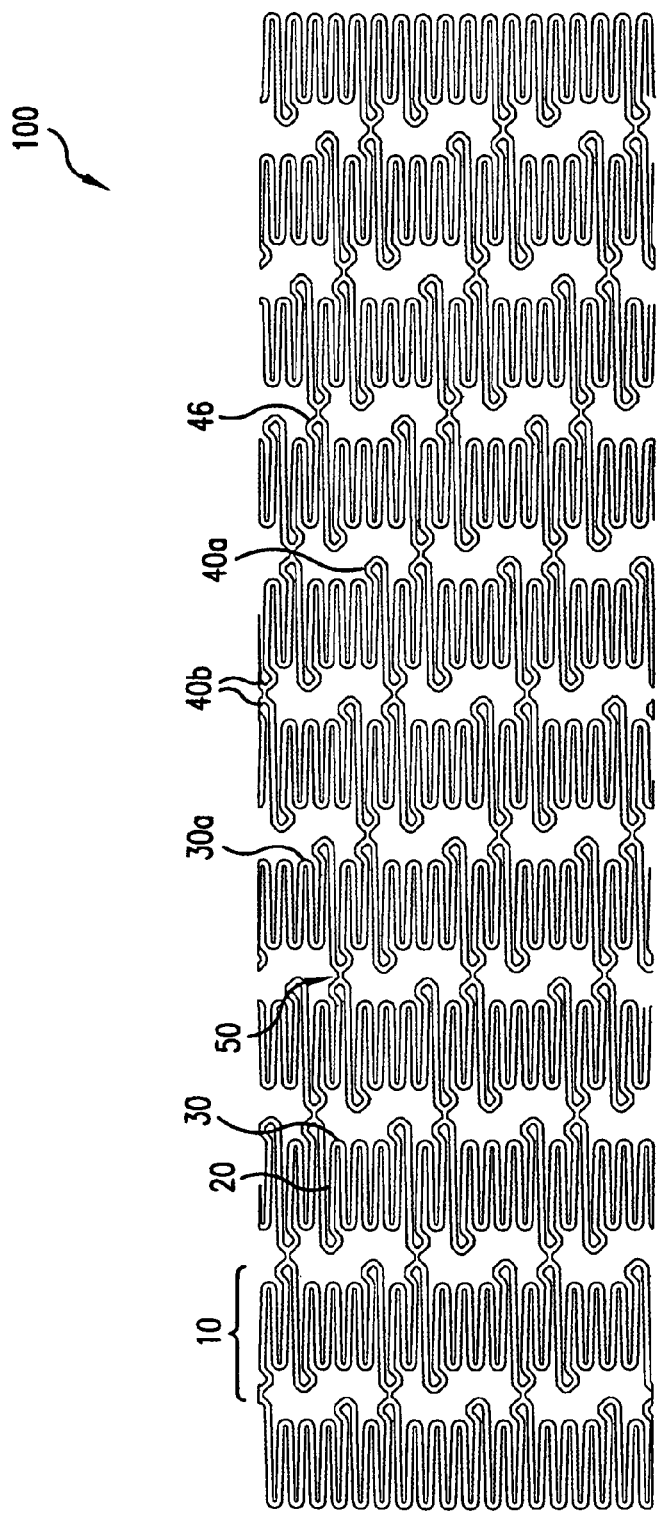

The embodiment of FIG. 20, which is shown substantially in a delivery configuration, includes 18 apices on each longitudinal side 12, 14 of each annular element 10. On each longitudinal side of an annular element 10 that faces an adjacent annular element, three pair of apices are defined by a pair of foot extensions 40 with each pair of foot extensions 40 having an apex 30*a* disposed therebetween. Furthermore, each pair of foot extensions 40 includes one foot extension 40*b* at a connection location 50 with a foot extension 40*b* on a corresponding side of a longitudinally-adjacent annular element 10. Hence, three connection locations 50 are provided between adjacent annular elements 10. Each foot extension 40 has a generally enlarged foot region 49. Particularly, each foot extension 40 at a connection location 50 has a contoured base portion 46 similar to that of FIG. 16, although more elongate in the longitudinal direction. The connection location 50 is thus defined by the base portions of the corresponding foot extensions 40*b*. It is noted that the foot extensions 40*a* that share a common strut member 20 in this embodiment are not at connection locations 50. The three pairs of foot extensions on each side 12, 14 are separated from each other in this embodiment by three apices 30.

Figure 21:
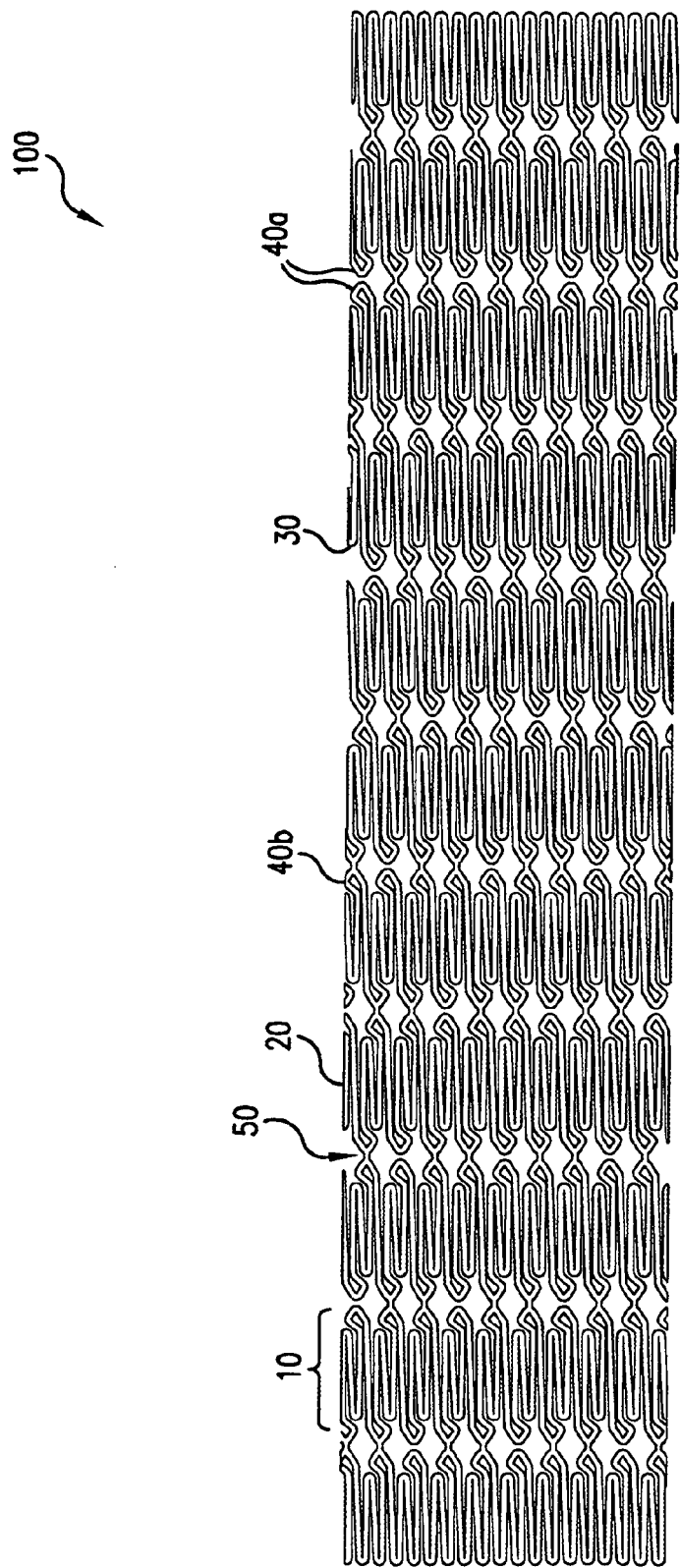

FIG. 21 shows an embodiment, substantially in a delivery configuration, including 18 apices on each side of each annular element 10, wherein every other apex on a side facing an adjacent annular element 10 is defined by a foot extension 40. Three pairs of circumferentially adjacent foot extensions 40*b* are connected to three corresponding pairs of foot extensions 40*b* on a longitudinally-adjacent annular element, so as to define six connection locations 50 as shown. Hence, three remaining foot extensions 40*a* on each side of the annular element 10 are interspersed between the three pair of foot extensions 40*b* of the connection locations 50. The foot extensions 40 on each side of the annular elements 10 extend in the same circumferential direction, but in a direction opposite the foot extensions 40 disposed on the opposite longitudinal side of the annular element 10.

Figure 22:
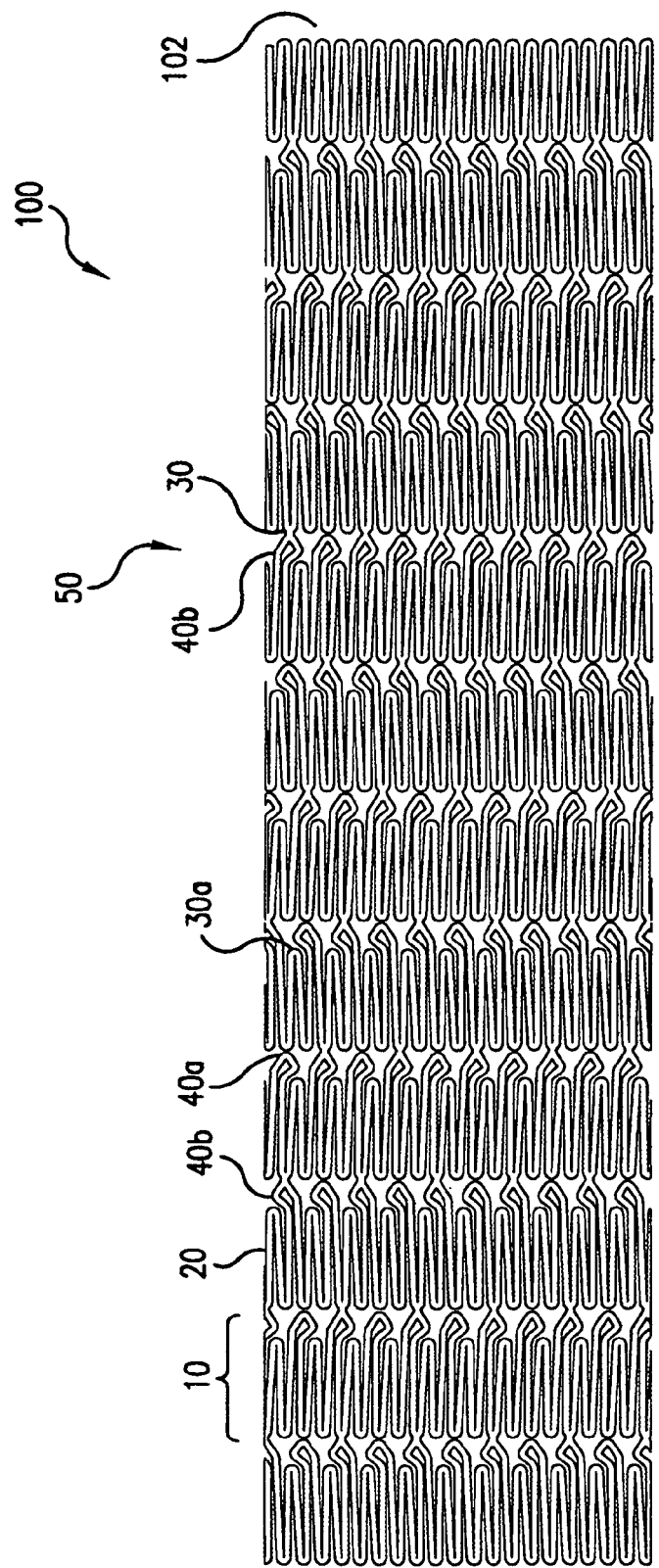
Figure 23:
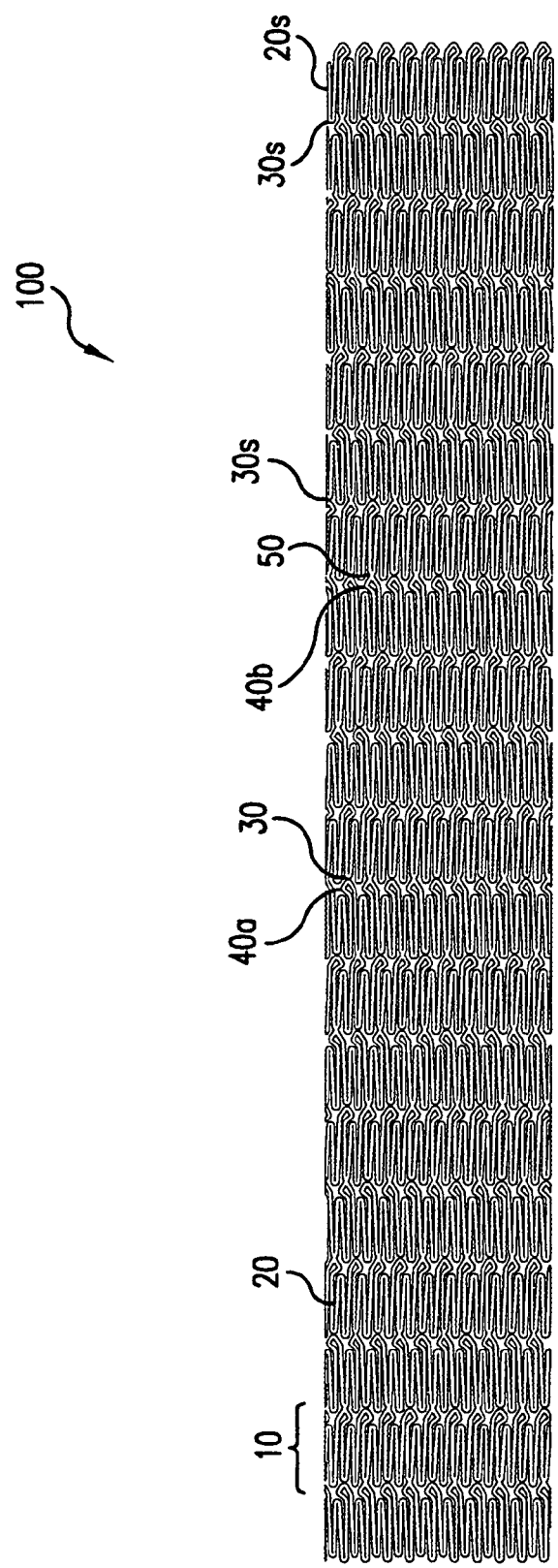
Figure 24:
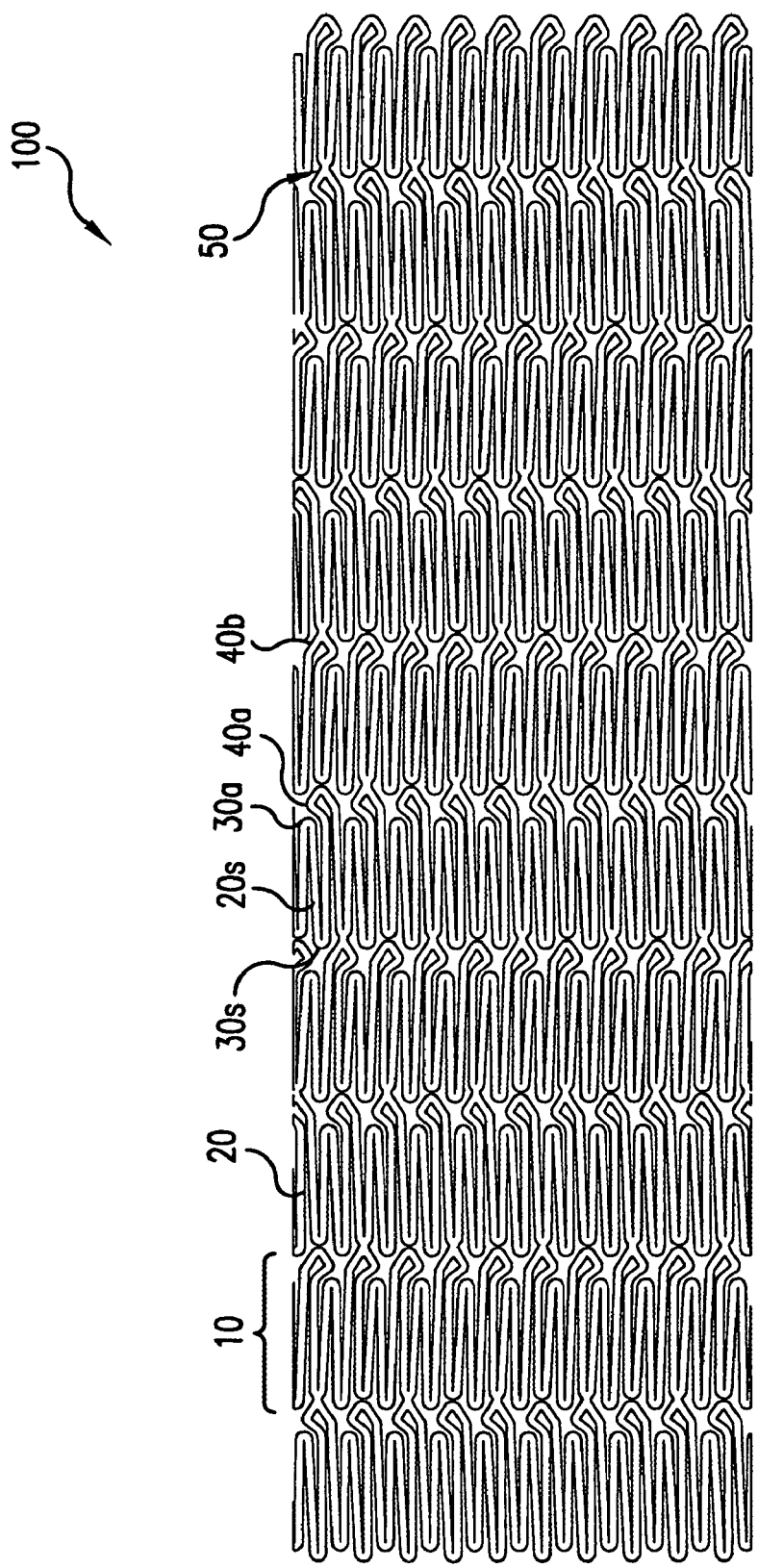

FIG. 22 shows an embodiment similar to that of FIG. 16, however, each annular element includes additional strut members and apices. Particularly, the embodiment of FIG. 22 includes 20 apices, rather than 16 apices, on each side of each annular element 10, with every other apex defined by a foot extension 40. Hence, five connection locations 50 are defined between adjacent annular elements 10. The embodiments of FIGS. 23 and 24 are similar to the embodiment of FIG. 22; however, selected apices 30*s* of one annular element are longitudinally aligned to be disposed between circumferentially adjacent foot extensions 40 of an adjacent annular element. As previously noted, and in accordance with the invention, the apices on longitudinally adjacent sides of adjacent annular elements 10 can be disposed so as to be circumferentially out of alignment with each other. Hence, the strut members 20*s* that are interconnected at the apices 30*s* disposed between adjacent foot extensions 40 of an adjacent annular element, are provided with a greater length than the remaining strut members so as to dispose the apex 30*s* generally between the foot extensions 40. In this manner, resulting coverage and scaffolding can be increased. Each of FIGS. 22-24 is shown substantially in a delivery configuration.

Figure 25A:
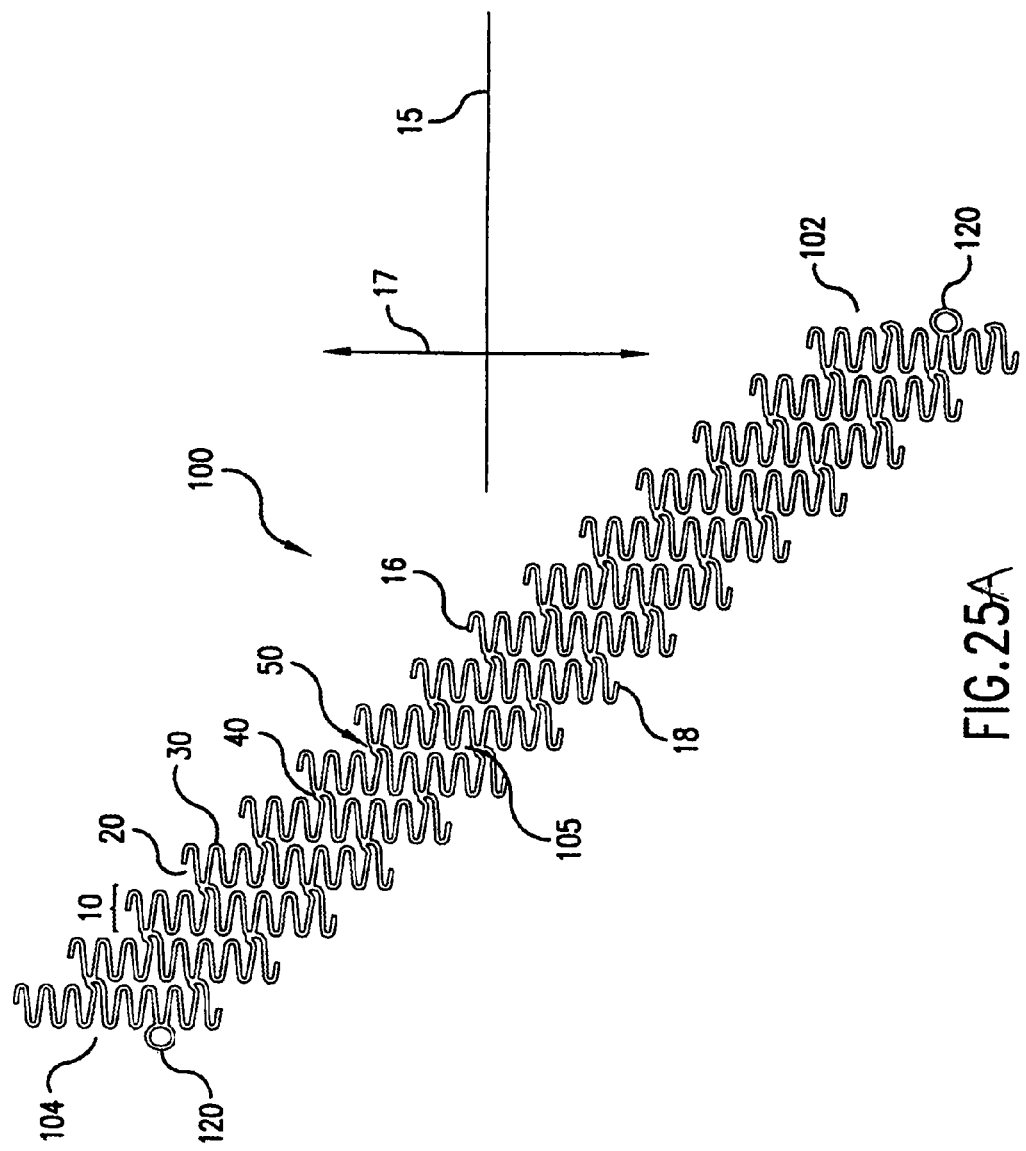
FIGS. 25a through 25f illustrate alternative embodiments of the present invention, wherein a marker housing and a marker are shown to be associated with the endoprosthesis.

FIG. 25*a* discloses an embodiment in a slightly deployed configuration having eight apices per side of each annular element 10. Each annular element 10 is arranged in a diagonal format to define a 360-degree turn of a helical pattern. In this manner, the circumferential end 18 of one annular element can be joined with the corresponding circumferential end 16 of a longitudinally-adjacent element to form a continuous helical pattern along the length of the endoprosthesis 100. Two apices on one side of each annular element are defined by foot extensions 40 similar to that of FIG. 2*b*. Each foot extension 40 forms an overlapping pattern with the apex 30 on a circumferentially adjacent side of an adjacent annular element. Hence, two connection locations 50 are defined between adjacent annular elements 10. As previously noted with regard to FIG. 2*b*, the apex 30*a* circumferentially adjacent to the foot extension 40 is longitudinally positioned to substantially contact the toe portion 48 when in the delivery configuration to increase coverage, as well as to capture balloon material if desired. The embodiment of FIG. 25*a* also includes an eyelet or tab to incorporate a radiopaque marker 120 at one or both ends 102, 104 of the endoprosthesis if desired. Alternative techniques for incorporating radiopaque material are described below.

Figure 25B:
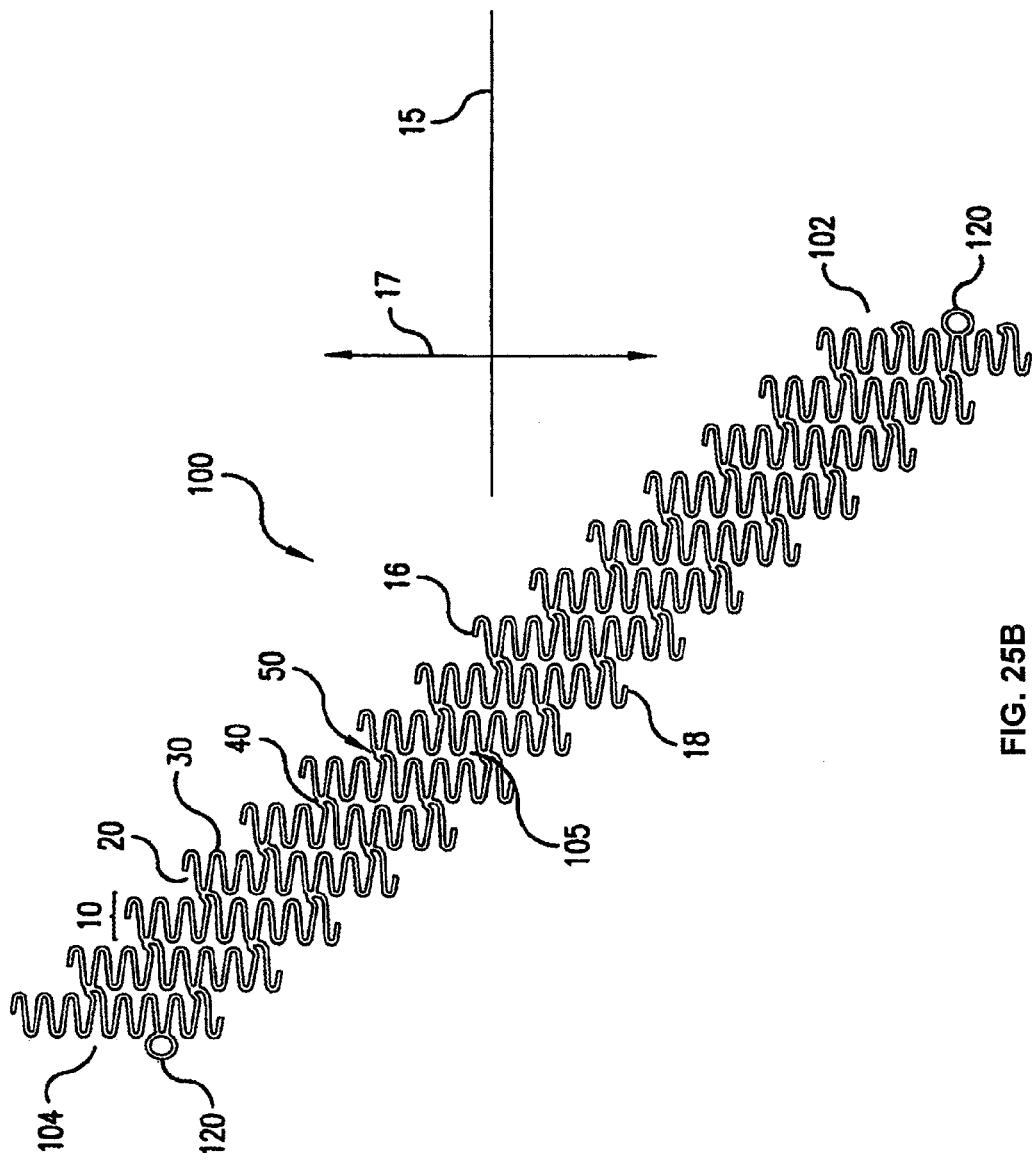

FIG. 25*b* discloses an alternative embodiment of the endoprosthesis according to the present invention, wherein the endoprosthesis includes at least one marker housing adjacent to one end of the endoprosthesis wherein a marker may be disposed therein. As shown in FIG. 25*b*, the endoprosthesis includes a plurality of strut members having first and second ends, wherein at least one pair of adjacent strut members further include a foot extension as previously described. The foot extension further includes a marker housing 121, wherein the marker housing is configured to retain a marker 120. As shown in FIG. 25*b*, the marker housing is attached to an apex 30 on one end 104 of the endoprosthesis and extends from a foot extension 40 on the opposite end 102. The marker housing(s) as shown in FIG. 25*b* are shown extending along an axis of either the apex or foot extension, though it is contemplated that the marker housings may extend from the apex and foot extension at and angle relative to an axis of the apex or foot extension. Marker housing 121 is designed such that the mechanical properties of the foot extension and/or the endoprosthesis are not affected. Alternatively, it is contemplated that the marker housing 121 may be design such that the marker housing 121 functions as a structural member of the endoprosthesis. As shown, the marker housing 121 includes an aperture formed therein, whereby the aperture is formed having a generally circular shape. Although, the aperture formed in the marker housing is described as being generally circular in shape, it is contemplated that the aperture may be formed having other shapes, such as rectangular, square, oval, octagonal, and the like. As shown in FIG. 25*b*, at least one marker housing may be additionally formed on the opposite side of the endoprosthesis device 100, wherein the second marker housing 121 is configured to be in association with one of the apices formed by the plurality of strut members as described previously.

As described above, a marker 120 may be disposed within the aperture of the marker housing. The marker may be composed of any material having greater radiopacity than the material from which the endoprosthesis device 100 is constructed. Examples of suitable material include, stainless steel, gold, silver, cobalt, platinum, iridium, tantalum, and alloys thereof or similar biocompatible or bioabsorbable materials. In a preferred embodiment, the marker comprises tantalum. The marker may be embodied in the form of a rivet, wherein the rivet includes first and second ends and is formed as a generally cylindrical member. It is contemplated that the marker may be manufactured as a composite, wherein one material may be radiopaque and the other material may be a beneficial agent. Wherein the beneficial agent may be configured to elute from the marker after implantation of the endoprosthesis. The marker 120 is preferably formed of a biocompatible material such as those described above.

Figure 25C:
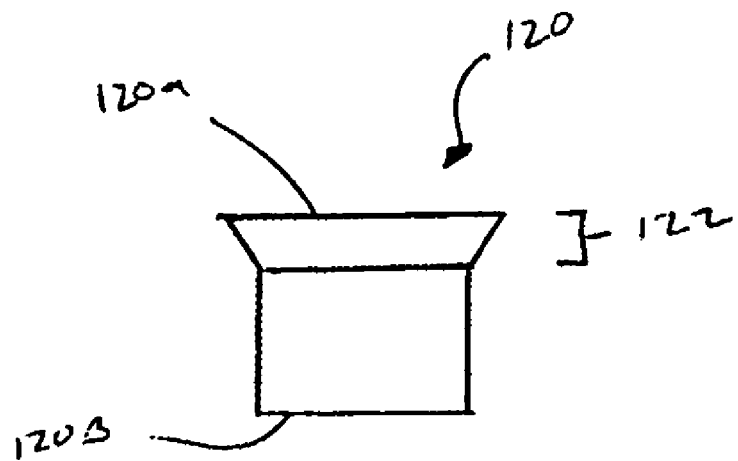
Figure 25D:
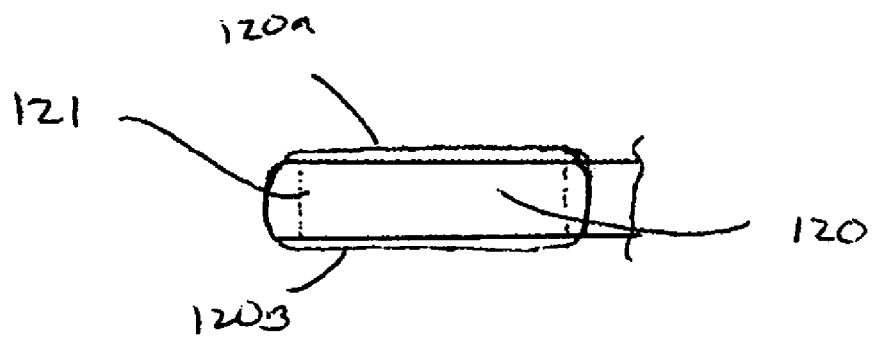

Referring now to FIG. 25c there is shown an exemplary embodiment of a rivet in accordance with the present invention. As shown in FIG. 25c, the rivet 120 includes a first end 120a and a second end 120b, wherein an enlarged diameter portion 122 is disposed adjacent to the first end 120a The enlarged diameter portion 122 being configured to retain the rivet within the aperture of the marker housing 121 prior to deformation of the rivet. As shown in FIG. 25d, there is shown a marker housing wherein a rivet has been disposed within the aperture of the housing, wherein the enlarged diameter portion 122 of the rivet extends beyond the outer surface of the endoprosthesis device 100 and the second end 120b of the rivet has been deformed to form a second enlarged diameter portion as shown. By forming the second enlarged diameter portion adjacent the second end 120b of the rivet, the rivet 120 is retained within the marker housing with a frictional fit and/or a mechanical interference of the enlarged diameter portions and the inner and outer walls of the endoprosthesis device. It is further contemplated that the rivet as shown in FIG. 25c may be constructed of multiple pieces which may then be assembled to form a single member when disposed within a marker housing in accordance with the present invention. For example, the rivet may comprise upper, middle, and lower pieces, wherein the middle piece includes means to affix the upper and lower pieces thereto, such as a protrusion extending from each end of the middle piece, wherein the upper and lower pieces include an aperture or recessed area configured to receive the protrusion. Alternatively, a fourth piece may be utilized to affix the upper, middle and lower pieces together to form a marker in accordance with the present invention.

The rivet may be manufactured from a sheet of material, wherein the rivets are produced by stamping and a second process is performed to form the enlarged diameter section. Alternatively, the rivets may be manufactured by cutting the rivets from round stock, wherein the cut portions may then be tumbled to radius the edges then machined to produce the increased radius portion. Further still, the rivets may be manufactured utilizing other known techniques such as injection molding, casting, machining, hydroforming and the like.

It is further contemplated that the marker 120 may be formed with alternative methods, for example, the marker may be integrally formed with the endoprosthesis device during the initial manufacturing step. Such a process would involve manipulating a tubular member or a sheet of material from which the endoprosthesis device is constructed from prior to the formation of the endoprosthesis device. For example, if the endoprosthesis were to be formed from a thin-walled tubular member, a groove or other feature may be formed in one of the walls of the tube, wherein a radiopaque material may then be disposed within the groove or feature. Alternatively, the locations of the marker housing may be preformed on the device wherein markers may pre-disposed within the marker housings prior to the manufacture of the endoprosthesis device, which may then be formed according to known methods and those described herein.

Although the marker housings are shown and described as being disposed on either end of the endoprosthesis device of the present invention, it is further contemplated that marker housings may be formed anywhere along the length and/or radius of the endoprosthesis device in accordance with the present invention. Markers disposed anywhere along the length of the endoprosthesis may be utilized to denote the location where the physical properties of the endoprosthesis changes, or where a diameter change occurs, or the location of a side opening formed in the wall of the tubular member.

Figure 25E:
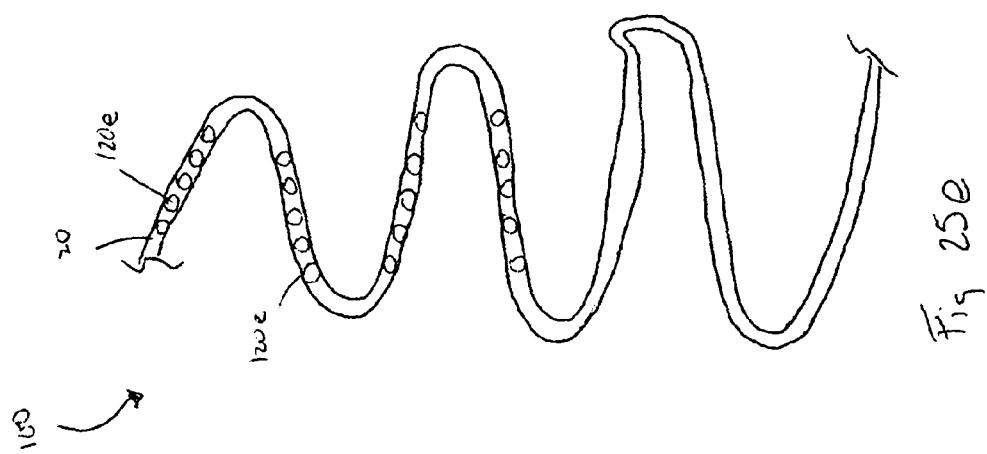

FIG. 25e illustrates yet another alternative embodiment of the endoprosthesis in accordance with the present invention, wherein the endoprosthesis includes a plurality of markers disposed along at least one of the strut members. The markers may be comprised of rivets disposed within openings formed in the strut members as described above or alternatively, the markers may be integrally formed upon the strut member during fabrication of the endoprosthesis. For example, as described herein, the endoprosthesis may be formed from a tubular member, wherein the struts and foot extensions are formed in the tubular member utilizing laser cutting or similar processes, the markers 120e formed on the strut members 20, may be formed by cutting away, machining away, chemical milling, or electropolishing material away from the strut member to form the markers 120e. The markers 120e may be formed having any shape or profile.

Figure 25F:
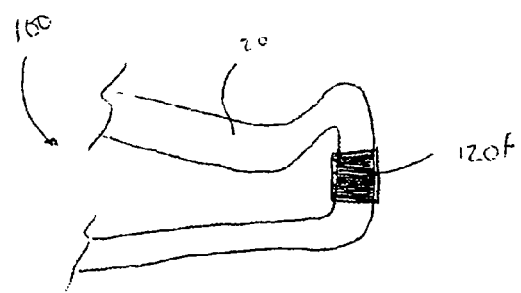

FIG. 25f illustrates an alternative radiopaque marker in accordance with the endoprosthesis of the present invention. As shown in FIG. 25f, the marker 120f comprises a clip or a band that may be attached to one of or a plurality of strut members along the length of the endoprosthesis device 100. The marker 120f may be constructed of a material such as tantalum, gold, gold plating, silver, silver plating, alloyed metals, polymers, plastics, or similar biocompatible or bioabsorbable materials, wherein the marker would be configured to be retained on the endoprosthesis by deforming the marker such that the marker would be frictionally retained on the endoprosthesis. It is further contemplated that the marker may be affixed to the endoprosthesis utilizing other methods such as welding, gluing, swaging, or similar methods.

In addition to the embodiments shown above in FIGS. 25a through 25f, it is contemplated that the marker housings may be formed within an apex of one or more strut members or within a portion of the foot extension of the embodiments shown and described herein. Additionally, it is contemplated that a marker housing may be formed anywhere along the length of the endoprosthesis in accordance with the present invention. For example, it may be desirable to have markers disposed anywhere along the length of the endoprosthesis between each end of the endoprosthesis. Therefore, in accordance with the present invention, it is contemplated that marker housings may be formed for example in the middle of the endoprosthesis to indicate a specific area or property of the endoprosthesis. As such, markers may be disposed in marker housings formed within the struts, apices, or foot members of the endoprosthesis, or marker housings such as those shown in FIGS. 25a and 25b maybe integrated in the endoprosthesis anywhere along the length of the endoprosthesis. Further still, a variety of the marker embodiments described and shown herein may be utilized in any combination along the length of an endoprosthesis according to the present invention, wherein different marker embodiments may be utilized to mark locations of interest.

Figure 26:
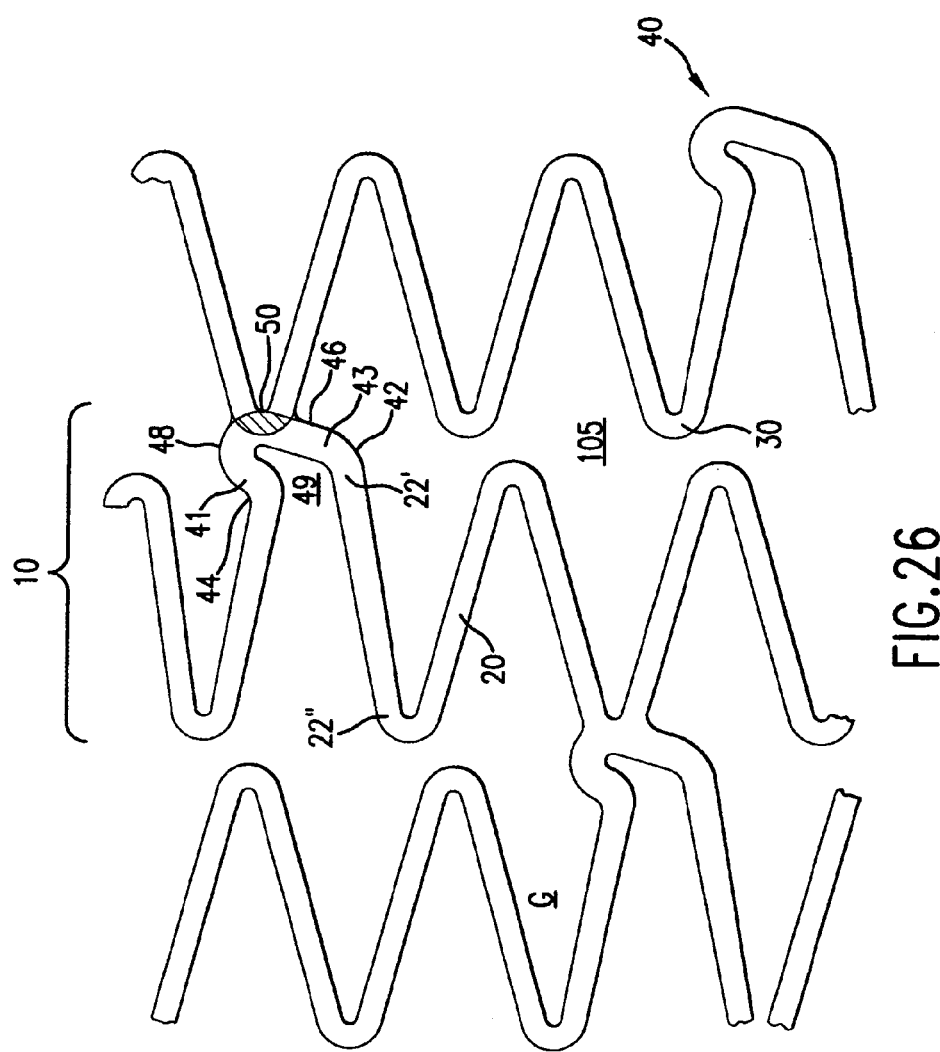
FIGS. 26 and 27a through 27d are detail views, in planar format, showing various embodiments of overlapping patterns of adjacent annular elements defining connection locations.

FIG. 26 is an enlarged view of a connection location similar to that of FIG. 25a, wherein the overlapping geometric pattern of a connection location is schematically depicted for purpose of illustration. Particularly, FIG. 26 shows an annular element having a foot extension similar to that of FIG. 2a. The pattern of the foot extension 40b along the base portion 46 is aligned longitudinally to overlap with a portion of the pattern of a circumferentially adjacent annular element 10. The resulting configuration of the overlapping pattern defines the connection location 50 between the two annular elements 10. The amount or extent of overlap between the two patterns can be varied as desired. For example, the patterns can be substantially in tangential contact, or can be fully overlapping. Additionally, fillets or a similar transition can be included to smooth or eliminate any sharp or abrupt edges. It is noted that the thickness at the juncture defined by the overlapping patterns need not be, and preferably is not, increased. Rather, the overlapping pattern refers to the resulting configuration when two separate patterns share a common surface or area.

Figure 27C:
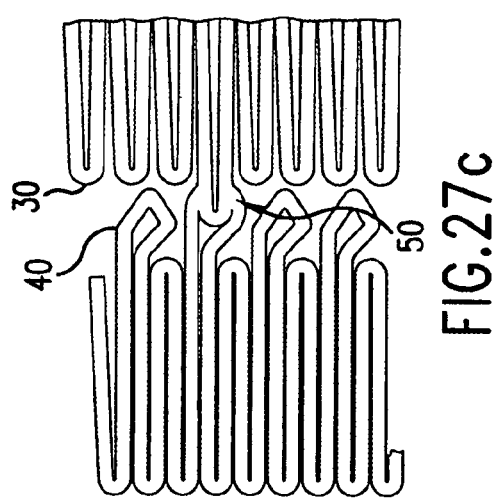
Figure 27D:
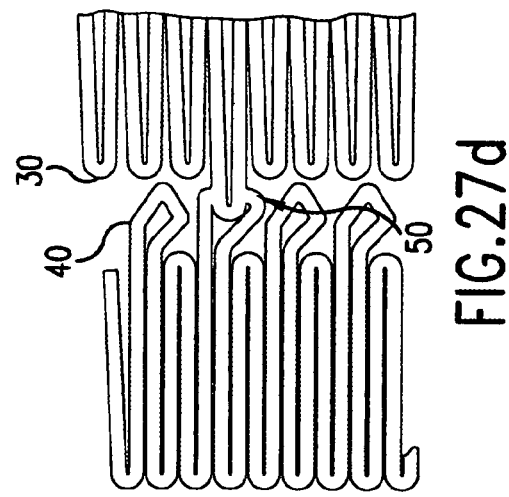
Figure 27A:
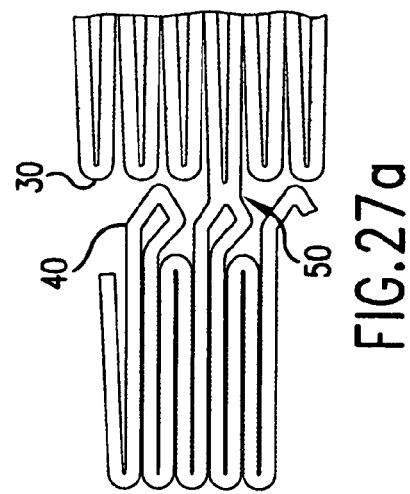
Figure 27B:
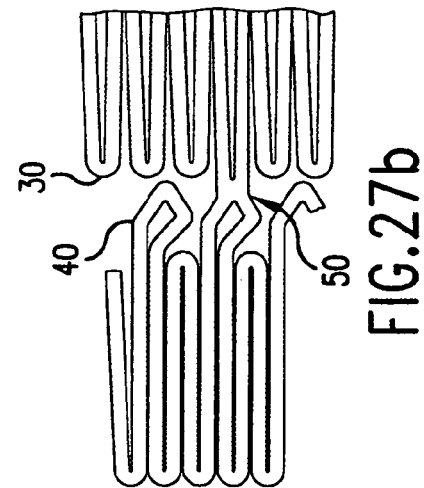

FIGS. 27a through 27d show alternative connection locations 50 defined by different degrees of geometrical overlap between adjacent annular elements 10. The connected foot extension 40b and apex 30 of FIG. 27a have a slight geometrical overlap, such as a tangential surface contact. FIG. 27b shows an overlapping pattern, wherein the connected apex 30 and foot extension 40b fully overlap to substantially share a common member. As depicted, the apex 30 at the connection location 50 extends longitudinally further than the unconnected apices 30. In FIG. 27c, the apex 30 at the connection location 50 protrudes into the foot region of the corresponding foot extension 40b. In this embodiment, the foot extension 40b is generally enlarged and rounded at the base portion 46 compared to free foot extensions 40a to stiffen and reinforce the connection location 50. Additional areas of flexure can be defined by the contour of this configuration, as compared to that of the other foot extensions. By contrast, connected foot extension 40b of FIG. 27d includes a flattened base portion 46 substantially perpendicular to the longitudinal axis to define a more relaxed configuration. As with FIG. 27c, the connected apex 30 of this embodiment overlaps with the foot extension 40b and protrudes into the foot region 49.

As noted above, the various aspects of the present invention allow for a variety of different endoprosthesis embodiments, based upon selective combinations of the features previously described and shown. Similarly, the endoprosthesis of the present invention can be made using any of a number of known manufacturing techniques and materials.

The material of construction is preferably selected according to the performance and biological characteristics desired. For example, the endoprosthesis of the invention can be made to be expanded by the change of a delivery condition, such as by the removal of a restraint or exposure to the environment within the body lumen, so as to be self expanding, or by the application of an external force or energy, such as by a balloon or by a radio frequency. For purpose of illustration and not limitation, reference is made generally to "self-expanding" embodiments and "balloon expandable" embodiments of the endoprosthesis of the present invention.

Self-expanding embodiments can be made from any of a variety of known suitable materials including super elastic or shape memory materials, such as nickel-titanium (NiTi) alloys, Elgiloy, and suitable polymers, such as suitable shape memory polyurethane copolymers, or any equivalents thereof. An endoprosthesis made of a suitable super elastic material can be compressed or restrained in its delivery configuration on a delivery device using a sheath or similar restraint, and then deployed to its deployed configuration at a desired location by removal of the restraint as is known in the art. An endoprosthesis made of shape memory material generally can be delivered in a like manner, and if thermally sensitive, can be deployed by exposure of the endoprosthesis to a sufficient temperature to facilitate expansion as is known in the art. It also is possible to make the self-expanding embodiment of a biocompatible material capable of expansion upon exposure to the environment within the body lumen, such as a suitable hydrogel or hydrophilic polymer, including biodegradable or bioabsorbable polymers, such as polycaprolactone (PCL), poly-D,L-lactic acid, Poly-L-lactic acid, poly (lactide-co-glycolide), poly(hydroxybutyrate), polyanhydrides, poly(glycolic acid). For example, if made of an expandable hydrophilic material, the endoprosthesis can be delivered to the desired location in an isolated state, and then exposed to the aqueous environment of the body lumen to facilitate expansion. Alternative known delivery devices and techniques for a self-expanding endoprosthesis likewise can be used. Prior to crimping of the self-expanding endoprosthesis for loading into a delivery system, the endoprosthesis may be coated with a lubricant such as silicone oil to reduce force between the endoprosthesis and the crimping device and additionally to reduce forces of disposing the endoprosthesis in a delivery device. Additionally, the lubricant may reduce deployment force thereby increasing accuracy of endoprosthesis placement within a patient. The lubricant may be introduced prior to, during, or after the crimping or loading process.

It is further contemplated that the markers in accordance with the present invention may improve the deliverability of a self-expanding endoprosthesis when used with a movable sheath delivery system. The markers projecting above the outer surface of the tubular body of the endoprosthesis contact the sheath of the delivery system and hold the sheath above the surface of the endoprosthesis, thereby reducing friction between the sheath and the endoprosthesis. Additionally, by having point contact between the sheath and the endoprosthesis it is possible the system may be more flexible and thus have better delivery characteristics compared to a similar system where the sheath is in continuous contact with the endoprosthesis. In addition to providing improved deliverability, it is contemplated that by having the markers protrude about the surface of the endoprosthesis this may provide less trauma to the tissue surrounding the endoprosthesis after delivery of the endoprosthesis by holding the surface of the endoprosthesis off the tissue and providing only points of contact.

Balloon expandable embodiments or the like can be made of any of a variety of known suitable deformable materials, including stainless steel, silver, platinum, cobalt chromium alloys such as L605, MP35N or MP20N or any equivalents thereof. "L605" is understood to be a trade name for an alloy available from UTI Corporation of Collegeville, Pa., including about 53% cobalt, 20% chromium and 10% nickel. "MP35N" and "MP20N" are understood to be trade names for alloys of cobalt, nickel, chromium and molybdenum available from Standard Press Steel Co., Jenkintown, Pa. MP35N generally includes about 35% cobalt, 35% nickel, 20% chromium, and 10% molybdenum. MP20N generally includes about 50% cobalt, 20% nickel, 20% chromium and 10% molybdenum. For delivery, the endoprosthesis of a suitable material is mounted in the delivery configuration on a balloon or similar expandable member of a delivery device. Once properly positioned within the body lumen at a desired location, the expandable member is expanded to expand the endoprosthesis to its deployed configuration as is known in the art. Additionally, or alternatively, balloon expandable embodiments can be made of suitable biocompatible polymers, including biodegradable or bioabsorbable materials, which are either plastically deformable or capable of being set in the deployed configuration. If plastically deformable, the material is selected to allow the endoprosthesis to be expanded in a similar manner using an expandable member so as to have sufficient radial strength and scaffolding and also to minimize recoil once expanded. If the polymer must be set in the deployed configuration, the expandable member can be provided with a heat source or infusion ports to provide the required catalyst to set or cure the polymer. Alternative known delivery devices and techniques for a self-expanding endoprosthesis likewise can be used.

Additional materials or compounds also can be incorporated into or on the endoprosthesis if desired. For example, the endoprosthesis can be provided with one or more coatings of biocompatible material to enhance the biocompatibility of the device. Such coatings can include hydrogels, hydrophilic and/or hydrophobic compounds, and polypeptides, proteins or amino acids or the like, including poly vinyl pyrrolidone (PVP), poly vinyl alcohol (PVA), parylene, and heparin. A preferred coating material includes phosphorylcholine, as disclosed in U.S. Pat. Nos. 5,705,583 and 6,090,901 to Bowers et al. and U.S. Pat. No. 6,083,257 to Taylor et al., each of which is incorporated by reference herein. Such coatings can also be provided on the endoprosthesis to facilitate the loading or delivery of beneficial agents or drugs, such as therapeutic agents, pharmaceuticals and radiation therapies. Alternatively, the surface of the endoprosthesis can be porous or include one or more reservoirs or cavities formed therein to retain beneficial agent or drug therein as is known in the art. For purposes of illustration and not limitation, the drug or beneficial agent can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors, antisense compounds, oligionucleotides, cell permeation enhancers, and combinations thereof.

The endoprosthesis can also be provided with coverings, such as PTFE, ePTFE, Dacron, woven materials, cut filaments, porous membranes, harvested vessels and/or arteries, or others such materials to form a stent graft prosthesis. Similarly, a medical device, such as a valve, a flow regulator or monitor device, can be attached to the endoprosthesis, such that the endoprosthesis functions as an anchor for the medical device within the body lumen.

Additionally, an imaging compound or radiopaque material can be incorporated with the endoprosthesis. For example, one or more of the annular elements of the endoprosthesis can be made of a suitable radiopaque material, such as gold, tantalum or a similar material. Alternatively, the radiopaque material can be applied on selected surfaces of one or more of the annular elements using any of a variety of known techniques, including cladding, bonding, adhesion, fusion, deposition or the like. In a preferred embodiment, the material used for fabrication of the endoprosthesis includes a composite structure having multilayers of different materials or compositions. Generally, at least one layer is a base material such as stainless steel, nickel-titanium alloy or cobalt chromium alloy to impart the intended structural characteristic of the endoprosthesis, and at least another layer is a radiopaque material such as gold or tantalum for imaging purposes. For example, a tri-layer structure of 316L-Ta-316L is preferred for a balloon expandable stent and a tri-layer structure of NiTi—Ta—NiTi is preferred for a self-expanding stent. Suitable multi-layered composite structures are available in sheet or tube form from UTI Corporation of Collegeville, Pa., and are disclosed in U.S. Pat. No. 5,858,556, which is incorporated herein by reference. In yet another embodiment, one or more marker elements of radiopaque material can be attached to the endoprosthesis. For example, and as previously shown in FIG. 25, eyelets or tabs can be provided on one or more annular elements, preferably at at least a distal or proximal longitudinal end of the endoprosthesis. A rivet or bead of radiopaque material can then be attached to the eyelet or tab in a manner as known in the art. Alternatively, the separate marker can be attached directly to annular element. For example, and in accordance with a preferred embodiment of the invention as shown in FIGS. 1 and 15, a wire or strip of radiopaque material can be wrapped around and secured to a base portion of one or more foot extensions at one or both longitudinal ends of the endoprosthesis; preferably by providing the foot extension with a geometry to enable limited strain in the base portion of the foot extension upon deployment.

A variety of manufacturing techniques are well known and may be used for fabrication of the endoprosthesis of the present invention. For example, and in a preferred embodiment, the endoprosthesis can be formed from a hollow tube of suitable material using a known technique, such as by laser cutting, milling or chemical etching. The structure is mechanically blasted with a media and then electropolished or otherwise finished to remove burrs and eliminate sharp edges and contaminates. An additional de-scaling process may be performed after electropolishing, wherein the de-scaling process involves the use of an acid bath. Alternatively, the endoprosthesis can be fabricated from a sheet of suitable material using a similar cutting, milling or etching technique, and then rolled or bent about a longitudinal axis into the desired shape. If desired, the lateral edges of the structure can be joined together, such as by welding or bonding, to form a closed tubular structure, or the lateral edges can remain unattached to form an coiled, rolled sheet or open tubular structure. Conversely, a suitable material of construction can be applied selectively to a substrate to define the desired pattern of the endoprosthesis structure, and then the substrate can be removed. Other methods of manufacture also can be used for the endoprosthesis of the present invention, such as by bending toroidal rings or elongate lengths of wire into appropriately shaped members, such as that corresponding to each annular element, and then joining the appropriately shaped members together at connection locations by a welding or bonding technique or the like. If a shape memory material is used, such as a nickel titanium alloy, the fabricated structure can be heat treated on a mandrel or the like using known techniques to establish the desired endoprosthesis shape and dimensions at a predetermined temperature, e.g. when above austenitic transition temperature.

An additional step of passivation may be performed during the manufacturing stage of the endoprosthesis in order to form a homogeneous oxide layer for corrosion resistance. The passivation process may be performed prior to installation of the markers in accordance with the present invention or it may be performed after installation of the markers. Alternatively, multiple passivation processes may be performed, once prior to insertion of the markers and again after insertion of the markers.

As originally cut or fabricated, the endoprosthesis can correspond to its delivery configuration or to a deployed configuration or a configuration therebetween. Preferably, however, the endoprosthesis is fabricated with a configuration at least slightly larger than the delivery configuration as shown in the planar formats of FIGS. 6-10 and 16-24, for example. In this manner, the endoprosthesis can be crimped or otherwise compressed into its delivery configuration on a corresponding delivery device. In another preferred embodiment, the endoprosthesis is originally fabricated from a tube having a diameter corresponding to the deployed configuration. In this manner, the longitudinally-free portions of the annular elements (e.g., apices not at a connection location) and circumferentially-free portions (e.g., the toe portion of the foot extensions) can be maintained within the general cylindrical shape (e.g., diameter) of the endoprosthesis when deployed, so as to avoid such portions from extending radially inwardly when in the deployed configuration. The endoprosthesis is therefore designed to match the target vessel in which the endoprosthesis is to be deployed. For example a stent will typically be provided with an outer diameter in the deployed configuration ranging from about 1 mm for neurological vessels to about 25 mm for the aorta. Similarly, a stent will typically be provided with a length ranging from 5 mm to 200 mm. Variations of these dimensions will be understood in the art based upon the intended application or indication for the endoprosthesis.

As previously noted, the geometry of each component of the endoprosthesis, such as the width, thickness, length and shape of the strut members and foot portions, as well as of the connectors if provided, is preferably selected to obtain predetermined expansion, flexibility, foreshortening, coverage scaffolding, and cross profile characteristics. For example, longer strut members can promote greater radial expansion or scaffolding coverage. The phase difference or circumferential alignment between adjacent annular elements likewise can be altered to control coverage and flexibility as well as facilitate more uniform drug delivery. Similarly, the number and placement of connection locations and, if present, the connectors, between longitudinally-adjacent annular elements are preferably selected to obtained the desired flexibility of the endoprosthesis. The number of apices and foot extensions between connection locations also can be varied to achieve desired performance characteristics. FIG. 28 depicts a representative embodiment depicting such variations within an endoprosthesis of strut lengths and strut widths for varied rigidity, and of connector locations for varied flexibility.

As recognized from the detailed description above, the foot extensions particularly enhance and provide versatility in the design of the endoprosthesis of the present invention. The foot extension can be configured and dimensioned relative to the strut members and the remainder of the endoprosthesis to compensate for longitudinal foreshortening upon stent expansion. For example, the areas of flexure of the foot extensions can be adjusted by contouring the foot geometry and dimensions, as well as by altering the lengths of selected strut members. Alternatively, the geometry of the foot extension can be configured to provide a desired amount of lengthening or shortening of the endoprosthesis upon expansion. The foot extensions can be configured to balance or assist in evenly distributing strain or expansion of the endoprosthesis. The foot extensions also can improve and control the flexibility of the endoprosthesis, preferably without substantially impacting the desired coverage or scaffolding of the endoprosthesis. The circumferentially elongated base portion of each foot extension provides a wide range of connection locations, and allows adjacent annular elements to be attached over a range of phase differences or circumferential alignment. The foot extensions can be configured to produce a torque on longitudinally free portions, such as unconnected apices, to maintain these longitudinally free portions within the general cross profile of the endoprosthesis when flexed along its longitudinal axis or expanded to its deployed configuration. This feature can be adjusted if it is desired to embed portions of the endoprosthesis into the vessel wall or other tissue.

Reference is now made to two exemplary preferred embodiments of a stent of the present invention; a self-expanding stent as shown in FIGS. 29a through 29f, and a balloon expandable stent as shown in FIGS. 30a through 30f.

FIG. 29a shows the planar format of a preferred embodiment of a self-expanding stent as cut and polished in a slightly deployed configuration. As depicted herein, the self-expanding stent comprises ten annular elements 10 with five connection locations 50 between longitudinally-adjacent annular elements 10 for an approximate stent length of about 21 mm. Annular elements can be added to increase the stent length, or omitted to decrease the stent length, as desired. Each annular element 10 includes fifteen apices per longitudinal side. On one longitudinal side 12 of each annular element 10, five apices are defined by foot extensions 40. Two circumferentially-adjacent apices 30 are located between adjacent foot extensions. On the other longitudinal side 14 of each annular element 10, no foot extensions are provided. Each foot extension 40 has a shape similar to that of FIG. 2c, as previously described in detail. Each of the five connection locations 50 between adjacent annular elements 10 is defined by a slightly overlapping pattern of the base portion 46 of each foot extension 40 with a corresponding apex 30 of a longitudinally-adjacent annular element in a manner similar to that of FIG. 27a In this manner, longitudinally-adjacent apices of adjacent annular elements are out of circumferential alignment with each other so as to be less than 180 degrees out of phase. Furthermore, connection locations 50 are circumferentially displaced or offset from one set of annular elements to the next.

The self-expanding stent of this preferred embodiment is made from a suitable tube stock of nickel-titanium alloy, such as SE508 or SM508, ASTM Standard F2063-00, comprising about 54.5 to about 57% wt. nickel and about 45.5 to about 42.7% wt. titanium, which is commercially available from Minitubes, Inc. of Grenoble, France. It is recognized, however, that alternative alloy compositions can be used if desired. For fabrication of a self-expanding stent having a deployed configuration diameter of about 7 mm to about 8 mm, the tube stock has an outer diameter of about 0.091 inch and a uniform wall thickness of about 0.010 inch. The tube stock is laser cut with the configuration shown in FIG. 29b as a continuous pattern around the circumference of the tube; wherein only the front half of the structure is shown for clarity. The cut tube is then mechanical blast and sequentially heat treated on a series of cylindrical mandrels of increasing diameter using known techniques to set the desired deployed configuration of the stent when in an austenitic state as shown in FIG. 29d. The heat set stent is then electropolished using known techniques. The relevant dimensions of the strut members for this preferred embodiment, after electropolishing, include a nominal strut length of about 0.055 inch, a nominal strut width of about 0.004 inches and a generally uniform thickness of about 0.008 inches. Regarding each foot extension, after electropolishing, the first portion of the foot extension has a width of about 0.005 inch and a length of about 0.013, as measured along its outer edge, and the base portion of the foot extension includes total length of about 0.033, as measured along its outer edge, with a first portion proximate the heel portion having a width of about 0.005 inch and a second portion proximate the toe portion having a width of about 0.007 inch. The strut member extending from the ankle portion of the foot extension tapers from a width of about 0.005 inch at the end proximate the foot extension to about 0.004 inch at the opposite end, with a length of about 0.059 inch. The strut member extending from the heel portion of the foot extension tapers from a width of about 0.005 inch at the end proximate the foot extension to about 0.004 inch at the opposite end, with a length of about 0.068 inch. After polishing, additional cleaning or preparation may be required.

Figure 29F:
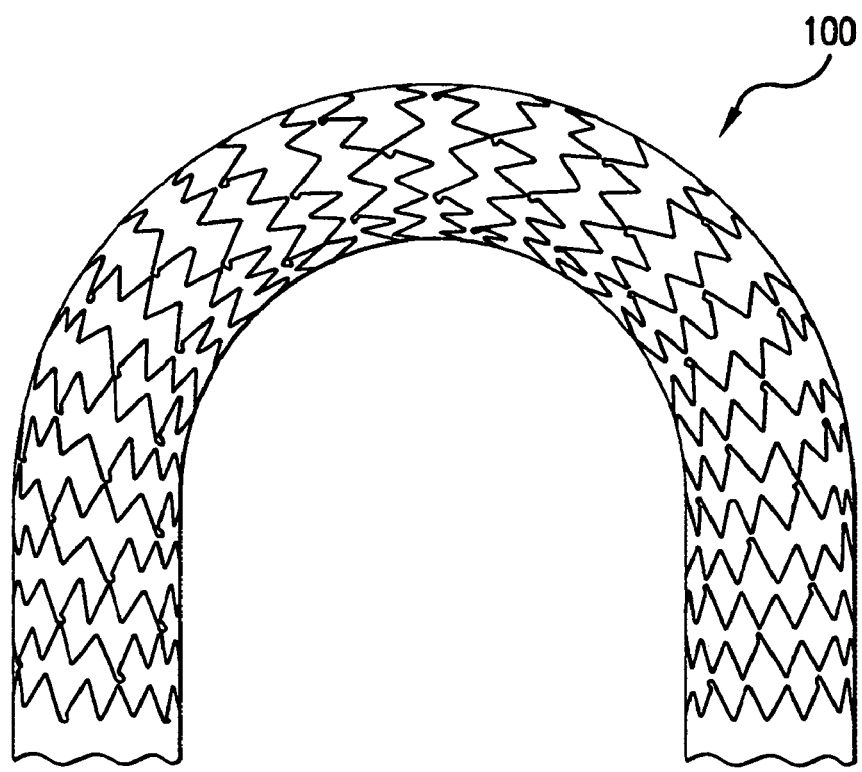

Once prepared, the self-expanding stent of this embodiment is compressed to a delivery configuration as shown in the front-half view of FIG. 29c, preferably with the strut members generally parallel to the longitudinal axis of the stent and each other. The stent can then be delivered using a conventional retractable sheath delivery catheter, as is known in the art. FIGS. 29d and 29e show the self-expanding stent of this embodiment in a deployed configuration. For purpose of clarity, only the front half of the stent is shown in FIG. 29d. As depicted, the stent of this embodiment has been balanced for generally uniform expansion. FIG. 29f shows a self-expanding stent of greater length of this embodiment deployed in a curved vessel, wherein the apices proximate the inner radius of the curve generally open less than the apices proximate the outer radius of the curve.

FIG. 30a shows the planar format of a preferred embodiment of a balloon expandable stent as cut and polished in a slightly deployed configuration. As depicted herein, the balloon expandable stent comprises fifteen annular elements 10 with two connection locations 50 between longitudinally-adjacent annular elements for an approximate stent length of about 18 mm. Annular elements can be added to increase the stent length, or omitted to decrease the stent length, as desired. Each annular element includes ten apices per longitudinal side. On one longitudinal side 12 of each annular element 10, two apices are defined by foot extensions 40. Four circumferentially-adjacent apices 30 are located between adjacent foot extensions. On the other longitudinal side 14 of each annular element 10, no foot extensions are provided. Each foot extension 40 has a shape similar to that of FIG. 2a, as previously described in detail. Each of the two connection locations 50 between adjacent annular elements 10 is defined by an overlapping pattern of the base portion 46 of each foot extension 40b with a corresponding apex 30 of a longitudinally-adjacent annular element in a manner similar to that of FIG. 26. In this manner, longitudinally-adjacent apices of adjacent annular elements are out of circumferential alignment with each other so as to be less than 180 degrees out of phase. Furthermore, connection locations 50 are circumferentially displaced or offset from one set of annular elements to the next.

The balloon expandable stent of this preferred embodiment is made from a suitable tube stock of composite material including an inner layer of 316L stainless steel, a middle layer of tantalum, and an outer layer of 316L stainless steel, which is available from UTI Corporation of Collegeville, Pa. It is recognized, however, that alternative material compositions can be used if desired. For fabrication of a balloon expandable stent having a deployed configuration diameter of about 2.75 mm to about 3.0 mm, the tube stock has an outer diameter of about 0.062 inch and a generally uniform wall thickness of about 0.004 inch, with the tantalum layer constituting between about 3% to about 50% of the wall thickness, and more preferably between about 10% to about 25% of the wall thickness depending upon the intended indication. For example, a coronary stent of this dimension preferably would have a tantalum layer of between about 15% to about 17% of the tube stock thickness. The tube stock is laser cut with the configuration shown in FIG. 30b as a continuous pattern around the circumference of the tube; only seven annular elements are depicted for purpose of clarity. The cut tube is then mechanically blasted and electropolished using known techniques. The relevant dimensions of the strut members for this preferred embodiment, after electropolishing, include a nominal strut length of about 0.036 inches, a nominal strut width of about 0.003 inches and a generally uniform thickness of about 0.003 inches. Regarding each foot extension, after electropolishing, the first portion of the foot extension has a width of about 0.005 inch and a length of about 0.008 inch, as measured along the outer edge, and the base portion of the foot extension has a width of about 0.005 inch and a length of about 0.021 inch as measure along the outer edge. The strut member extending from the ankle portion of the foot extension tapers from a width of about 0.004 inch at the end proximate the foot extension to about 0.003 inch at the opposite end, with a length of about 0.034 inch. The strut member extending from the heel portion of the foot extension tapers from a width of about 0.005 inch at the end proximate the foot extension to about 0.003 inch at the opposite end, with a length of about 0.042 inch. After electro polishing, additional cleaning or preparation may be required.

Figure 30F:
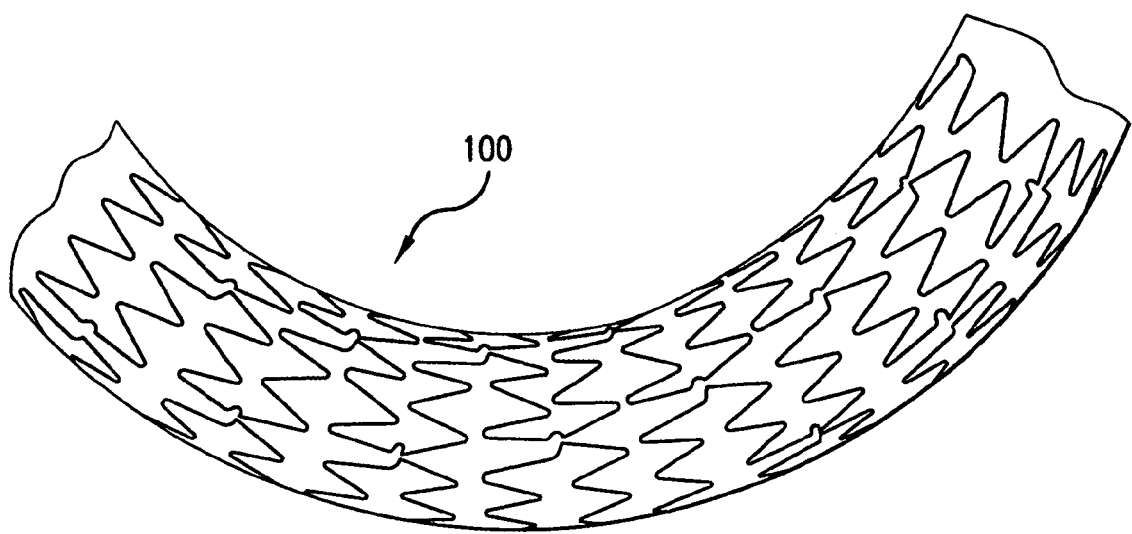

Once prepared, the balloon expandable stent of this embodiment is compressed to a delivery configuration as shown in FIG. 30c, with only seven annular elements depicted for purpose of clarity. Preferably, the strut members are generally parallel to the longitudinal axis of the stent and each other when in the delivery configuration. The stent can then be delivered using a conventional balloon delivery device, as is known in the art. Preferably, a portion of balloon material of the delivery device is captured in the gap defined by the foot extension and the circumferentially-adjacent strut member. FIGS. 30d and 30e show the balloon expandable stent of this embodiment in a deployed configuration; only seven annular elements are depicted for purpose of clarity. For purpose of clarity, only the front half of the stent is shown in FIG. 30d. As depicted, the stent of this embodiment has been balanced for generally uniform expansion. FIG. 30f shows the balloon expandable stent of this embodiment deployed in a curved vessel, wherein the apices proximate the inner radius of the curve generally open less than the apices proximate the outer radius of the curve. It is further contemplated that the endoprosthesis may include eyelets or tabs such as those shown in FIG. 25a, wherein the eyelets or tabs may be utilized to retain the endoprosthesis onto a balloon delivery device, wherein the balloon material may be received within the eyelet or tab during the crimping and/or heat setting process. Further still, a biocompatible adhesive may be disposed within the eyelet or tab after the endoprosthesis has been crimped onto the balloon delivery device such that the adhesive would releasably affix the endoprosthesis to the surface of the balloon of the balloon delivery device.

FIG. 31 is an exemplary cross-sectional view of an endoprosthesis device in accordance with the present invention. As shown in FIG. 31, the endoprosthesis device is manufactured having a cross-sectional profile which may be shaped to improve blood flow by decreasing the likelihood of turbulent currents and eddies formed near the struts of the endoprosthesis. An exemplary cross-sectional profile may be hemispherical in nature, wherein the rounded portion would be disposed on the inner radius of the endoprosthesis device, thereby placing the radiused portion within the blood flow. It shall be understood that he profiled illustrated in FIG. 31 should be considered exemplary, in that the inventors of the present invention contemplate that alternative cross-sectional profiles may be utilized to reduce the formation of thrombosis and/or turbulence of blood flow through the endoprosthesis device where the device is disposed in an expanded condition within a body lumen.

While illustrative embodiments of the invention have been disclosed herein, numerous modifications and other embodiments may be devised by those skilled in the art in accordance with the invention. For example, the various features depicted and described in the embodiments herein can be altered or combined to obtain desired endoprosthesis characteristics in accordance with the invention. Therefore, it will be understood that the appended claims are intended to cover all such modifications and embodiments, which are within the spirit and scope of the present invention.

What is claimed is:

1. An endoprosthesis for delivery in a body lumen comprising:
   a first set of interconnected strut members defining a first annular element, each strut member of the first annular element including a first end and a second end; and
   a second set of interconnected strut members defining a second annular element, each strut member of the second annular element including a first end and a second end,
   the first annular element and the second annular element aligned longitudinally adjacent to each other along a longitudinal axis and connected to each other with a connector at least one connection location, the connector having a L-shape including a first leg and a second leg angled relative to the first leg, wherein the connector is constructed of a bio-absorbable material.

2. The endoprosthesis of claim 1, further including a radiopaque marker housed in a marker housing associated with one of the annular elements and extending from one of the ends.

3. The endoprosthesis of claim 2, wherein the marker comprises a rivet.

4. The endoprosthesis of claim 1, wherein the connector further comprises a non-bio-absorbable material.

5. The endoprosthesis of claim 1, wherein the annular elements are fabricated from nitinol.

6. The endoprosthesis of claim 1, wherein the endoprosthesis is fabricated from a tubular member.

7. The endoprosthesis of claim 1, wherein the annular elements are fabricated from a material chosen from the group consisting of nitinol, tantalum, stainless steel, cobalt, a composite material.

8. The endoprosthesis of claim 1, wherein the endoprosthesis is balloon expandable.

9. The endoprosthesis of claim 1, wherein the endoprosthesis is self-expanding from a delivery profile to a deployed profile.

10. The endoprosthesis of claim 1, wherein the bio-absorbable material is chosen from the group consisting of Polygycolic acid (PGA), Polyhydroxybutyric acid, PolyL-Lactic acid (PLLA), Polydilactidel glycolide, Polydilactid acid, PolyDL lactide-co-gycolide.

11. An endoprosthesis for delivery in a body lumen comprising:
   a first set of interconnected strut members defining a first annular element; and
   a second set of interconnected strut members defining a second annular element;
   the first annular element and the second annular element disposed adjacent to each other and connected to each other with a connector at least one connection location, the connector having a L-shape including a first leg and a second leg angled relative to the first leg, wherein the first leg has a first length and the second leg has a second length different than the first length.

12. The endoprosthesis of claim 11, wherein the connector is made of a bio-absorbable material.

13. The endoprosthesis of claim 12, wherein the bio-absorbable material includes a beneficial agent.

14. The endoprosthesis of claim 12, wherein the bio-absorbable material is selectively bio-absorbable.

15. The endoprosthesis of claim 11, wherein the endoprosthesis is fabricated from a tubular member.

16. The endoprosthesis of claim 11, wherein the annular elements are fabricated from a material chosen from the group consisting of nitinol, tantalum, plastics, stainless steel, cobalt, or a composite material.

17. The endoprosthesis of claim 11, wherein one of the annular elements further includes at least one foot extension extending between a pair of circumferentially-adjacent strut members.

18. The endoprosthesis of claim 17, wherein the foot extension has a first foot portion extending circumferentially from a first end of one of the circumferentially-adjacent strut members and a second foot portion extending circumferentially from a first end of the other of the circumferentially-adjacent strut members.

19. The endoprosthesis of claim 18, wherein the first and second foot portions are joined at a toe portion of the foot extension.

20. The endoprosthesis of claim 12, wherein the bio-absorbable material is chosen from the group consisting of Polygycolic acid (PGA), Polyhydroxybutyric acid, PolyL-Lactic acid (PLLA), Polydilactidel glycolide, Polydilactid acid, PolyDL lactide-co-gycolide.

21. The endoprosthesis of claim 19, wherein the connector extends from one foot extension to another foot extension.

22. The endoprosthesis of claim 11, wherein the connector is configured to be responsive to an applied energy.

23. The endoprosthesis of claim 22, wherein the applied energy is selected from the group consisting of ultrasonic and radio frequency.

24. The endoprosthesis of claim 11, wherein the connector comprises a bio-absorbable component and a metallic component.

25. The endoprosthesis of claim 11, wherein the connector has a first end connected to a first apex defined between a pair of circumferentially-adjacent strut members of the first annular element, and a second end connected to a second apex defined between a pair of circumferentially-adjacent strut members of the second annular element.

26. The endoprosthesis of claim 25, wherein the first apex and the second apex are longitudinally aligned and opposing each other.

27. The endoprosthesis of claim 25, wherein the first apex and the second apex are longitudinally offset from each other.

28. The endoprosthesis of claim 11, wherein the connector has a first end connected to a first apex defined between a pair of circumferentially-adjacent strut members of the first annular element, and a second end connected to connected to an intermediate portion of a strut member of the second annular element.

29. The endoprosthesis of claim 11, further comprising a second connector having a L-shape, the second connector disposed circumferentially adjacent the first connector with the first connector and the second connector extending circumferentially in opposite directions.

30. The endoprosthesis of claim 11, wherein the at least one connector includes a first L-shaped connector and a second L-shaped connector, the first L-shaped connector and the second L-shaped connector each having a first end connected at a first connection location on the first annular element, and further wherein the first L-shaped connector and the second L-shaped connector each has a second end connected at different connection locations on the second annular element.

31. The endoprosthesis of claim 30, wherein the first connection location is at an apex defined between a pair of circumferentially-adjacent strut members of the first annular element.

32. The endoprosthesis of claim 30, wherein at least one of the second ends of the first L-shaped connector and the second L-shaped connector is connected at an apex defined between a pair of circumferentially-adjacent strut members of the second annular element.

33. The endoprosthesis of claim 30, wherein at least one of the second ends of the first L-shaped connector and the second L-shaped connector is connected to an intermediate portion of a strut member of the second annular element.

34. The endoprosthesis of claim 11, further comprising:
a third set of interconnected strut members defining a third annular element,
the second annular element and the third annular element aligned longitudinally adjacent to each other along a longitudinal axis and connected to each other with a second connector having a L-shape.

35. The endoprosthesis of claim 34, wherein the connector between the first annular element and the second annular element and the second connector between the second annular element and the third annular element are circumferentially displaced from each other.

* * * * *